(12) United States Patent
Adams et al.

(10) Patent No.: US 10,004,723 B2
(45) Date of Patent: Jun. 26, 2018

(54) AROMATASE INHIBITOR-RELEASING INTRAVAGINAL DEVICE

(71) Applicant: University of Saskatchewan, Saskatoon (CA)

(72) Inventors: Gregg Patrick Adams, Saskatoon (CA); Maria Jimena Yapura, Palmerston North (NZ); Roger A. Pierson, Saskatoon (CA); Ildiko Badea, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days. days.

(21) Appl. No.: 14/785,220

(22) PCT Filed: Apr. 17, 2014

(86) PCT No.: PCT/CA2014/050390
§ 371 (c)(1),
(2) Date: Oct. 16, 2015

(87) PCT Pub. No.: WO2014/169395
PCT Pub. Date: Oct. 23, 2014

(65) Prior Publication Data
US 2016/0067225 A1 Mar. 10, 2016

Related U.S. Application Data

(60) Provisional application No. 61/813,967, filed on Apr. 19, 2013.

(51) Int. Cl.
| | |
|---|---|
| *A61K 31/4196* | (2006.01) |
| *A61K 47/24* | (2006.01) |
| *A61K 47/28* | (2006.01) |
| *A61K 47/44* | (2017.01) |
| *A61K 31/5575* | (2006.01) |
| *A61K 9/00* | (2006.01) |
| *A61K 9/127* | (2006.01) |
| *A61K 31/437* | (2006.01) |
| *A61K 38/24* | (2006.01) |
| *A61K 45/06* | (2006.01) |
| *A61K 47/10* | (2017.01) |
| *A61K 47/42* | (2017.01) |

(52) U.S. Cl.
CPC ........ *A61K 31/4196* (2013.01); *A61K 9/0034* (2013.01); *A61K 9/0036* (2013.01); *A61K 9/127* (2013.01); *A61K 31/437* (2013.01); *A61K 31/5575* (2013.01); *A61K 38/24* (2013.01); *A61K 45/06* (2013.01); *A61K 47/10* (2013.01); *A61K 47/24* (2013.01); *A61K 47/28* (2013.01); *A61K 47/42* (2013.01); *A61K 47/44* (2013.01)

(58) Field of Classification Search
CPC .............. A61K 31/4196; A61K 31/437; A61K 31/5575; A61K 38/24; A61K 47/10; A61K 47/24; A61K 47/28; A61K 47/42; A61K 47/44; A61K 9/0034; A61K 9/0036; Y10S 514/967; Y10S 424/15
See application file for complete search history.

(56) References Cited

U.S. PATENT DOCUMENTS

| 5,227,375 A | 7/1993 | Labrie et al. |
|---|---|---|
| 9,144,569 B2 | 9/2015 | Pierson et al. |
| 2005/0049231 A1 | 3/2005 | Knox et al. |
| 2005/0276836 A1* | 12/2005 | Wilson ................ A61F 13/2051 424/422 |
| 2009/0016910 A1 | 1/2009 | Shih |
| 2009/0169610 A1 | 7/2009 | Yamazaki et al. |
| 2010/0144659 A1* | 6/2010 | Niitsu .................. A61K 9/0019 514/34 |
| 2013/0046275 A1* | 2/2013 | Holzer ................ A61K 9/0024 604/500 |
| 2014/0121185 A1* | 5/2014 | Rigas ...................... C07F 9/091 514/81 |
| 2014/0275242 A1* | 9/2014 | Xiao .................... A61K 9/1617 514/476 |

FOREIGN PATENT DOCUMENTS

| CA | 2444932 A1 | 10/2002 |
|---|---|---|
| CA | 2444980 A1 | 10/2002 |
| CA | 2472309 A1 | 10/2002 |

(Continued)

OTHER PUBLICATIONS

Garg et al., "Compendium of Pharmaceutical Excipients for Vaginal Formulations", 2001, Pharmaceutical Technology, pp. 14-24.*
Adams et al., "Bovine model for study of ovarian follicular dynamics in humans," Theriogenology. 43(1):113-20 (1995).
Adams et al., "Effect of progesterone on ovarian follicles, emergence of follicular waves and circulating follicle-stimulating hormone in heifers," J Reprod Fertil. 96(2):627-40 (1992).
Adams et al., "Effect of the dominant follicle on regression of its subordinates in heifers," Canadian Journal of Animal Science. 73(2):267-75 (1993).

(Continued)

*Primary Examiner* — Michael B. Pallay
(74) *Attorney, Agent, or Firm* — Clark & Elbing LLP

(57) ABSTRACT

An intravaginal device that provides biologically active circulating concentrations of an aromatase inhibitor for at least about of 4 days. Liposome-based and a wax-based formulations were used to assess letrozole diffusion through bovine vaginal mucosa in a diffusion chamber study. The wax-based vehicle was selected for further development of a letrozole intravaginal device based on its steady release rate. The addition of a letrozole-containing gel coating improved initial absorption and hastened the increase on plasma concentrations of the active ingredient, while the letrozole-containing wax-based vehicle maintained prolonged delivery from the intravaginal device.

10 Claims, 14 Drawing Sheets

(56) References Cited

FOREIGN PATENT DOCUMENTS

| CA | 2589824 A1 | 6/2006 |
|---|---|---|
| CA | 2837494 A1 | 11/2011 |
| WO | WO-03/015872 A2 | 2/2003 |
| WO | WO-2011/143752 A1 | 11/2011 |

OTHER PUBLICATIONS

Adams, "Control of ovarian follicular wave dynamics in cattle: implications for synchronization & superstimulation," Theriogenology. 41(1):19-24 (1994).
Adams et al., "Association between surges of follicle-stimulating hormone and the emergence of follicular waves in heifers," J Reprod Fertil. 94(1):177-88 (1992).
Adams, "Comparative patterns of follicle development and selection in ruminants," J Reprod Fertil Suppl. 54:17-32 (1999) (17 pages).
Al-Fadhli et al., "A randomized trial of superovulation with two different doses of letrozole," Fertil Steril. 85(1):161-4 (2006).
Allaway et al., "A single 20 mg dose of aromatase inhibitor (AI) does not effect folliculogenesis in the follicular phase of the menstrual cycle," 56th Annual Meeting of the Canadian Fertility and Andrology Society. Vancouver, British Columbia, Canada, Sep. 29, 2010 (1 page).
Amer, "New Trends for Estrus Synchronization Using a Combination of Gonadotropins, Prostaglandin and Estradiol Cypionate in Dairy Cows," Internet J Vet Med. 3(2) (2007) (16 pages).
Andersson et al., "Exposure to exogenous estrogens in food: possible impact on human development and health," Eur J Endocrinol. 140(6):477-85 (1999).
At-Taras et al., "Reducing estrogen synthesis does not affect gonadotropin secretion in the developing boar," Biol Reprod. 74(1):58-66 (2006).
Austin et al., "Effect of duration of dominance of the ovulatory follicle on onset of estrus and fertility in heifers," J Anim Sci. 77(8):2219-26 (1999).
Baerwald et al., "A new model for ovarian follicular development during the human menstrual cycle," Fertil Steril. 80(1):116-22 (2003).
Baerwald et al., "Characterization of ovarian follicular wave dynamics in women," Biol Reprod. 69(3):1023-31 (2003).
Baliharova et al., "Inhibitory effect of albendazole and its metabolites on cytochromes P450 activities in rat and mouflon in vitro," Pharmacol Rep. 57(1):97-106 (2005).
Baracaldo et al., "Superovulatory response following transvaginal follicle ablation in cattle," Theriogenology. 53(6):1239-50 (2000).
Bayar et al., "Letrozole vs. clomiphene citrate in patients with ovulatory infertility," Fertil Steril. 85(4):1045-8 (2006).
Beatson, "Classics in oncology: On the treatment of inoperable cases of carcinoma of the mamma: suggestions for a new method of treatment, with illustrative cases," CA Cancer J Clin. 33(2):108-121 (1983).
Beker et al., "Effect of 17beta-estradiol on the in vitro maturation of bovine oocytes," Theriogenology. 58(9):1663-73 (2002).
Beker-van Woudenberg et al., "Estradiol and its membrane-impermeable conjugate (estradiol-bovine serum albumin) during in vitro maturation of bovine oocytes: effects on nuclear and cytoplasmic maturation, cytoskeleton, and embryo quality," Biol Reprod. 70(5):1465-74 (2004).
Belanger et al., "Determination of nonconjugated and conjugated steroid levels in plasma and prostate after separation on C-18 columns," Ann N Y Acad Sci. 595:251-59 (1990).
Benoit et al., "Effect of a nonsteroidal aromatase inhibitor on in vitro and in vivo secretion of estradiol and on the estrous cycle in ewes," Domest Anim Endocrinol. 9(4):313-327 (1992) (Abstract only).
Bergfelt et al., "Follicular and hormonal response to experimental suppression of FSH during follicle deviation in cattle," Theriogenology. 54(8)1 191-206 (2000).

Bergfelt et al., "Ovarian synchronization following ultrasound-guided transvaginal follicle ablation in heifers," Theriogenology. 42(6):895-907 (1994).
Bergfelt et al., "Surges of FSH during the follicular and early luteal phases of the estrous cycle in heifers," Theriogenology. 48(5):757-68 (1997).
Bergfelt et al., "Ovulation synchronization following commercial application of ultrasound-guided follicle ablation during the estrous cycle in mares," Theriogenology. 68(8):1183-91 (2007).
Bhatnagar, "The discovery and mechanism of action of letrozole," Breast Cancer Res Treat. 105(Suppl 1):7-17 (2007).
Bhatnagar et al., "Intracellular aromatase and its relevance to the pharmacological efficacy of aromatase inhibitors," J Steroid Biochem Mol Biol. 76(1-5):199-202 (2001).
Bhatnagar et al., "Highly selective inhibition of estrogen biosynthesis by CGS 20267, a new non-steroidal aromatase inhibitor," J Steroid Biochem Mol Biol. 37(6)1 021-27 (1990).
Bleach et al., "Plasma inhibin A in heifers: relationship with follicle dynamics, gonadotropins, and steroids during the estrous cycle and after treatment with bovine follicular fluid," Biol Reprod. 64(3):743-52 (2001).
Bo et al., "Exogenous control of follicular wave emergence in cattle," Theriogenology. 43(1):31-40 (1995).
Bo et al., "Ovarian follicular wave emergence after treatment with progestogen and estradiol in cattle," Anim Reprod Sci. 39(3):193-204 (1995).
Bodensteiner et al., "Alterations in follicular estradiol and gonadotropin receptors during development of bovine antral follicles," Theriogenology. 45(2):499-512 (1996).
Bridges et al., "Follicular growth, estrus and pregnancy after fixed-time insemination in beef cows treated with intravaginal progesterone inserts and estradiol benzoate," Theriogenology. 52(4):573-83 (1999).
Buzdar, "Pharmacology and Pharmacokinetics of the Newer Generation Aromatase Inhibitors," Clin Cancer Res. 9(1):468s-472s (2003) (8 pages).
Budzar et al., "An overview of the pharmacology and pharmacokinetics of the newer generation aromatase inhibitors anastrozole, letrozole, and exemestane," Cancer. 95(9):2006-16 (2002).
Casper, "Letrozole: ovulation or superovulation?" Fertil Steril. 80(6)1 335-7 (2003).
Casper et al., "Review: aromatase inhibitors for ovulation induction," J Clin Endocrinol Metab. 91(3):760-71 (2006).
Cohen et al., "Approval summary: letrozole in the treatment of postmenopausal women with advanced breast cancer," Clin Cancer Res. 8(3):665-9 (2002).
Colazo et al., "Fertility following fixed-time AI in CIDR-treated beef heifers given GnRH or estradiol cypionate and fed diets supplemented with flax seed or sunflower seed," Theriogenology. 61(6):1115-24 (2004).
Cordoba-Diaz et al., "Validation protocol of an automated in-line flow-through diffusion equipment for in vitro permeation studies," J Control Release. 69(3):357-67 (2000).
Cortinez et al., "Hormonal profile and endometrial morphology in letrozole-controlled ovarian hyperstimulation in ovulatory infertile patients," Fertil Steril. 83(1):110-5 (2005).
Davar et al., "Comparison of the success rate of letrozole and clomiphene citrate in women undergoing intrauterine insemination," J Res Med Sci. 11(6):382-7 (2006).
Daxenberger et al., "Possible health impact of animal oestrogens in food," Hum Reprod Update. 7(3):340-55 (2001).
De Rensis et al., "The control of follicular dynamics by PGF2alpha, gnrh, hCG and oestrus synchronization in cattle," Reprod Dom Anim. 34(2):49-59 (1999).
De Ziegler, "The dawning of the non-cancer uses of aromatase inhibitors in gynaecology," Hum Reprod. 18(8):1598-602 (2003).
Dukes et al., "The preclinical pharmacology of "Arimidex" (anastrozole; ZD1033)—a potent, selective aromatase inhibitor," J Steroid Biochem Mol Biol. 58(4):439-45 (1996).
Ebert et al., "Aromatase inhibitors and cyclooxygenase-2 (COX-2) inhibitors in endometriosis: new questions—old answers?" Eur J Obstet Gynecol Reprod Biol. 122(2):144-50 (2005).

(56) References Cited

OTHER PUBLICATIONS

Endo et al., "Estradiol supports in vitro development of bovine early antral follicles," Reproduction. 145(1):85-96 (2013).
Evans et al., "Endocrine and ovarian follicular changes leading up to the first ovulation in prepubertal heifers," J Reprod Fertil. 100(1):187-94 (1994).
Extended European Search Report for European Application No. 11782809, dated Oct. 9, 2013 (8 pages).
Fatum et al., "Is estradiol mandatory for an adequate follicular and embryo development? A mouse model using aromatase inhibitor (anastrozole)," J Assist Reprod Gen. 23(11-12):407-12 (2006).
FEMA Drug Approval Package, Application No. NDA 20-726, dated Jul. 25, 1997 (545 pages).
Fisher et al., "A randomized double-blind comparison of the effects of clomiphene citrate and the aromatase inhibitor letrozole on ovulatory function in normal women," Fertil Steril. 78(2):280-5 (2002).
Foldvari et al., "Biphasic vesicles for topical delivery of interferon alpha in human volunteers and treatment of patients with human papillomavirus infections," Curr Drug Deliv. 8(3):307-19 (2011).
Fritsche et al., "Occurrence of hormonally active compounds in food: a review," Eur Food Res Technol. 209(3):153-79 (1999).
Fukushima et al., "Effects of gonadotropins and steroids on the subsequent fertilizability of extrafollicular bovine oocytes cultured in vitro," Anim Reprod Sci. 9(4):323-32 (1985).
Gibbs, "Is veterinary compounding illegal under federal law?" Int J Pharm Compd. 8(6):449-50 (2004).
Galbraith, "Hormones in international meat production: biological, sociological and consumer issues," Nutr Res Rev. 15(2):293-314 (2002).
Garverick et al., "Mechanisms associated with corpus luteum lifespan in animals having normal or subnormal luteal function," Anim Reprod Sci. 28(1-4):111-24 (1992).
Geisler et al., "Influence of letrozole and anastrozole on total body aromatization and plasma estrogen levels in postmenopausal breast cancer patients evaluated in a randomized, cross-over study," J Clin Oncol. 20(3):751-7 (2002).
Ginther et al., "Follicle Selection in Cattle: Relationships among Growth Rate, Diameter Ranking, and Capacity for Dominance," Biol Reprod. 65(2):345-50 (2001).
Ginther et al., "Mechanism of follicle deviation in monovular farm species," Anim Reprod Sci. 78(3-4):239-57 (2003).
Ginther et al., "Selection of the dominant follicle in cattle: role of estradiol," Biol Reprod. 63(2):383-9 (2000).
Ginther et al., "Temporal associations among ovarian events in cattle during oestrous cycles with two and three follicular waves," J Reprod Fertil. 87(1):223-30 (1989).
Ginther et al., "Emergence and deviation of follicles during the development of follicular waves in cattle," Theriogenology. 48(1):75-87 (1997).
Ginther et al., "Selection of the dominant follicle in cattle," Biol Reprod. 55(6):1187-94 (1996).
Gombe et al., "Regulation of blood levels of LH in bulls: influence of age, breed, sexual stimulation and temporal fluctuations," J Reprod Fertil. 35(3):493-503 (1973).
Hafez et al., "Roles of lipid polymorphism in intracellular delivery," Adv Drug Deliv Rev. 47(2-3):139-48 (2001).
Hafs et al., "Control of the estrous cycle with prostaglandin F2alpha in cattle and horses," J Anim Sci. 38(Suppl 1):10-21 (1974).
Harper et al., "Effects of GnRH in combination with PGF2alpha on the dynamics of follicular and luteal cells in post-pubertal Holstein heifers," Livest Sci. 117(1):88-92 (2008).
Healey et al., "Effects of letrozole on superovulation with gonadotropins in women undergoing intrauterine insemination," Fertil Steril. 80(6)1325-9 (2003).
Health Canada, "Questions and answers: Hormonal growth promoters," <http://www.hc-sc.gc.ca/dhp-mps/vet/faq/growth_hormones_promoters_croissance_hormonaux_stimulateurs-eng.php>, retrieved on Dec. 11, 2012 (2 pages).

Hecker et al., "Effects of atrazine on CYP19 gene expression and aromatase activity in testes and on plasma sex steroid concentrations of male African clawed frogs (Xenopus laevis)," Toxicol Sci. 86(2):273-80 (2005).
Hefler et al., "Role of the vaginally administered aromatase inhibitor anastrozole in women with rectovaginal endometriosis: a pilot study," Fertil Steril. 84(4):1033-6 (2005).
Hong et al., "Aromatase inhibitors: structural features and biochemical characterization,"Ann N Y Acad Sci. 1089:237-51 (2006).
International Search Report and Written Opinion for International Application No. PCT/CA2011/000578, dated Aug. 22, 2011 (16 pages).
International Preliminary Report on Patentablility for International Application No. PCT/CA2011/000578, dated Nov. 20, 2012 (9 pages).
Ireland et al., "Effect of progesterone on basal LH and episodic LH and FSH secretion in heifers," J Reprod Fertil. 64(2):295-302 (1982).
Jee et al., "Use of letrozole versus clomiphene citrate combined with gonadotropins in intrauterine insemination cycles: a pilot study," Fertil Steril. 85(6):1774-7 (2006).
Ji et al., "Endogenous opiates regulate the nocturnal reduction in luteinizing hormone pulse frequency during the luteal phase of the macaque menstrual cycle," Biol Reprod. 41(6):1024-33 (1989).
Johnson et al., Adult Ovarian Function. Essential Reproduction. Johnson-Everitt, 85-86 (2000).
Johnston et al., "Fenbendazole treatment and litter size in rats," J Am Assoc Lab Anim Sci. 45(6):35-9 (2006).
Joshi et al., "Validation and application of a high-performance liquid chromatography-tandem mass spectrometry assay for letrozole in human plasma," Asian J Pharm Clin Res. 4(2):107-12 (2011).
Kaneko et al., "Changes in Plasma Concentrations of Immunoreactive Inhibin, Estradiol and FSH Associated with Follicular Waves during the Estrous Cycle of the Cow," J Reprod Dev. 41(4):311-20 (1995).
Kastelic et al., "Effect of day of prostaglandin F2alpha treatment on selection and development of the ovulatory follicle in heifers," Anim Reprod Sci. 23(3):169-80 (1990).
Kim et al., "Follicular wave emergence, luteal function and synchrony of ovulation following GnRH or estradiol benzoate in a CIDR-treated, lactating Holstein cows," Theriogenology. 63(1):260-8 (2005).
Knopf et al., "Ovarian follicular dynamics in heifers: test of two-wave hypothesis by ultrasonically monitoring individual follicles," Domest Anim Endocrinol. 6(2):111-9 (1989).
Kolok et al., "The environmental impact of growth-promoting compounds employed by the United States beef cattle industry: History, current knowledge, and future directions," Rev Environ Contam Toxicol. 195:1-30 (2008).
Kragie et al., "Assessing pregnancy risks of azole antifungals using a high throughput aromatase inhibition assay," Endocrine Res. 28(3):129-40 (2002).
Kulick et al., "Follicular and hormonal dynamics during the first follicular wave in heifers," Theriogenology. 52(5):913-21 (1999).
Lamb et al., "Control of the estrous cycle to improve fertility for fixed-time artificial insemination in beef cattle: a review," J Anim Sci. 88(13 Suppl.):E181-92 (2010).
Lane et al., "Oestrous synchronisation in cattle—current options following the EU regulations restricting use of oestrogenic compounds in food-producing animals: a review," Anim Reprod Sci. 109(1-4):1-16 (2008).
Li et al., "Formulation and biopharmaceutical evaluation of a transdermal patch containing letrozole," Biopharm Drug Dispos. 31(2-3):138-49 (2010).
Macmillan et al., "Effects of an agonist of gonadotropin-releasing hormone on ovarian follicles in cattle," Biol Reprod. 45(6):883-9 (1991).
Makoid et al., Basic Pharmacokinetics. (1996) (804 pages).
Malhi et al., "Bovine model for the study of reproductive aging in women: follicular, luteal, and endocrine characteristics," Biol Reprod. 73(1):45-53 (2005).

(56) References Cited

OTHER PUBLICATIONS

Malhi et al., "Bovine model of reproductive aging: response to ovarian synchronization and superstimulation," Theriogenology. 66(5):1257-66 (2006).
Malhi et al., "Oocyte developmental competence in a bovine model of reproductive aging," Reproduction. 134(2):233-9 (2007).
Mamali et al., "The effect of albendazole administration on the concentration of ovarian steroids in the follicular fluid and the maturation of oocytes in the ewe," Reprod Domest Anim. 43:192 (2008).
Mann et al., "The role of sub-optimal preovulatory oestradiol secretion in the aetiology of premature luteolysis during the short oestrous cycle in the cow," Anim Reprod Sci. 64(3)1 71-80 (2000).
Mapletoft et al., "Summary of embryo transfer activity in Canada for 2009," <http://www.ceta.ca/pdfs/2009-ET-Activity-in-Canada.pdf> (2 pages).
Martinez et al., "Induction of follicular wave emergence for estrus synchronization and artificial insemination in heifers," Theriogenology. 54(5):757-69 (2000).
Martinez et al., "Effects of estradiol on gonadotrophin release, estrus and ovulation in CIDR-treated beef cattle," Domest Anim Endocrinol. 33(1):77-90 (2007).
Mihm et al., "Effect of dominant follicle persistence on follicular fluid oestradiol and inhibin and on oocyte maturation in heifers," J Reprod Fert. 116(2):293-304 (1999).
Miller et al., "Interaction of estradiol and a nonsteroidal follicular fluid substance in the regulation of gonadotropin secretion in the mare," Biol Reprod. 24(2):354-8 (1981).
Miller et al., "Ovarian effects of bovine follicular fluid treatment in sheep and cattle," Biol Reprod. 21(3):537-44 (1979).
Mitwally et al., "Aromatase inhibition improves ovarian response to follicle-stimulating hormone in poor responders," Fertil Steril. 77(4):776-80 (2002).
Mitwally et al., "Aromatase inhibition reduces the dose of gonadotropin required for controlled ovarian hyperstimulation," J Soc Gynecol Investig. 11(6):406-15 (2004).
Mitwally et al., "Potential of aromatase inhibitors for ovulation and superovulation induction in infertile women," Drugs. 66(17):2149-60 (2006).
Mitwally et al., "Single-dose administration of an aromatase inhibitor for ovarian stimulation," Fertil Steril. 83(1):229-31 (2005).
Mitwally et al., "Letrozole step-up protocol: A successful superovulation protocol," Fertil Steril. 89(Suppl 2):S23-4 (2008).
Nasser et al., "Ovarian superstimulatory response relative to follicular wave emergence in heifers," Theriogenology. 40(4):713-24 (1993).
Mitwally et al., "Use of an aromatase inhibitor for induction of ovulation in patients with an inadequate response to clomiphene citrate," Fertil Steril. 75(2):305-9 (2001).
Mitwally et al., "Aromatase inhibition for ovarian stimulation: future avenues for infertility management," Curr Opin Obstet Gynecol. 14(3):255-63 (2002).
Murray et al., "Hepatic microsomal metabolism of the anthelmintic benzimidazole fenbendazole: enhanced inhibition of cytochrome P450 reactions by oxidized metabolites of the drug," Chem Res Toxicol. 5(1):60-6 (1992).
Notice of Opposition for New Zealand Application No. 603548, dated Oct. 24, 2014 (3 pages).
Office Action for European Application No. 11782809, dated Jun. 24, 2014 (8 pages).
"Directive 2003/74/EC of the European Parliament and of the Council of Sep. 22, 2003 amending Council Directive 96/22/EC concerning the prohibition on the use in stockfarming of certain substances having a hormonal or thyristatic action and of beta-agonist," Official Journal of the European Union. L 262, pp. 17-21 (2003).
Ottobre et al., "Aspects of regulation of uterine secretion of prostaglandins during the oestrous cycle and early pregnancy," Anim Reprod Sci. 7:75-100 (1984).

Peter et al., "Compilation of classical and contemporary terminology used to describe morphological aspects of ovarian dynamics in cattle," Theriogenology. 71(9):1343-57 (2009).
Pierson et al., "Reliability of diagnostic ultrasonography for identification and measurement of follicles and detecting the corpus luteum in heifers," Theriogenology. 28(6):929-36 (1987).
Price et al., "Steroid control of gonadotropin secretion and ovarian function in heifers," Endocrinology. 122(5):2222-31 (1988).
Pursley et al., "Synchronization of ovulation in dairy cows using PGF2alpha and GnRH," Theriogenology. 44(7):915-23 (1995).
Rawlings et al., "The influence of estradio1-17beta and progesterone on peripheral serum concentrations of luteinizing hormone and follicle stimulating hormone in the ovariectomized ewe," Theriogenology. 22(5):473-88 (1984).
Rantala et al., "Effect of time interval between prostaglandin F(2alpha) and GnRH treatments on occurrence of short estrous cycles in cyclic dairy heifers and cows," Theriogenology. 71(6):930-8 (2009).
Rathbone, "Delivering drugs to farmed animals using controlled release science and technology," IeJSME. 6(Suppl 1):S118-28 (2012).
Requena et al., "Use of letrozole in assisted reproduction: a systematic review and meta-analysis," Hum Reprod Update. 14(6):571-82 (2008).
Rettenmaier, "A comparative study of two types of prostaglandins for abortion during the second trimester," Surg Gynecol Obstet. 156(5):585-8 (1983) (Abstract only).
Revah et al., "Prolonged dominance of follicles and reduced viability of bovine oocytes," J Reprod Fertil. 106(1):39-47 (1996).
Roark et al., "Physiological and histological phenomena of the bovine estrual cycle with special reference to vaginal cervical secretions," Research Bulletin. Univ of Missouri Agricultural Experiment Station (1950) (64 pages).
Sanchez et al., "Dosage of the synthetic progestin, norgestomet, influences luteinizing hormone pulse frequency and endogenous secretion of 17 beta-estradiol in heifers," Biol Reprod. 52(2):464-9 (1995).
Sanyal, "Pharmacokinetic behaviour of fenbendazole in buffalo and cattle," J Vet Pharmacol Ther. 17(1):1-4 (1994).
Savio et al., "Effects of induction of low plasma progesterone concentrations with a progesterone-releasing intravaginal device on follicular turnover and fertility in cattle," J Reprod Fertil. 98(1):77-84 (1993).
Savio et al., "Regulation of dominant follicle turnover during the oestrous cycle in cows," J Reprod Fertil. 97(1):197-203 (1993).
Singh et al., "Ultrasound image attributes of bovine ovarian follicles and endocrine and functional correlates," J Reprod Fertil. 112(1):19-29 (1998).
Sianangama et al., "Characteristics of corpus luteum formed from the first wave dominant follicle following hCG in cattle," Theriogenology. 45(5):977-90 (1996).
Simpson et al., "Aromatase cytochrome P450, the enzyme responsible for estrogen biosynthesis," Endocr Rev. 15(3):342-55 (1994).
Sinha et al., "Effect of CGS 20267 on ovarian aromatase and gonadotropin levels in the rat," Breast Cancer Res Treat. 48(1):45-51 (1998).
Sioufi et al., "Absolute bioavailability of letrozole in healthy postmenopausal women," Biopharm Drug Dispos. 18(9):779-89 (1997).
Sioufi et al., "Comparative bioavailability of letrozole under fed and fasting conditions in 12 healthy subjects after a 2.5 mg single oral administration," Biopharm Drug Dispos. 18(6):489-97 (1997).
Stock et al., "Ovarian follicular dominance in cattle: relationship between prolonged growth of the ovulatory follicle and endocrine parameters," Endocrinology. 132(3)1108-14 (1993).
Taft et al., "Exogenous pulses of luteinizing hormone cause persistence of the largest bovine ovarian follicle," J Anim Sci. 74(12):2985-91 (1996).
Taponen et al., "Premature prostaglandin F2alpha secretion causes luteal regression in GnRH-induced short estrous cycles in cyclic dairy heifers," Theriogenology. 60(2):379-93 (2003).

(56) References Cited

OTHER PUBLICATIONS

Taponen et al., "Short estrous cycles and estrous signs after premature ovulations induced with cloprostenol and gonadotropin-releasing hormone in cyclic dairy cows," Theriogenology. 58(7):1291-302 (2002).
Thibier et al., "World statistics for artificial insemination in cattle" Livestock Production Science. 74(2):203-12 (2002).
Thibier, "The worldwide activity in farm animals embryo transfer," Embryo Transfer Newsletter, pp. 4-9 (2008).
Topipat et al., "A comparison of the effects of clomiphene citrate and the aromatase inhibitor letrozole on superovulation in Asian women with normal ovulatory cycles," Gynecol Endocrinol. 24(3):145-50 (2008).
Umberger, "Products marketed to promote growth in food-producing animals: steroid and hormone products," Toxicology. 3(1):3-21 (1975).
US Food and Drug Administration, "Compounding of drugs for use in animals," <http://www.fda.gov/ora/compliance_ref/cpg/cpgvet/cpg608-400compounding.pdf>, issued Jun. 26, 1996 (7 pages).
US Food and Drug Administration, "Guidance for Industry: Bioanalytical Method Validation," <http://www.fda.gov/downloads/Drugs/GuidanceComplianceRegulatoryInformation/Guidances/ucm070107.pdf>, dated May 2001 (25 pages).
USDA Foreign Agricultural Service, "Historic Overview and Chronology of EU's Hormone Ban," <http://www.fas.usda.gov/gainfiles/200311/145986773.pdf>, dated Nov. 7, 2003 (10 pages).
Valentini et al., "An electrochemical ELISA procedure for the screening of 17beta-estradiol in urban waste waters," Analyst. 127(10):1333-7 (2002).
Vasconcelos et al., "Synchronization rate, size of the ovulatory follicle, and pregnancy rate after synchronization of ovulation beginning on different days of the estrous cycle in lactating dairy cows," Theriogenology. 52(6):1067-78 (1999).
Wilks et al., "Oxytocin and the secretion of luteinizing hormone in cattle," J Anim Sci. 33(5):1048-52 (1971).
Yapura et al., "Effects of a non-steroidal aromatase inhibitor on ovarian function in cattle," Reprod Fertil Dev. 24(4):631-40 (2012).
Yapura et al., "Effects of vehicle and route of administration of letrozole on ovarian function in cattle," Reprod Fertil Develop. 23(1):190 (2011).
Yapura et al., "Effect of vehicle and route of administration of letrozole on ovarian function in a bovine model," Reprod Fertil Dev. 26(8):1198-205 (2014).
Yapura et al., "Aromatase inhibitor treatment with an intravaginal device and its effect on pre-ovulatory ovarian follicles in a bovine model," Reprod Biol Endocrinol. 11:97 (2013) (8 pages).
Yapura et al., "A bovine model for examining the effects of an aromatase inhibitor on ovarian function in women," Fertil Steril. 96(2):434-8.e3 (2011).
Yapura et al., "Effect of a prolonged aromatase inhibitor treatment on pre-ovulatory ovarian follicles in cattle," Reprod Fertil Dev. 24(1):113 (2011) (Abstract only).
Zamberlam et al., "Regulation of inducible nitric oxide synthase expression in bovine ovarian granulosa cells," Mol Cell Endocrinol. 335(2):189-94 (2011).
Zelinski-Wooten et al., "Administration of an aromatase inhibitor during the late follicular phase of gonadotropin-treated cycles in rhesus monkeys: effects on follicle development, oocyte maturation, and subsequent luteal function," J Clin Endocrinol Metab. 76(4):988-95 (1993).
Adams et al., "Selection of a dominant follicle and suppression of follicular growth in heifers," Anim Reprod Sci. 30:259-71 (1993).
Mihm et al., "Mechanisms for dominant follicle selection in monovulatory species: a comparison of morphological, endocrine and intraovarian events in cows, mares and women," Reprod Dom Anim. 43(Suppl 2):48-56 (2008).
Kudoh et al., "Inhibitory effect of a novel non-steroidal aromatase inhibitor, YM511 on the proliferation of MCF-7 human breast cancer cell," J Steroid Biochem Molec Biol. 58(2):189-94 (1996).
Yapura et al., "Effects of a single dose of a nonsteroidal aromatase inhibitor on ovarian function in cattle," Reprod Fertil Dev. 22(1):271 (2010).
International Search Report and Written Opinion for International Patent Application No. PCT/CA2014/050390, dated Jul. 22, 2014 (12 pages).
International Preliminary Report on Patentability for International Patent Application No. PCT/CA2014/050390, dated Oct. 29, 2015 (8 pages).
Bo et al., "Local versus systemic effects of exogenous estradio1-17 beta on ovarian follicular dynamics in heifers with progestogen implants," Anim Reprod Sci. 59(3-4):141-157 (2000).
Office Action for Canadian Patent Application No. 2837494, dated Nov. 6, 2017 (3 pages).
FEMA Drug Approval Package dated Jul. 25, 1997. pp. 1-276 (Part 1).
FEMA Drug Approval Package dated Jul. 25, 1997. pp. 276-551 (Part 2).
Health Canada. Drugs and Health Products. Veterinary Products. Questions and answers—Hormonal growth promoters. Accessed Jan. 25, 2009 [online]. Retrieved from the Internet: URL: http://www.hc-sc.gc.ca/dhp-mps/vet/faq/growth.sub.hormones.sub.promoters.sub.croissance.sub.hormonaux.sub.stimulateurs-eng.php (3 pages).
Mapletoft et al., "The use of controlled internal drug release devices for the regulation of bovine reproduction," J Anim Sci. 81(14 suppl 2):E28-E36 (2003).
Narendranath et al., "Acetic acid and lactic acid inhibition of growth of saccharomyces cerevisiae by different mechanisms," J Am Soc Brew Chem. 59(4):187-194 (2001).
US Food and Drug Administration. Compliance Policy Guides Manual, Sec. 608.400. "Compounding of drugs for use in animals". Department of Health and Human Services. (2003) (7 pages).
Yapura, Maria, Thesis: "Effects of a non-steroidal aromatase inhibitor on ovarian function in cattle," Master of Science, Dept Veterinary Biomedical Sci, Univ Saskatchewan, 2009.
Yapura et al., "Effects of a three-day regimen of letrozole on ovarian function in a bovine model," Proc Ann Meeting Can Fertil Androl Soc, Sep. 29-Oct. 2, Vancouver, BC (2010) (Abstract only) (1 page).

\* cited by examiner

AROMATASE INHIBITOR-RELEASING INTRAVAGINAL DEVICE

CROSS REFERENCE TO RELATED APPLICATIONS

This application claim priority to U.S. 61/813,967, filed on Apr. 19, 2013, the entire contents of which is incorporated herein by reference.

FIELD

The field of the invention generally relates to compounds, compositions, methods, and devices, for providing circulating plasma concentrations of an aromatase inhibitor in a mammal.

BACKGROUND

Control of the estrous cycle in mammalian species of commercial interest, such as cattle, has a great impact on the efficiency of meat and milk production. Numerous treatments and protocols have been successful in achieving the goal of timely control of the occurrence of several reproductive events such as luteolysis, estrus and ovulation (Kim, Suh et al., 2005; Martinez, Kastelic et al., 2007; Harper, Bennett et al., 2008). However, the application of many of these protocols involves the administration of hormonal combinations in food producing animals, many of which are perceived as having a negative impact on consumer health (Daxenberger, Ibarreta et al., 2001; Galbraith, 2002; Kolok & Sellin, 2008). The situation has led to the legal banning of steroid hormones within particular geographic locations (i.e., European Union, New Zealand, and Australia) or physiological categories of animals (i.e., lactating dairy cattle; (Official Journal of the European Union; Lane, Austin et al., 2008)).

Aromatase inhibitors are compounds that prevent the body from producing estradiol by inhibiting the activity of the aromatase enzyme that is responsible for the conversion of androgens into estrogens (Buzdar, Robertson et al., 2002; Buzdar, 2003). Aromatase inhibitors are used widely for the treatment of estrogen-responsive breast cancer in postmenopausal women (Beatson, 1983; Geisler, Haynes et al., 2002).

Recent studies have revealed the potential of aromatase inhibitors as a tool to control the estrous cycle in cattle (Yapura et al., 2011a; Yapura et al., 2011; Yapura et al., 2011b; Yapura et al., 2011c). These studies have focused on the use of letrozole, which has been the compound of choice for treatment of sub-fertility or infertility in women (Requena, Herrero et al., 2008). Letrozole treatment in cattle extended the lifespan of the dominant follicle, delayed the emergence of the next ovarian follicular wave, and altered the timing of ovulation. Letrozole treatment also had a consistent luteotrophic effect; i.e., development of a larger corpus luteum that produced more progesterone The intravaginal route of administration of letrozole is of particular interest because it allows for extended treatment protocols, it is minimally invasive for the animal, it reduces animal handling and treatment-associated stress, and is most likely to be accepted by practitioners and producers.

It is desirable to develop compounds, compositions, methods and devices, which provide an extended release of an aromatase inhibitor(s).

This background information is provided for the purpose of making known information believed by the applicant to be of possible relevance to the present invention. No admission is necessarily intended, nor should it be construed, that any of the preceding information constitutes prior art against the present invention.

SUMMARY

In accordance with one aspect of the present invention, there is provided a delivery vehicle for the delivery of an aromatase inhibitor to a mammal, said vehicle comprising: a wax delivery system; and an aromatase inhibitor; wherein said vehicle is suitable for delivering said aromatase inhibitor to the plasma of said subject.

In one example, said aromatase inhibitor is letrozole or anastrozole.

In one example, said device comprising: letrozole; at least one phospholipid, selected from PC, PA, PG, PE, PS, sterylamine, cationic lipids, anionic lipids, neutral lipids, zwitterionic lipids, tissue derived phosphatidylcholine, phosphatidylinositol, lactosylceramide, galactose cerebroside, gangliosides, lipids having periodate-oxidazable components containing vicinal hydroxyls, glycolipids, DPPC, DSPC, DMPC, DPPG, DPPQ, DSPG, DMPG, DPPA; DMPA, DSPA, DPPS, DMPS, DSPS, DPPE, DMPE, DSPE, EPC, EPG, EPI, EPS, EPE, EPA; SPC; SPG, SPS, SPI, SPE, SPA; HEPC, HSPC, DSPQ, DOPE, PSPC, PSPG, MOPE, or di-oleyl phosphytidyl ethanolamine; cholesterol; and a wax.

In one example, said device comprising: letrozole; at least one phospholipid selected from DPPC, DMPC, DPPE, egg yolk lecithin, or soy-bean lecithin; cholesterol; and a wax.

In one example, said device comprising letrozole; hydrogenated soy-bean phospholipid; di-oleyl phosphytidyl ethanolamine; cholesterol; and synthetic hydrogenated oil.

In one example, said device comprising (w/w): about 5%—about 20% letrozole, about 5%—about 20% hydrogenated soy-bean phospholipid; about 0.5%—about 5% di-oleyl phosphytidyl ethanolamine; about 0.5%—about 5% cholesterol; and synthetic hydrogenated oil q.s. to 100%.

In one example, said device comprising (w/w), about 10% letrozole; about 10% PC; about 2% DOPE; about 5% cholesterol; and synthetic hydrogenated oil p.s. to 100%.

In one example, said vehicle further comprises a gel coat.

In one example, said gel coat comprises, an aromatase inhibitor; gelatin; 65% polymer; and distilled water.

In one example, said gel coat comprises, letrozole, gelatin, a polymer, and distilled water.

In one example, said polymer comprises poloxamer 188 and/or poloxamer 407.

In one example, said gel coat comprising, 10% letrozole, 20% gelatin, 65% polymer, distilled water qs to 100%.

In one example, said 20% gelatin is obtained by hydrating 12% poloxamer 188 and 20% poloxamer 407, with 68% distilled water.

In another aspect of the present invention, there is provided a delivery vehicle for the delivery of an aromatase inhibitor to a subject vehicle for the delivery of an aromatase inhibitor to a subject, said vehicle comprising: a liposome delivery vehicle; and an aromatase inhibitor; wherein said vehicle is suitable for delivering said aromatase inhibitor to the plasma of said subject.

In one example, said aromatase inhibitor is letrozole or anastrozole.

In one example, said device comprising, letrozole; at least one phospholipid, selected from PC, PA, PG, PE, PS, sterylamine, cationic lipids, anionic lipids, neutral lipids, zwitterionic lipids, tissue derived phosphatidylcholine, phosphatidylinositol, lactosylceramide, galactose cerebroside, gangliosides, lipids having periodate-oxidazable components containing vicinal hydroxyls, glycolipids, DPPC, DSPC, DMPC, DPPG, DPPQ, DSPG, DMPG, DPPA; DMPA, DSPA, DPPS, DMPS, DSPS, DPPE, DMPE, DSPE, EPC, EPG, EPI, EPS, EPE, EPA; SPC; SPG, SPS, SPI, SPE, SPA; HEPC, HSPC, DSPQ, DOPE, PSPC, PSPG, MOPE, or di-oleyl phosphytidyl ethanolamine; and propylene glycol.

In one example, said device comprising comprising letrozole; PC; DOPE; cholesterol; and propylene glycol.

In one example, said device comprising (w/w): about 5%—about 20% letrozole, about 5%—about 20% hydrogenated soy-bean phospholipid; about 0.5%—about 5% dioleyl phosphytidyl ethanolamine; about 0.5%—about 5% cholesterol; or comprising (w/w), about 10% letrozole; about 10% PC, about 2% DOPE, about 5% cholesterol; about 20% propylene glycol; and water q.s. to 100%.

In another aspect of the present invention, there is provided a method of providing an aromatase inhibitor to the plasma of a subject, comprising: vaginal administration of a vehicle according as described above and herein.

In one example, said aromatase inhibitor is letrozole.

In one example, said letrozole circulates the plasma of said subject at least four days, about four or more days, about 1, 2, 3, 4, 5, 6, 7, 8, 9, 10, 11, 12, 13, or 14 days.

In one example, wherein said subject is a mammal.

In one example, said subject is a human; a non-human primate; a companion animal, including a dog or a cat; livestock, including a cow, a horse, a pig, sheep, deer, bison, or a buffalo; a wild animal, including a bovid, a cervid, a pinniped, a fetid, a canid; a heifer; a dairy cow; a beef cattle; Equidae, such as a horse.

In another aspect of the present invention, there is provided a method of synchronizing ovulation in a mammal, comprising: administering a delivery vehicle as described herein and above, to said mammal so as to induce the formation of a persistent follicle and delay wave emergence by preventing spontaneous ovulation in said mammal; administering a luteolytic dose of a prostaglandin so as to induce regression of the corpus luteum of said mammal; and administering an ovulatory does of GnRH or pLH to said mammal.

In one example, said aromatase inhibitor is a steroidal aromatase inhibitor or a non-steroidal aromatase inhibitor.

In one example, said non-steroidal aromatase inhibitor is letrozole, fadrozole or anastrozole.

In one example, said non-steroidal aromatase inhibitor is letrozole.

In one example, said prostaglandin is PGF.

In one example, said PGF is administered five days after administration of said aromatase inhibitor.

In one example, said GnRH or pLH is administered seven days after administration of said aromatase inhibitor.

In one example, insemination is suitable at estrus in said mammal or 6 to 7 days following treatment with GnRH or pLH.

In one example, said insemination is artificial insemination.

In one example, said mammal subject is a human; a non-human primate; a companion animal, including a dog or a cat; livestock, including a cow, a horse, a pig, sheep, deer, bison, or a buffalo; a wild animal, including a bovid, a cervid, a pinniped, a felid, a canid; a heifer; a dairy cow; a beef cattle; Equidae, such as a horse.

In one example, said mammal is a heifer, a dairy cow, a beef cattle, a sheep.

In one example, said administration of said delivery vehicle is administered intravaginally.

In another aspect of the present invention, there is provided a method of synchronizing ovulation a mammal, comprising: administering an effective amount of a prostaglandin; administering a delivery vehicle as described above and herein.

In one example, said prostaglandin is PGF.

In one example, said PGF is Lutalyse®.

In one example, said aromatase inhibitor is a non-steroidal inhibitor or a steroidal inhibitor.

In one example, said non-steroidal aromatase inhibitor is letrozole, fadrozole or anastrozole.

In one example, said non-steroidal aromatase inhibitor is letrozole.

In one example, said delivery vehicle is administered about 48 hours following administration said PGF.

In one example, said delivery vehicle is administered intravaginally.

In one example, said mammal is suitable for insemination, preferably artificial insemination.

In one example, said mammal is a human; a non-human primate; a companion animal, including a dog or a cat; livestock, including a cow, a horse, a pig, sheep, deer, bison, or a buffalo; a wild animal, including a bovid, a cervid, a pinniped, a felid, a canid; a heifer; a dairy cow; a beef cattle; Equidae, such as a horse.

In one example, said mammal is a heifer, a dairy cow, a beef cattle, or a sheep.

In another aspect of the present invention, there is provided a method of inducing superovulation in a mammal, comprising: administering a delivery vehicle, as described above and herein, to said mammal at the beginning of a follicular wave emergence in said mammal.

In one example, said aromatase inhibitor is letrozole, fadrozole or anastrozole.

In one example, wherein said aromatase inhibitor is letrozole.

In one example, said mammal is a human; a non-human primate; a companion animal, including a dog or a cat; livestock, including a cow, a horse, a pig, sheep, deer, bison, or a buffalo; a wild animal, including a bovid, a cervid, a pinniped, a felid, a canid; a heifer; a dairy cow; a beef cattle; Equidae, such as a horse.

In one example, said administration is intravaginal administration.

In another aspect of the present invention, there is provided a method of improving fertility in a mammal, comprising: administering a delivery vehicle, as described above and herein, to said mammal in early esterus or mid-diestrus following insemination of said mammal.

In one example, said aromatase inhibitor is a non-steroidal aromatase inhibitor.

In one example, said non-steroidal inhibitor is letrozole, fadrozole or anastrozole.

In one example, said non-steroidal inhibitor is letrozole.

In one example, said mammal is human; a non-human primate; a companion animal, including a dog or a cat; livestock, including a cow, a horse, a pig, sheep, deer, bison, or a buffalo; a wild animal, including a bovid, a cervid, a pinniped, a felid, a canid; a heifer; a dairy cow; a beef cattle; Equidae, such as a horse.

In one example, said bovid is a cow

In one example, said administration is intravaginal administration.

In another aspect of the present invention, there is provided, a method of inducing double ovulation in a mammal, comprising: administering a delivery, as described above and herein, to said mammal from day 1 to day 7 following follicular wave emergence in said mammal.

In one example, said aromatase inhibitor is a non-steroidal aromatase inhibitor.

In one example, said non-steroidal aromatase inhibitor is letrozole, fadrozole, or anastrozole.

In one example, said non-steroidal aromatase inhibitor is leterozole,

In one example, further comprising administration of PGF on day five following follicular wave emergence, In one example, further comprising administration of GnRH/LH treatment about 36 hours after administration of PGF.

In one example, said administration is intravaginal administration.

In one example, wherein said mammal is a human; a non-human primate; a companion animal, including a dog or a cat; livestock, including a cow, a horse, a pig, sheep, deer, bison, or a buffalo; a wild animal, including a bovid, a cervid, a pinniped, a felid, a canid; a heifer; a dairy cow; a beef cattle; Equidae, such as a horse.

In one example, said bovid is a cow.

In another aspect of the present invention, there is provided a method of improving twinning in a mammal, comprising: administering a delivery vehicle according to any one of claims 1-18 to said mammal before dominant follicle selection; administering a luteolytic dose of a prostaglandin.

In one example, said aromatase inhibitor is administered on the day of or the day after follicle wave emergence of either an anovulatory or ovulatory follicular wave.

In one example, said aromatase inhibitor is a non-steroidal aromatase inhibitor, In one example, said non-steroidal aromatase inhibitor is letrozole, fadrozole, or anastrozole.

In one example, said non-steroidal aromatase inhibitor is letrozole.

In one example, said prostaglandin is PGF.

In one example, said mammal is suitable for insemination, preferably artificial insemination, on day 6 or 7 after follicular wave emergence.

In one example, said mammal is a human; a non-human primate; a companion animal, including a dog or a cat; livestock, including a cow, a horse, a pig, sheep, deer, bison, or a buffalo; a wild animal, including a bovid, a cervid, a pinniped, a felid, a canid; a heifer; a dairy cow; a beef cattle; Equidae, such as a horse.

In one example, said mammal is a cow.

In accordance with another aspect of the present invention, there is provided use of a delivery vehicle, as described above and herein, in a mammal so as to induce the formation of a persistent follicle and delay wave emergence by preventing spontaneous ovulation in said mammal; use of a luteolytic dose of a prostaglandin so as to induce regression of the corpus luteum of said mammal; and use for an ovulatory does of GnRH or pLH in said mammal for synchronizing ovulation in said mammal, wherein said mammal synchronized for ovulation is suitable for insemination.

In one example, said aromatase inhibitor is a steroidal aromatase inhibitor or a non-steroidal aromatase inhibitor.

In one example, said non-steroidal aromatase inhibitor is letrozole, fadrozole or anastrozole.

In one example, said non-steroidal aromatase inhibitor is letrozole.

In one example, said prostaglandin is PGF.

In one example, said PGF is suitable for administration five days after administration of said aromatase inhibitor.

In one example, said GnRH or pLH is suitable for administration seven days after administration of said aromatase inhibitor.

In one example, said insemination occurs at estrus in said mammal or 6 to 7 days following treatment with GnRH or pLH.

In one example, said insemination is artificial insemination.

In one example, said mammal is a human; a non-human primate; a companion animal, including a dog or a cat; livestock, including a cow, a horse, a pig, sheep, deer, bison, or a buffalo; a wild animal, including a bovid, a cervid, a pinniped, a felid, a canid; a heifer; a dairy cow; a beef cattle; Equidae, such as a horse.

In one example, said mammal is a heifer, a dairy cow, or a beef cattle.

In one example, said administration of said aromatase inhibitor is suitable for intravaginal administration.

In accordance with another aspect of the present invention, there is provided use of a prostaglandin; and use of a delivery vehicle, as described above and herein, for synchronizing ovulation in a mammal, wherein said mammal synchronized for ovulation is suitable for insemination.

In one example, said prostaglandin is PGF.

In one example, said PGF is Lutalyse®.

In one example, said aromatase inhibitor is a non-steroidal inhibitor or a steroidal inhibitor.

In one example, said non-steroidal aromatase inhibitor is letrozole, fadrozole or anastrozole.

In one example, said non-steroidal aromatase inhibitor is letrozole.

In one example, said letrozole is suitable for administration about 48 hours following administration said PGF.

In one example, said administration is intravaginal administration.

In one example, said insemination is artificial insemination.

In one example, said mammal is a human; a non-human primate; a companion animal, including a dog or a cat; livestock, including a cow, a horse, a pig, sheep, deer, bison, or a buffalo; a wild animal, including a bovid, a cervid, a pinniped, a felid, a canid; a heifer; a dairy cow; a beef cattle; Equidae, such as a horse, In one example, said mammal is a heifer, a dairy cow, or a beef cattle.

In accordance with another aspect of the present invention, there is provided use of a delivery vehicle according to any one of claims 1-18 in a mammal at the beginning of a follicular wave emergence in said mammal for inducing superovulation in a mammal.

In one example, said aromatase inhibitor is letrozole, fadrozole or anastrozole.

In one example, said aromatase inhibitor is letrozole.

In one example, said administration is intravaginal administration.

In one example, said mammal is a human; a non-human primate; a companion animal, including a dog or a cat; livestock, including a cow, a horse, a pig, sheep, deer, bison, or a buffalo; a wild animal, including a bovid, a cervid, a pinniped, a felid, a canid; a heifer; a dairy cow; a beef cattle; Equidae, such as a horse.

In accordance within another aspect of the present invention, there is provided use of a delivery vehicle, as described above and herein, in a mammal early esterus or mid-diestrus following insemination of said mammal for improving fertility in said mammal.

In one example, said aromatase inhibitor is a non-steroidal aromatase inhibitor.

In one example, said non-steroidal inhibitor is letrozole, fadrozole or anastrozole.

In one example, said non-steroidal inhibitor is letrozole.

In one example, administration is intravaginal administration.

In one example, said mammal is a human; a non-human primate; a companion animal, including a dog or a cat; livestock, including a cow, a horse, a pig, sheep, deer, bison, or a buffalo; a wild animal, including a bovid, a cervid, a pinniped, a felid, a canid; a heifer; a dairy cow; a beef cattle; Equidae, such as a horse.

In one example, said mammal is a cow.

In another aspect of the present invention there is provided use of a delivery vehicle according, as described above and herein, in a mammal from day 1 to day 7 following follicular wave emergence in said mammal for inducing double ovulation in said mammal.

In one example, said aromatase inhibitor is a non-steroidal aromatase inhibitor.

In one example, said non-steroidal aromatase inhibitor is letrozole, fadrozole, or anastrozole.

In one example, said non-steroidal aromatase inhibitor is leterozole.

In one example, administration is intravaginal administration.

In one example, further comprising use of PGF on day five following follicular wave emergence.

In one example, further comprising use of GnRH/LH treatment about 36 hours after administration of PGF.

In one example, said mammal is a human; a non-human primate; a companion animal, including a dog or a cat; livestock, including a cow, a horse, a pig, sheep, deer, bison, or a buffalo; a wild animal, including a bovid, a cervid, a pinniped, a felid, a canid; a heifer; a dairy cow; a beef cattle; Equidae, such as a horse.

In one example, said mammal is a cow.

In accordance with another aspect of the present invention, there is provided use of a delivery vehicle, as described above and herein, in a mammal before dominant follicle selection; and use of a luteolytic dose of a prostaglandin for improving twinning in said mammal, wherein said mammal is suitable for inseminating.

In one example, said aromatase inhibitor is suitable for administration on the day of or the day after follicle wave emergence of either an anovulatory or ovulatory follicular wave.

In one example, said aromatase inhibitor is a non-steroidal aromatase inhibitor.

In one example, said non-steroidal aromatase inhibitor is letrozole, fadrozole, or anastrozole, In one example, said non-steroidal aromatase inhibitor is letrozole.

In one example, said prostaglandin is PGF.

In one example, said insemination is artificial insemination on day 6 or 7 after follicular wave emergence.

In one example, said mammal is a human; a non-human primate; a companion animal, including a dog or a cat; livestock, including a cow, a horse, a pig, sheep, deer, bison, or a buffalo; a wild animal, including a bovid, a cervid, a pinniped, a felid, a canid; a heifer; a dairy cow; a beef cattle; Equidae, such as a horse.

In one example, said mammal is a cow.

In another aspect of the present invention, there is provided a kit for providing an aromatase inhibitor in the plasma of a mammal, comprising: a delivery vehicle, as described above and herein, and instructions for the method and use as described above and herein.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1A:
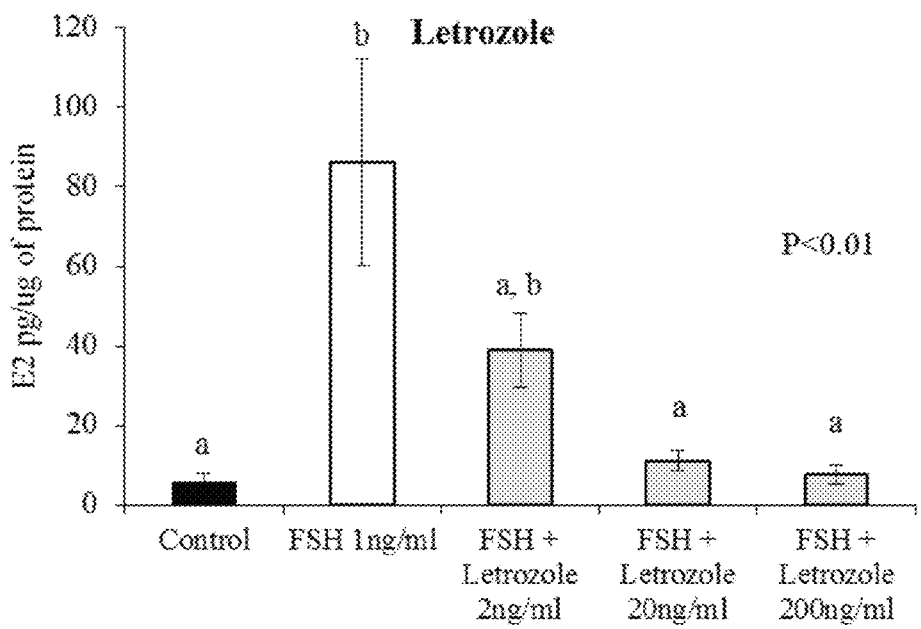
FIGS. 1A, 1B, and 1C are bar graphs depicting the effect of three different inhibitors of estradiol production on estradiol secretion by bovine granulosa cells in culture. Cells were cultured in vitro for 6 days under non-luteinising conditions without treatment (negative control), or treatment with FSH alone (positive control) or with letrozole (FIG. 1A), anastrozole (FIG. 1B) or fenbendazole (FIG. 1C) at 1/10× standard, standard or 10× standard doses. Data are presented as the mean±SEM estradiol concentrations in three independent replicate cultures for each inhibitor. $^{ab}$Values with no common superscript are different (P<0.05)

In one embodiment, described herein is are aromatase inhibitor compound(s), a pharmaceutical composition(s) comprising the aromatase inhibitor compound(s), delivery device(s)/vehicles and the use of such aromatase inhibitor compound(s), a pharmaceutical composition(s) comprising the aromatase inhibitor compound(s) and delivery device(s)/vehicles in a subject to provide circulating plasma concentrations of the aromatase inhibitor in a subject, as will be described in more detail below.

Such compound(s), pharmaceutical composition(s) and device(s) are suitable for use in the control of estrus in a subject, such as a mammal, synchronizing estrous and ovulation (for example in an individual mammal or a plurality of mammals), timed artificial insemination in a mammal, embryo transfer donor and recipient synchronization prior to superstimulation treatment in a mammal, twinning in a mammal, and increase post-artificial insemination and post-embryo transfer fertility in a mammal. The application of such compound(s), pharmaceutical composition(s), method(s) and device(s) are more fully described in WO 2011/143752 and U.S. Ser. No. 13/698,402 the contents of which are hereby incorporated by reference in their entirety In some examples, the aromatase inhibitor is circulating in plasma of a subject at least four days. In another example, the aromatase inhibitor is circulating in plasma about four or more days. In specific example, the aromatase inhibitor is circulating in plasma at least about 1, 2, 3, 4, 5, 6, 7, 8, 9, 10, 11, 12, 13, or 14 days.

The compound(s), pharmaceutical composition(s) and device(s), and methods of the present invention are suitable for use in female subjects. In a specific example, the subject is a mammal.

In some examples, mammals include humans, non-human primates, companion animals (such as dogs, cats, and the like), livestock (such as cows, horses, pigs, sheep, deer, bison, buffalo, and the like) or wild animals (such as bovids, cervids, pinnipeds, felids, canids, and the like). Mammals may be individual or in a herd A herd generally refers to at least two (or two or more) individual mammals. A heard may also be referred to as a group, or a plurality.

In a specific embodiment, methods of the present invention are suitable for use in bovids, including heifers, dairy cows, and beef cattle. In some examples, there compound(s), composition(s), method(s) and device(s) of the present invention are suitable for use in a herd or group of bovids.

In another specific embodiment, methods of the present invention are suitable for use in Equidae, including horses.

Aromatase Inhibitors

Estrogens have been used by the beef industry as growth promoters, in part because of the role they play in other important physiological functions in vertebrates such as determination of secondary sexual characteristics, linear growth and closure of epiphyseal plates, and fat deposition. However, use of natural or synthetic estrogens directly in food producing animals is increasingly undesirable.

Estrogens are produced by the conversion of androgen through the enzymatic activity of aromatase.

In some examples, the suppression of estrogen biosynthesis can be achieved by inhibiting the aromatase enzyme.

The term "aromatase inhibitor", as used herein, relates to a compound which inhibits estrogen production, i.e., the conversion of the substrates androstenedione and testosterone to estrone and estradiol, respectively. Thus, in some example, "aromatase inhibitor" refers to substances that inhibit the enzyme aromatase (estrogen synthetase), which is responsible for converting androgens to estrogens.

The term "inhibit" or "inhibitor" as used herein, refers to any method or technique which inhibits protein synthesis, levels, activity, or function, as well as methods of inhibiting the induction or stimulation of synthesis, levels, activity, or function of the protein of interest, for example aromatase. The term also refers to any metabolic or regulatory pathway which can regulate the synthesis, levels, activity, or function of the protein of interest. The term includes binding with other molecules and complex formation. Therefore, the term "inhibitor" refers to any agent or compound, the application of which results in the inhibition of protein function or protein pathway function. However, the term does not imply that each and every one of these functions must be inhibited at the same time.

In some examples, aromatase inhibitors have been classified as first-, second- and third-generation inhibitors according to the chronologic order of their clinical development and as type 1 or type 2 inhibitors according to their mechanism of action. Type 1 aromatase inhibitors are generally steroidal analogues of androstenedione that bind irreversibly to aromatase (noncompetitive, irreversible), thereby inactivating the enzyme. Type 2 aromatase inhibitors are generally nonsteroidal and bind reversibly to the heme group of the enzyme by way of a basic nitrogen (competitive, reversible),In some examples, aromatase inhibitors known in the art are suitable for practicing the present invention.

Aromatase inhibitors may have a non-steroidal or a steroidal chemical structure.

In one aspect of the present invention, the aromatase inhibitor used is a non-steroidal aromatase inhibitor. Examples of non-steroidal aromatase inhibitors include letrozole, fadrozole and anastrozole, The term "non-steroidal aromatase inhibitor" as used herein refers to both a single non-steroidal aromatase inhibitor or a mixture of more than one non-steroidal aromatase inhibitor.

In one example, a benzimidazole (fenbendazole) was also tested herein. The commonly used anthelmintic, fenbendazole, was tested as a possible estradiol inhibitor based on reports that benzimidazole drugs have mild anti-estrogenic effects in mammals and may disturb reproductive events (Kragie, Turner et al., 2002; Johnston, Bieszczak et al., 2006), and that deworming treatment with another benzimidazole (albendazole) in ewes resulted in decreased estradiol concentrations in follicular fluid (Mamali, Samartzi et al., 2008).

In some examples, the aromatase inhibitor is commercially available, either as a pure compound or in the form of a pharmaceutical composition, In some examples aromatase inhibitors include, but are not limited to anastrozole, letrozole, exemestane, fadrozole, anastrozole, atamestane, formestane, and finrozole.

In one example, exemestane (6-methylene-androsta-I,4-diene-3,17-dione) is available under the trade name Aromasin® and is a steroidal aromatase inhibitor.

In one example, anastrozole is available under the trademark Arimidex®. Anastrozole is a nonsteroidal aromatase inhibitor.

In one example, letrozole is available under the trademark Fernarae. Letrozole is a nonsteroidal aromatase inhibitor.

Other examples include atamestane (I-methyl-androsta-I, 4-diene-3,17-dione), formestane(4-hydroxy-4-androsten-3, 17-dione) and its 4-(C2-Ci2)acyloxy derivative, fadrozole, and finrozole.

In another example, the present invention is not limited to the use of the specific aromatase inhibitors named herein; the preparation of other aromatase inhibitors will be apparent to one skilled in the art based on the literature.

In a preferred example, the aromatase inhibitor is letrozole.

In some examples said aromatase inhibitor comprises, an RNA interference molecule, a small molecule, nucleic acid, an antibody, a peptide, a pharmaceutical composition, an aptamers, or combinations thereof. In some examples said RNA interference molecule comprises a RNAi molecule, a siRNA molecule, or a shRNA molecule.

In a specific aspect, said antibody is a monoclonal antibody or a polyclonal antibody. In a specific aspect, said nucleic acid comprises a dsRNA molecule, a RNAi molecule, miRNA molecule, a ribozyme, a shRNA molecule, or a siRNA molecule.

In some examples, the aromatase inhibitor circulates in the plasma of a subject at least four days. In another example, the aromatase inhibitor circulates in the plasma of a subject about four or more days. In specific example, the aromatase inhibitor circulates in the plasma of a subject at least about 1, 2, 3, 4, 5, 6, 7, 8, 9, 10, 11, 12, 13, or 14 days.

Prostaglandin, Gonadotropin Releasing Hormone

The methods of the present invention include compounds that have been used in artificial insemination protocols in cattle, including gonadotropin-releasing hormone, progesterone, melengestrol, prostaglandin F2α (dinoprost, PGF) and cloprostenol.

A summary of drug products approved in the USA for synchronization of estrous in cattle are as follows;

| Active or co-active ingredient | Number of products approved |
|---|---|
| Cloprostenol Sodium | 2 |
| Progesterone | 2 |
| Melengestrol Acetate | 6 |
| Dinoprost Tromethamine | 3 |
| Norgestomet | 1 |
| Estradiol Valerate | 1 |

Gonadotropin releasing hormone (GnRH), is a decapeptide that is secreted by the hypothalamus into the hypophyseal portal circulation in response to neural and/or chemical stimuli, causing the biosynthesis and release of luteinizing hormone (LH) and follicle-stimulating hormone (FSH) by the pituitary. GnRH is also known as gonadoliberin, LH releasing hormone (LHRH), FSH releasing hormone (FSHRH) and LH/FSH releasing factor (LH/FSHRF).

Prostaglandins are generally characterised by the substituents on the cyclopentyl ring. The 2α prostaglandins and prostaglandin analogues generally have two hydroxyl groups in a cis configuration relative to the cyclopentane ring, and two side chains in a trans configuration relative to each other, each side chain having one double bond. Analogues of PGF2α can have a different number of double bonds in the side chains, and the substituents along the side chains may vary. Additionally, in some PGF2α analogues, the side chain carboxylic acid group may be esterified.

Additional analogues of prostaglandin F2α. include fenprostalene ((.+-.)-9α11α15α-trihydroxy-16-phenoxy-17, 18,19,20-tet ranorprosta-4,5,13-trans-trienoic acid methyl ester); cloprostenol (7-[2-[4-(3-chlorophenoxy)-3-hydroxy-1-butenyl]-3,5-dihydroxycyclopentyl]-5-heptenoic acid), an aryloxymethyl analog of prostaglandin F2α; fluprostenol (9,11,15-trihydroxy-15-methylprosta-4,5,13-trien-1-oic acid methyl ester; prostalene (7-[3-hydroxy-2-(3-hydroxy-1-octenyl)-5-oxocyclopentyl]-5-heptenoic acid); alfaprostol ([1R-[1.alpha.(Z), 2 (S*), 3,5α]]-7-[2-(5-cyclohexyl-3-hydroxy-1-pentynyl)-3,5-dihydroxycyclopentyl]-5-heptenoic acid methyl ester); and the pharmaceutically acceptable salts of prostaglandin, e.g., the tromethamine salt of prostaglandin F2α. (dinoprost tromethamine), and its analogs. The pharmaceutically acceptable salts thereof include, but are not limited to, the addition salts of inorganic and organic acids, which are commercially available, such as the tromethamine and sodium salts.

A specific example of the present invention, the analogue of prostaglandin is cloprostenol.

As used herein, the term "prostaglandin" refers to any prostaglandin or prostaglandin analog, which is either naturally occurring or synthetically produced, and which has and/or exerts the desired characteristic in use.

Aromatase Inhibitor Delivery Vehicle

In one embodiment, the aromatase inhibitor(s) of the present invention is/are formulated within a delivery vehicle.

In some examples a delivery vehicle comprises lipid-based delivery vehicle, such as a liposome (or liposomal)

delivery vehicle. In some examples a delivery vehicle comprises a wax delivery vehicle.

Liposomes

Liposomes are microscopic vesicles that comprise of one or more lipid bilayers, typically surrounding an aqueous compartment. Because liposome can be formulated with bulk lipid molecules that are also found in natural cellular membranes, liposome generally can be administered safely and are biodegradable. Thus, liposome are often used in drug delivery.

Depending on the method of preparation, liposomes may be unilamellar or multilamellar, and can vary in size with diameters ranging from about 0.02 um to greater than about 10 um. A variety of agents may be encapsulated in or inserted into liposomes. Hydrophobic agents partition in the bilayers and hydrophilic agents partition within aqueous space(s).

In some examples, liposomes are used as delivery vehicles of aromatase inhibitors. Exemplary liposomes that may be used in the method of the present invention include multilamellar vesicles (MLV), oligolamellar vesicles (OLV), unilamellar vericles (UV), small unilamellar vesicles (SUV), medium-sized unilamellar vesicles (MUV), large unilamellar vesicles (LUV), giant unilamellar vesicles (GUV), multivesicular vesicels (MW), single or oligolamellar vesicles made by reverse-phase evaporation method (REV), multilamellar vesicles made by reverse-phase evaporation method (MLV-REV), stable plurilamellar vesicles (SPLV), frozen and thawed MLV (FATMLV), vesicles prepared by extrusion methods (VET), vesicles prepared by French Press (FPV), vesicles prepared by fusion (FUV), dehydration-rehydration vesicles (DRV), and bubblecomes (BSV). However, as understood by one skilled in the art, the type of liposome is not meant to be limiting and may include any liposome made in any matter that is compatible with the methods of the invention.

Liposomes may be made with a variety of lipid components.

The term "lipid" as used herein means a substance that is soluble in organic solvents.

In some example, lipids may be anionic, cationic, neutral, or zwitterionic.

Non-limiting examples of lipids include phosphatidylcholine (PC), egg yolk lecithin, and soy-bean lecithin, phosphatidic acid (PA), phosphatidylglycerol (PG), phosphatidylethanolamine (PE), phosphatidylserine (PS), sterylamines, cationic lipids, tissue derived phosphatidylcholine, phosphatidylinositol, lactosylceramide, galactose cerebroside, gangliosides, lipids having periodate-oxidazable components containing vicinal hydroxyls, and glycolipids, dipalmitoylphosphatidylcholine (DPPC), distearoylphosphatidylcholine (DSPC), dimyristoylphosphatidylcholine (DMPC), dipalmitoylphosphatidylglycerol (DPPG), dipalmitoylphosphatidcholine (DPPQ) distearoylphosphatidylglycerol (DSPG), dimyristoylphosphatidylglycerol (DMPG), dipanitoylphosphatidic acid (DPPA); dimyristoylphosphatidic acid (DMPA), distearoylphosphatidic acid (DSPA), dipalmitoylphosphatidylserine (DPPS), dimyristoylphosphatidylserine (DMPS), distearoylphosphatidylserine (DSPS), dipalmitoylphosphatidylethanolamine (DPPE), dimyristoylphosphatidylethanolamine (DMPE), and distearoylphosphatidylethanolamine (DSPE).

Additional examples include, but are not limited to egg phosphatidylcholine (EPC), egg phosphatidylglycerol (EPG), egg phosphatidylinositol (EPI), egg phosphatidylserine (EPS), phosphatidylethanolamine (EPE), and phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the number 1 position of glycerol that include choline, glycerol, inositol, serine, ethanolamine, as well as the corresponding phosphatidic acids. The chains on these fatty acids can be saturated or unsaturated, and the phospholipid may be made up of fatty acids of different chain lengths and different degrees of unsaturation.

Additional examples include, but are not limited to, distearoylphosphatidylcholine (DSPQ), dioleylphosphatidyl-ethanolamine (DOPE) and mixed phospholipids like palmitoylstearoylphosphatidyl-choline (PSPC), and palmitoylstearolphosphatidylglycerol (PSPG), and single acylated phospholipids like mono-oleoyl-phosphatidylethanolamine (MOPE).

Lipids may be natural, synthetic, or semi-synthetic.

A liposome may contain one or more types of lipids.

In a specific example, a lipid is 1,2-Dioleoyl-sn-Glycero-3-Phosphoethanolamine (DOPE). In a specific example, a lipid is phosphatidylcholine (PC). In another specific example, the lipid is DOPE. In one example, the liposome comprises PC and DOPE.

In another example, the liposome comprises a sterol. The sterol can include, but is not limited to cholesterol, esters of cholesterol including cholesterol hemi-succinate, salts of cholesterol including cholesterol hydrogen sulfate and cholesterol sulfate, ergosterol, esters of ergosterol including ergosterol hemi-succinate, salts of ergosterol including ergosterol hydrogen sulfate and ergosterol sulfate, lanosterol, esters of lanosterol including lanosterol hemi-succinate, salts of lanosterol including lanosterol hydrogen sulfate and lanosterol sulfate. In a specific example, the sterol is cholesterol.

In one example, the liposome comprises PC, DOPE, and cholesterol.

Methods for preparing liposomes are known in the art.

For example, a lipid and optionally co-lipid can be emulsified by the use of a homogenizer, lyophilized, and melted to obtain multilamellar liposomes. Alternatively, unilamellar liposomes can be produced by reverse phase evaporation method. In some embodiments, the liposomes are produced using thin film hydration. In certain embodiments, the liposome formulation can be briefly sonicated and incubated at, for example, about 50° C. to about 60° C., for a short period of time (e.g., about 10 minutes).

In some embodiments, the prepared liposome can be sized wherein the liposomes are selected from a population of liposomes based on the size (e.g., diameter) of the liposomes. The liposomes can be sized using techniques such as ultrasonication, high-speed homogenization, and pressure filtration Sonicating a liposome either by bath or probe sonication produces a progressive size reduction down to small vesicles less than about 0.05 microns in size. Vesicles can be recirculated through a standard emulsion homogenizer to the desired size, typically between about 0.1 microns and about 0.5 microns. The size of the liposomes can be determined by quasi-elastic light scattering (QELS). The average diameter can be reduced by sonication of the liposomes. Intermittent sonication cycles can be alternated with QELS assessment to guide efficient liposome synthesis. Alternatively, liposomes can be extruded through a small-pore polycarbonate membrane or an asymmetric ceramic membrane to yield a well-defined size distribution. Typically, a suspension is cycled through the membrane one or more times until the desired size distribution is achieved. The complexes can be extruded through successively smaller-pore membranes, to achieve a gradual reduction in size.

In some example, the lipid-based delivery vehicle is an emulsion. An emulsion is a dispersion of one liquid in a second immiscible liquid. The term "immiscible" when referring to two liquids refers to the inability of these liquids to be mixed or blended into a homogeneous solution. Two immiscible liquids when added together will always form two separate phases. Emulsions are essentially swollen micelles, although not all micellar solutions can be swollen to form an emulsion. Micelles are colloidal aggregates of amphipathic molecules that are formed at a well-defined concentration known as the critical micelle In some examples, the lipid based delivery vehicle comprises micelles. Micelles are oriented with the hydrophobic portions of the lipid molecules at the interior of the micelle and the hydrophilic portions at the exterior surface, exposed to water. The typical number of aggregated molecules in a micelle (aggregation number) has a range from about 50 to about 100. The term "micelles" also refers to inverse or reverse micelles, which are formed in an organic solvent, wherein the hydrophobic portions are at the exterior surface, exposed to the organic solvent and the hydrophilic portion is oriented towards the interior of the micelle.

Lipid-based delivery vehicles, such as liposomes, may be formulated in a liquid or lyophilized formulation.

In some examples, the aromatase inhibitor may be associated with the lipid bilayer of the liposome that is formed upon rehydration.

In some examples, the liposome, hydrate or dehydrated, is provided in a unit dosage form, with one or more aromatase inhibitor.

Liposomes may also contain a pharmaceutically acceptable stabilizer and/or antioxidant depending on the administration route. Non-limiting examples of the stabilizer include sugars such as glycerol, mannitol, sorbitol, lactose, and sucrose. When a sterol such as cholesterol is used for the additional lipid constituent of the membrane, such sterol also acts as a stabilizer.

A liposome may also comprise a pharmaceutically acceptable additive, depending on the administration route. Examples of such additive include water, physiological saline, pharmaceutically acceptable organic solvent, collagen, polyvinyl alcohol, polyvinylpyrrolidone, carboxyvinyl polymer, sodium carboxymethyl cellulose, poly(sodium acrylate), sodium alginate, water soluble dextran, sodium carboxymethyl starch, pectin, methylcellulose, ethylcellulose, xanthan gum, gum arabic, casein, gelatin, agar, diglycerin, propylene glycol, polyethylene glycol, vaseline, paraffin, stearyl alcohol, stearic acid, human serum albumin (HSA), mannitol, sorbitol, lactose, PBS, in vivo degradable polymer, serum-free medium, pharmaceutically acceptable surfactant, and any combination thereof.

As noted above, in some examples, compounds and compositions of the present invention are formulated within a liposome(s). This is understood to encompass the example in which a compound or composition encapsulated within a closed space of the liposome; or the example in which a compound or composition is contained within the membrane(s) (or bilayer) of the liposome; or the example in which a compound or composition is on an exterior surface of the membrane; or combinations thereof.

In one example, the liposome delivery vehicle comprises PC, DOPE, cholesterol, and propylene glycol.

In one example, the liposome delivery vehicle comprises PC, DOPE, cholesterol, propylene glycol, and an aromatase inhibitor.

In one example, the liposome delivery vehicle comprises PC, DOPE, cholesterol, propylene glycol, and an aromatase inhibitor, wherein said aromatase inhibitor is letrozole.

In one example, the liposome delivery vehicle comprises (w/w) about 5—about 20% letrozole, about 5—about 20% hydrogenated soy-bean phospholipid; about 0.5—about 5% di-oleyl phosphytidyl ethanolamine; and about 0.5%—about 5% cholesterol.

A specific example of a liposome formulation, includes, but is not limited to: (% w/w): 10% letrozole (Xian Huayang Biological Science and Technology; Xian, China); 10% hydrogenated soy phosphatidylcholine (Phospholipon 90H; American Lecithin Company, Oxford, Conn., USA); 5% cholesterol (Spectrum Chemical and Laboratory Products, New Brunswick, N.J., USA); 2% 1,2-Dioleoyl-sn-Glycero-3-Phosphoethanolamine (DOPE, Avanti Polar Lipids Inc., Ala., Ala., USA); 20% propylene glycol and water qs to 100% (Foldvari, Badea et al.). The preparation is heated to 65° C. and vortexed to obtain a uniform mixture.

Waxes

Waxes provide sustained release of the drug from a matrix. They, include, but are not limited to waxes, fats, fatty substances, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and triglycerides), and hydrogenated fats. Specific examples include, but are not limited to hydrogenated vegetable oil, hydrogenated cottonseed oil, hydrogenated castor oil, hydrogenated palm oil, hydrogenated palm kernel, and hydrogenated coconut oils, stearic acid, cocoa butter, and stearyl alcohol. Suitable waxes and wax-like materials include natural or synthetic waxes, hydrocarbons, and normal waxes. Examples of waxes include base suppository waxes. Specific examples of waxes include beeswax, glycowax, castor wax, carnauba wax, paraffins and candelilla wax, jojoba wax and spermaceti.

As used herein, a wax-like material is defined as any material which is normally solid at room temperature and has a melting point of from about 30 to 300° C.

In a specific example, a wax includes hydrogenated vegetable oil. In one example, the was includes Suppocire®. In a more specific example, the wax includes Suppocire® D.

Rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropylcellulose, methylcellulose, and carboxymethyl-cellulose), alginic acid, lactose and talc. Additionally, a pharmaceutically acceptable surfactant (for example, lecithin) may be added to facilitate the degradation of such microparticles.

In one example, the wax delivery vehicle comprises PC, DOPE, cholesterol, and hydrogenated vegetable oil In one example, the wax delivery vehicle comprises PC, DOPE, cholesterol, and Suppocire.

In one example, the wax delivery vehicle comprises PC, DOPE, cholesterol, and hydrogenated vegetable oil, and an aromatase inhibitor.

In one example, the wax delivery vehicle comprises PC, DOPE, cholesterol, and Suppocire D, and an aromatase inhibitor.

In one example, the wax delivery vehicle comprises PC, DOPE, cholesterol, hydrogenated vegetable oil, and an aromatase inhibitor, wherein said aromatase inhibitor is letrozole.

In one example, the wax delivery vehicle comprises PC, DOPE, cholesterol, Suppocire D, and an aromatase inhibitor, wherein said aromatase inhibitor is letrozole.

In one example, the liposome delivery vehicle comprises (w/w) about 5—about 20%, about 5—about 20% hydrogenated soy-bean phospholipid; about 0.5—about 5% di-oleyl phosphytidyl ethanolamine; about 0.5%—about 5% cholesterol; and synthetic hydrogenated oil q.s. to 100%.

A specific example of a wax formulation, includes, but is not limited to: (% w/w): 10% letrozole; 10% Hydrogenated soy phosphatidylcholine (Phospholipon 90H; American Lecithin Company); 5% cholesterol; 2% DOPE; and Suppocire D (Gattefosse, Paris, France) q.s. to 100%. The preparation is heated to 65° C. and vortexed to obtain a uniform mixture.

Wax formulations and liposome may further comprise a gel coat.

A gel coat may comprise one or more materials that provide immediate release. Examples of suitable coating materials include, but are not limited to, gelatin, a polymer (for example, poloxamer a188 and poloxamer 407), cellulose derivatives (methylcellulose, propylcellulose, carboxymethylcellulose Na) and/or combinations thereof.

In one example, the gel coat comprises: an aromatase inhibitor, gelatin, 65% polymer, distilled water qs to 100%. In one example, said aromatase inhibitor is letrozole.

In one example, the gel coast does not include an aromatase inhibitor.

In one example, at least one aromatase inhibitor is incorporated in lipid and/or wax vehicles, which are dispersed in the gel coat, wherein the at least one aromatase inhibitor is not added to the gel coat In one example, at least one aromatase inhibitor is incorporated in lipid and/or wax vehicles, which are dispersed in the gel coat, wherein the at least one aromatase inhibitor is also added to the gel coat.

In one example, the gel coat comprises (all ingredients % w/w): letrozole, gelatin, 65% polymer (prepared by hydrating 12% poloxamer 188 and 20% poloxamer 407, with 68% distilled water), distilled water qs to 100%, In one example, the gel coat comprises (all ingredients % w/w): letrozole, gelatin, 65% polymer (prepared by hydrating about 10%—about 20% poloxamer 188 and about 10%—about 30% poloxamer 407, with about 50—about 80% distilled water), distilled water qs to 100%.

Additional specific examples of wax formulations include, but are not limited to, the following (all ingredients % w/w): 10% letrozole; 10% hydrogenated soy phosphatidylcholine; 5% cholesterol NF; 2% DOPE; and hydrogenated vegetable oil q.s. to 100%. The gel coat contained the following (all ingredients % w/w): 10% letrozole, 20% gelatin (Gelatin type B, Fisher Scientific, Pittsburgh, Pa., USA), 65% polymer (prepared by hydrating 12% Poloxamer 188 and 20% Poloxamer 407, both from Spectrum Chemical, New Brunswick, N.J., USA, with 68% distilled water), distilled water qs to 100%. The Wax+gel coat device was formulated similarly, except that DOPE was excluded from the formulation. The Wax device was 100% wax-based, and contained the following ingredients (% w/w): 10% letrozole; 10% Hydrogenated soy phosphatidylcholine (Phospholipon 90H; American Lecithin Company); 5% cholesterol; and hydrogenated vegetable oil (Suppocire D, Gattefosse) q.s. to 100%, Methods of Use The compound(s) and composition(s), pharmaceutically acceptable salts and prodrugs of the present invention are administered to an animal using a method that delivers a compound or composition systemically and/or locally.

Examples of methods of administration include parenteral administration, oral administration, topical administration, vaginal administration, and the like.

As used herein, "topical administration" includes cream, ointment or spray applied to the skin.

As used herein, the term "parenteral" includes intravenous, subcutaneous, intramuscular, transdermal, intradermal, intraorbital, ophthalmic, intraventricular, intracranial, intracapsular, intraspinal, intracisternal, intraperitoneal, topical, intranasal, aerosol, scarification, and buccal administration. Also encompassed is intramammary injection where a suspension or solution is introduced into the udder via the teat.

Parenteral administration may include, but is not limited to, sterile solutions which may also contain buffers, diluents and/or carriers, as known by the skilled worker. For example, sterile aqueous solutions of the corresponding water-soluble salts may be used. Such aqueous solutions may be suitably buffered, if necessary, and the liquid diluent first rendered isotonic with sufficient saline or glucose.

Examples of carriers include solutions, solvents, dispersion media, delay agents, emulsions and the like. For example, alcohols, glycols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidine, etc. The pharmaceutical preparations can be sterilized, and, if desired, mixed with auxiliary agents, including lubricants, preservatives, stabilizers, wetting agents, emulsifiers, salts for influencing osmotic pressure, buffers, coloring. Solutions, suspensions, emulsions, or implants, can conveniently be provided for appropriate administration. The use of such carriers for pharmaceutically substances is well known in the art.

As used herein, "oral administration" includes administering the constituents of the combined preparation in a suitable oral form such as, e.g., tablets, capsules, suspensions, solutions or emulsions, powders, syrups, granules or pellets for admixture with feedstuffs; pastes for application to the tongue, and the like.

As used herein, "vaginal administration" includes vaginal administration presented as pessaries, tampons, creams, gels, pastes, foams or spray formulations. Vaginal administration may also occur using an intravaginal device. For example, as a time release composition can be used, as is well known to those skilled in the art. In a specific example, the spine of a Cue-Mate (Bioniche Animal Health, Belleville, ON, Canada) with blank intravaginal pod is used as a support structure for a compound or composition of the present invention.

In one example, a Cue-Mate (Bioniche Animal Health, Belleville, ON, Canada) intravaginal device is used for vaginal administration.

As used herein, "pharmaceutically acceptable" includes the carrier, diluent, excipients, and/or salts or prodrugs, and must be compatible with the other ingredients of the formulation, and not deleterious to the patient.

As used herein, "prodrug" refers to a compound that is transformed in vivo to yield a compound of the present invention. The transformation may occur by various mechanisms, such as through hydrolysis in blood As used herein, "pharmaceutically acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

As noted above, the methods of the present invention relate to use of a lipid-based formulation as described herein, a waxed-based formulation as described herein, a lipid-based formulation with a gel coat, and/or a waxed-based formulation with a gel coat as described herein, comprising the aromatase inhibitor compound, for use in synchronizing ovulation in a herd, inducing superovulation in a single animal: improved frequency of successful implantation and development of fertilized ova, and twinning. In a specific example, the aromatase inhibitor is the non-steroidal aromatase inhibitor letrozole.

In one embodiment, the methods of the present invention relate to use of a lipid-based formulation as described herein, a waxed-based formulation as described herein, a lipid-based formulation with a gel coat, and/or a waxed-based formulation with a gel coat as described herein, comprising the aromatase inhibitor letrozole, in the synchronization of ovulation of members of a herd of cattle, so as to enable timed insemination of the members of the herd.

The term "insemination" as used herein, refers to introducing semen by any method known in the art, including, but not limited to, natural and artificial insemination.

In one example, a lipid-based formulation as described herein, a waxed-based formulation as described herein, a lipid-based formulation with a gel coat, and/or a waxed-based formulation with a gel coat as described herein, comprising an aromatase inhibitor (such as letrozole), may be applied on random days of the estrous cycle to induce the formation of a persistent dominant follicle and delay wave emergence by preventing spontaneous ovulations (i.e., inhibiting the pre-ovulatory rise in estradiol and potentially delaying luteolysis).

In another example, a prostaglandin such as Lutalyse is administered (e.g., 25 mg Lutalyse® administered intramuscularly) followed by administration of a lipid-based formulation as described herein, a waxed-based formulation as described herein, a lipid-based formulation with a gel coat, and/or a waxed-based formulation with a gel coat as described herein, comprising an aromatase inhibitor (such as letrozole), to synchronize individual cows of a herd with respect to the time of occurrence of estrus, ovulation, or both.

In another example, a lipid-based formulation as described herein, a waxed-based formulation as described herein, a lipid-based formulation with a gel coat, and/or a waxed-based formulation with a gel coat as described herein, comprising an aromatase inhibitor (such as letrozole), may be given prior to the initiation of a 5-day Ovsynch protocol so as to increase the ovulation rate on the first GnRH treatment and therefore the total synchrony achieved at the day of artificial insemination.

For the purposes of ovarian superovulation and embryo transfer, superstimulatory treatments may be initiated 36 to 48 hours after treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), and GnRH/pLH treatment.

In another example of superovulation, a lipid-based formulation as described herein, a waxed-based formulation as described herein, and/or a waxed-based formulation with a gel coat as described herein, comprising an aromatase inhibitor (such as Letrozole), is administered at the beginning of follicular wave emergence in a cow, concurrent with a conventional superstimulatory treatment protocol that is also initiated at wave emergence.

In the case of mares, a lipid-based formulation as described herein, a waxed-based formulation as described herein, and/or a waxed-based formulation with a gel coat as described herein, comprising an aromatase inhibitor (such as Letrozole), may be applied on random days of the estrous cycle to induce the formation of a persistent dominant follicle and delay wave emergence by preventing spontaneous ovulations (i.e., inhibiting the pre-ovulatory rise in estradiol and potentially delaying luteolysis). On Day 5 (Day 0=day of treatment), a luteolytic dose of PGF is given to induce regression of the corpus luteum (CL), followed on Day 7 by an ovulatory dose of GnRH or pLH to synchronize ovulation. Insemination (e.g., artificial insemination) at detected estrus or following treatment with GnRH or pLH on Day 6 or 7 to synchronize ovulation (fixed-time artificial insemination [FTAI] on Day 7-7.5).

In another example, there is provided a method for improving fertility. Letrozole treatment, given in early metestrus (about Day 1 post-ovulation) or mid-diestrus (about Day 9 post-ovulation) results in a luteotrophic effect, documented by larger CL diameter and greater plasma progesterone profiles in treated animals. Treatment during the early luteal phase increases CL viability and progesterone production, which is important for ensuring rapid growth of a healthy embryo and successful establishment of pregnancy. In high-producing dairy cows, for example, low levels of progesterone account for low pregnancy rates and high embryonic loss rates a lipid-based formulation as described herein, a waxed-based formulation as described herein, a lipid-based formulation with a gel coat, and/or a waxed-based formulation with a gel coat as described herein, comprising an aromatase inhibitor (such as letrozole), is given one day after artificial insemination to promote development of the CL, resulting in a larger CL diameter and higher circulating concentrations of progesterone.

Similarly, treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), may be given so that its effect encompasses the period of maternal recognition of pregnancy (i.e., the time of luteal response to pregnancy). In cattle, letrozole treatment is initiated on or before 15 days after artificial insemination (maternal recognition of pregnancy is between Days 15 and 17 post-ovulation in cattle). Treatment at this time will promote the establishment of pregnancy through two mechanisms. Firstly, letrozole exerts a luteotrophic effect to enhance CL functionality and survival. Secondly, letrozole will compromise the luteolytic mechanism by decreasing circulating estradiol concentration which mediates the luteolytic process by stimulating the expression of oxytocin receptors in the endometrium, which are necessary for prostaglandin production and release. Again, this is a common problem in high producing dairy cattle; low levels of progesterone result in insufficient trophoblast expansion to block prostaglandin production and release from the uterus.

For embryo transfer recipients, treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), is initiated prior to ovulatory follicular wave emergence to induce co-dominance, and double ovulation. A lipid-based formulation as described herein, a waxed-based formulation as described herein, a lipid-based formulation with a gel coat, and/or a waxed-based formulation with a gel coat as described herein, comprising an aromatase inhibitor (such as letrozole), is given from Day 1 (Day 0=wave emergence) until Day 7. PGF is administered on day 5 followed by GnRH/LH treatment 36 h later. As a result, recipient animals will have more than one corpus luteum and higher progesterone levels to ensure a successful attachment and development of the transferred embryo. An alternative protocol for embryo transfer recipients is treatment with a a lipid-based formulation as described herein, a waxed-based formulation as described herein, a lipid-based formulation with a gel coat, and/or a waxed-based formulation with a gel coat as described herein, comprising an aromatase inhibitor (such as letrozole), initiated one day after ovulation for 5 days to promote development of the new CL, resulting in a larger CL diameter and higher circulating concentrations of progesterone.

In another embodiment there is provided a method of improved twinning. Treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), is given before dominant follicle selection, induces the development of co-dominance; i.e., 2 dominant follicles. A lipid-based formulation as described herein, a waxed-based formulation as described herein, a lipid-based formulation with a gel coat, and/or a waxed-based formulation with a gel coat as described herein, comprising an aromatase inhibitor (such as letrozole), may be used to produce double ovulations and twin pregnancies with mhigher efficiency than other previously explored treatments (e.g., eCG or FSH). The advantage of letrozole treatment is that it appears to induce the development of only two dominant follicles, which overcome the adverse effects of gonadotropin treatments where multiple (3 to 10) ovulations and conceptions commonly occur. In this regard, a letrozole-impregnated slow-releasing device may be applied on the day of or the day after follicle wave emergence of either an anovulatory or ovulatory follicular wave. On Day 5 after wave emergence, the letrozole device is removed and a luteolytic dose of PGF given. Artificial insemination at detected estrus or following treatment with GnRH or pLH on Day 6 or 7 to synchronize ovulation (FTAI) would be expected to result in twin pregnancies, Inducing multiple ovulation in mares is difficult and expensive. Letrozole treatment (as described herein) may be used in mares, with or without other superstimulatory hormones (e.g., FSH or equine pituitary extract), to induce multiple ovulation in mares for the purposes of embryo production and embryo transfer.

Methods of the present invention are conveniently practiced by providing the compound(s) and/or composition(s) used in such method in the form of a kit. Such a kit preferably contains a delivery vehicle comprising an aromatase inhibitor, and the instructions of the use thereof.

To gain a better understanding of the invention described herein, the following examples are set forth. It should be understood that these example are for illustrative purposes only. Therefore, they should not limit the scope of this invention in any way.

EXAMPLES

Example I

Materials and Methods

The development of an effective formulation for intravaginal administration of an inhibitor of estradiol production in cattle in the present study involved three stages. Firstly, the inhibitory effects of three different compounds were examined using bovine granulosa cells in culture. Secondly, the absorbability of the selected aromatase inhibitor prepared in two different vehicles was tested in diffusion chamber studies of bovine vaginal mucosa. Thirdly, an in vivo study was done in cattle to determine the pharmacokinetic characteristics of the respective formulations developed in the diffusion chamber studies.

In Vitro Testing of Different Inhibitors of Estradiol Production

Inhibition of estradiol production by two aromatase inhibitors (letrozole and anastrozole) and a benzimidazole (fenbendazole) was tested in vitro using a bovine granulosa cell culture. The commonly used anthelmintic, fenbendazole, was added as the third possible estradiol inhibitor based on reports that benzimidazole drugs have mild anti-estrogenic effects in mammals and may disturb reproductive events (Kragie, Turner et al., 2002; Johnston, Bieszczak et al., 2006), and that deworming treatment with another benzimidazole (albendazole) in ewes resulted in decreased estradiol concentrations in follicular fluid (Mamali, Samartzi et al., 2008).

The granulosa cell culture protocol has been described previously (Zamberlam, Portela et al., 2011). Briefly, bovine ovaries were obtained at a local abattoir and transported to the lab where granulosa cells of antral follicles were collected by rinsing the follicle wall with Dulbecco's Modified Eagle Medium Nutrient Mixture F-12 (DMEMIF12, Invitrogen Life Technologies, Burlington, ON, Canada). Granullosa cells were maintained in culture for 6 days at 37° C. in 5% $CO_2$, in 700 uL of culture medium (Zamberlam, Portela et al., 2011) which was replaced every 2 days. Cells were maintained in culture from Days 0 to 2, followed by the addition of 1 ng/mL of FSH from Days 2 to 4. On Day 4, depending on the treatment group, the culture medium was supplemented with 1 ng/mL FSH plus the estrogen inhibitor of interest, with FSH alone (positive control) or no FSH (negative control). On Day 6, the culture medium was collected and total protein was measured by the Bradford method (Bio-Rad, Mississauga, ON, Canada). Estradiol levels were determined by radioimmunoassay and expressed as total pg of estradiol per ug of protein.

Three different levels of each compound were tested. The standard concentration used for letrozole was 20 ng/mL. The half maximal inhibitory concentration (IC50) values in MCF-7 cancer cell preparations have been reported to be 0.07 and 0.82 for letrozole and anastrozole, respectively (Kudoh, Susaki et al., 1996; Bhatnagar, 2007). Based on this, we considered letrozole to be approximately 11 times more potent than anastrozole; therefore, the standard dose of anastrozole was set at 200 ng/mL. The standard dose of fenbendazole was based on a reported maximum concentration 160 ng/mL fenbendazole in plasma after a single oral administration of 7.5 mg/kg of body weight in cattle (Sanyal, 1994). Low and high doses of each aromatase inhibitor were arbitrarily set at standard concentration×1/10 and standard concentration×10, respectively (Table 1).

TABLE 1

Treatment groups tested for estradiol inhibitory capability using an in vitro bovine granulosa cell culture.

| Treatment | Low dose (1/10 × standard) | Standard dose | High dose (10 × standard) |
| --- | --- | --- | --- |
| Letrozole | 2 ng/mL | 20 ng/mL | 200 ng/mL |
| Anastrozole | 20 ng/mL | 200 ng/mL | 2000 ng/mL |
| Fenbendazole | 15 ng/mL | 150 ng/mL | 1500 ng/mL |
| Positive Control | FSH + no estradiol inhibitor | | |
| Negative Control | No FSH + no estradiol inhibitor | | |

In Vitro Diffusion Chamber Studies

Based on the results of in vitro testing of different aromatase inhibitors on granulosa cells, letrozole was chosen for further testing and development. Letrozole was prepared in two different formulations (liposome and wax-based) for testing in in vitro diffusion chamber studies. The liposome formulation contained the following ingredients (% w/w): 10% letrozole (Xian Huayang Biological Science and Technology; Xian, China); 10% hydrogenated soy phosphatidylcholine (Phospholipon 90H; American Lecithin Company, Oxford, Conn., USA); 5% cholesterol (Spectrum Chemical and Laboratory Products, New Brunswick, N.J., USA); 2% 1,2-Dioleoyl-sn-Glycero-3-Phosphoethanolamine (DOPE, Avanti Polar Lipids Inc., Alabaster, Ala., USA); 20% propylene glycol and water qs to 100% (Foldvari, Badea et al.). The wax-based formulation contained the following ingredients (% w/w): 10% letrozole; 10% Hydrogenated soy phosphatidylcholine (Phospholipon 90H; American Lecithin Company); 5% cholesterol; 2% DOPE; and hydrogenated vegetable oil (Suppocire D, Gattefosse, Paris, France) q.s. to 100%. Both preparations were heated to 65° C. and vortexed to obtain a uniform mixture.

Bovine vaginal mucosa samples were collected from cows within 3 h of slaughter at a local abattoir. In vitro absorption studies were performed in flow-through diffusion chambers (Cordoba-Diaz, Nova et al., 2000). Full-thickness bovine vaginal mucosa explants were set up in the diffusion chambers (9 mm diameter) and maintained at 39.0° C. The perfusion buffer (0.01 M Na-phosphate buffer) was circulated under the mucosa at a flow rate of 112 uL/min, at 39° C. The mucosal samples were treated with 100 uL of liposome formulation (n=3) or wax-based formulation (n=3) for 24 h. The vaginal mucosa in one chamber remained untreated to serve as a negative control. The perfusion fluid was collected from each chamber into a single container, and 500 uL samples were collected from this container at 0, 1, 2, 3, 4, 5, 6, 8, 12, and 24 h after initiation of treatment to determine cumulative concentration. Samples were stored at −20° C. until extraction for LC/MS/MS quantification of letrozole concentration.

Preparation of Letrozole-Impregnated Intravaginal Devices

The wax-based formulation of letrozole was selected for the formulation of the intravaginal devices based on the results from diffusion chamber studies. Three different devices containing a total of 3 grams of letrozole were tested in vivo: Wax (DOPE)+gel coat, Wax+gel coat, Wax. The Wax (DOPE)+gel coat device was formulated with 2 grams of letrozole contained in the wax-based vehicle covered by a gel coat containing 1 gram of letrozole per device. The wax-based vehicle contained the following (all ingredients % w/w): 10% letrozole; 10% Hydrogenated soy phosphatidylcholine (Phospholipon 90H; American Lecithin Company); 5% cholesterol NF; 2% DOPE; and hydrogenated vegetable oil (Suppocire D, Gattefosse) q.s. to 100%. The gel coat contained the following (all ingredients % w/w): 10% letrozole, 20% gelatin (Gelatin type B, Fisher Scientific, Pittsburgh, PA, USA), 65% polymer (prepared by hydrating 12% poloxamer 188 and 20% poloxamer 407, both from Spectrum Chemical, New Brunswick, N.J., USA, with 68% distilled water), distilled water qs to 100%. The Wax+gel coat device was formulated similarly, except that DOPE was excluded from the formulation. The Wax device was 100% wax-based, and contained the following ingredients (% w/w): 10% letrozole; 10% hydrogenated soy phosphatidylcholine (Phospholipon 90H; American Lecithin Company); 5% cholesterol; and hydrogenated vegetable oil (Suppocire D, Gattefosse) q.s. to 100%.

In Vivo Testing of Letrozole Intravaginal Devices

The spine of a Cue-Mate (Bioniche Animal Health, Belleville, ON, Canada) with blank (progesterone-free) intravaginal pods was used as a support structure for the letrozole devices. Beef heifers were given intravaginal devices as follows: blank devices (control, n=4), Wax (DOPE)+gel coat devices (n=2), Wax+gel coat devices (n=4), and Wax devices (no gel coat, n=4). To determine the pharmacokinetics of the respective formulations, blood samples were taken at 0, 10, 20, 30 min, 1, 2, 3, 4, 6, 8, 12 and 24 h, twice daily until Day 4, and daily thereafter until Day 12 after device placement. Frequent sampling was performed using an indwelling jugular catheter as described (Bergfelt, Smith et al., 1997). Daily blood samples were collected by jugular or coccygeal venipuncture into 10 mL heparinized vacuum tubes (Becton Dickinson Vacutainer Systems, Franklin Lakes, N.J., USA).

Plasma samples were analyzed by LCMS/MS for letrozole concentration. Peak concentration in plasma ($C_{max}$) and time to peak concentration ($t_{max}$) were determined using observed values. The area under the concentration-time curve until the final plasma sample ($AUC_{last}$) was determined using the linear trapezoidal rule. Bioavailability was determined by comparing the respective AUCs of letrozole given intravaginally and intravenously (Yapura et al. 2013a), corrected by dose. Relative bioavailability refers to the availability of one letrozole formulation as compared to another formulation. These measurements determine the effects of formulation differences on drug absorption (Makoid, Vuchetich et al., 1996).

Measurement of Plasma Letrozole Concentration

Letrozole concentration was determined using high performance liquid chromatography tandem mass spectrometry (LC/MS/MS), as described previously (Chidambara, Shivaprsad et al., 2011). Partial validation of the method was conducted as recommended when the same matrix but from different species is being analyzed (human plasma versus bovine plasma; (US Food and Drug Administration, U.S. Department of Health and Human Services et al., 2001). Partial validation parameters included linearity, selectivity, accuracy and precision, Linearity was tested by running six standard curves independently. Ratio counts versus concentration were plotted and R-square values were calculated. The mean (±SEM) R-square value was 0.998±0.0009. The calibration curve had to have a correlation coefficient ($r^2$)≥0.99. The acceptance criterion for each calculated standard concentration was 15% deviation from the nominal value except lower limit of quantification (LLOQ) samples, which was set at 20% (Table 2).

Selectivity, defined as the degree to which the response is unaffected by contributions from the matrix, was tested in six independent bovine plasma lots, spiked with one single value within the standard curve (30 ng/mL) and plotted against a non-extracted standard curve made on mobile phase. A pooled plasma sample was also included. The results (30.8±0.19 ng/mL) showed that there were no significant differences for letrozole concentration among plasma sources.

Accuracy and precision were calculated by running four different concentrations of quality control (QC) samples (0.2, 0.5, 30, and 70 ng/mL) six times. Accuracy was calculated as percentage of the true concentration of letrozole recovered by the assay. Precision, expressed as the relative standard deviation was assessed using the following formula: % RSD=(STD DEV×100)/mean. The acceptance criteria of precision were ≤20% LLOQ and ≤15% for the remaining concentrations and for accuracy were 100±≤20% for LLOQ and 100±≤15% or higher for the remaining concentrations (Table 3).

Given that accuracy did not meet the required criteria for blank bovine plasma standards spiked with 0.2 and 0.4 ng/mL of letrozole, samples with less than 2 ng/mL concentration were considered as 0 (zero).

TABLE 2

Precision and accuracy data of calculated concentrations of calibration samples for letrozole in bovine plasma (n = 6).

| Concentration added (ng/mL) | Concentration found (mean ± SD; ng/mL) | Precision (%) | Accuracy (%) |
| --- | --- | --- | --- |
| 0.2 | 0.75 ± 0.035 | 10.49 | 378.5 |
| 0.4 | 0.93 ± 0.039 | 9.45 | 241.8 |
| 2 | 2.28 ± 0.033 | 3.24 | 114.0 |
| 8 | 7.96 ± 0.045 | 1.26 | 99.5 |
| 25 | 22.92 ± 0.114 | 1.11 | 91.7 |
| 50 | 48.80 ± 0.167 | 0.77 | 97.6 |
| 75 | 77.50 ± 0.324 | 0.93 | 103.3 |
| 100 | 99.25 ± 0.258 | 0.58 | 99.3 |

TABLE 3

Precision and accuracy of the LCMS/MS method for determining letrozole concentrations in plasma samples

| Concentration added (ng/mL) | Concentration found (mean ± SD; ng/mL) | Precision (%) | Accuracy (%) |
| --- | --- | --- | --- |
| 0.2 | 0.8 ± 0.04 | 12.1 | 398.2 |
| 0.5 | 1.6 ± 0.05 | 6.8 | 325.7 |
| 30 | 28.0 ± 0.16 | 1.3 | 93.4 |
| 70 | 72.3 ± 0.24 | 0.7 | 103.3 |

Statistical Analyses

Statistical analyses were done using the Statistical Analysis System software package (SAS Learning Edition 9.1, 2006; SAS Institute Inc., Cary, N.C., USA). Time-series data (letrozole concentration) were analyzed by repeated measures, using the PROC MIXED procedure. The main effects were formulation, time, and their interactions. Single-point measurements (pharmacokinetic parameters) were analyzed by ANOVA, and differences among more than two means were further analyzed by Tukey's post-hoc test for multiple comparisons. Individual time point comparisons between treatment groups were performed using least significant difference (LSD) test. A probability of P≤0.05 was used to indicate significance and probabilities between P>0.05 and P<0.10 indicated that a difference approached significance. Data are presented as the mean±SEM.

Results

In Vitro Testing of Different Inhibitors of Estradiol Production

Figure 1B:
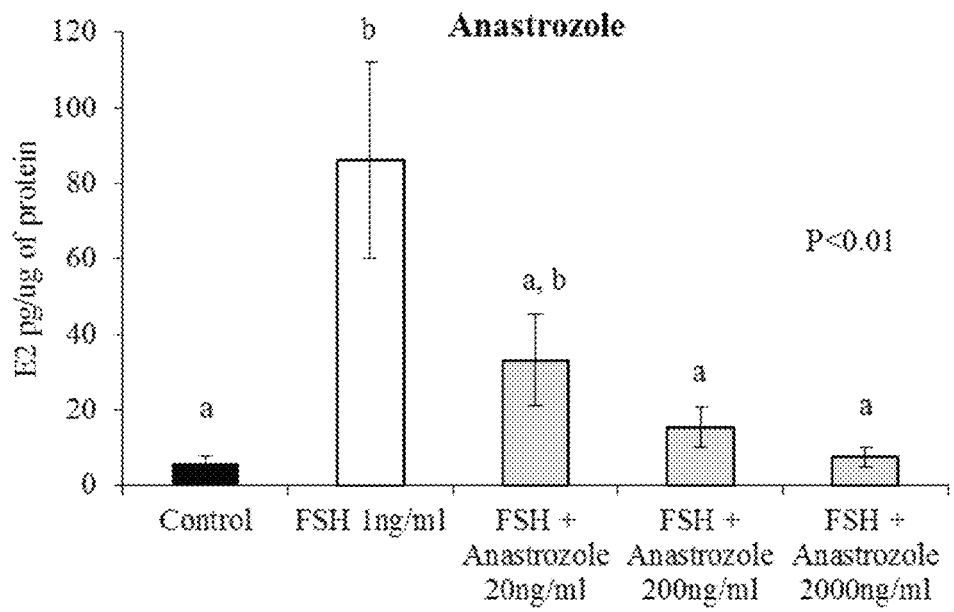
Figure 1C:
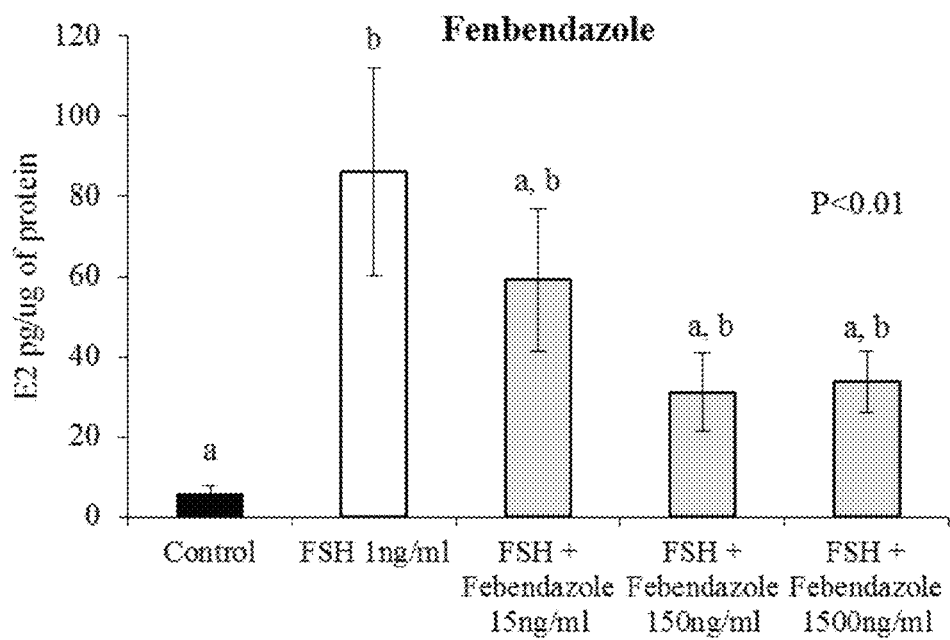

Aromatase activity in bovine granulosa cell culture after aromatase inhibitor treatment was determined in three replicates. Results are shown in FIG. 1, FIG. 1 depicts the effect of three different inhibitors of estradiol production on estradiol secretion by bovine granulosa cells in culture. Cells were cultured in vitro for 6 days under non-luteinising conditions without treatment (negative control), or treatment with FSH alone (positive control) or with letrozole (A), anastrozole (B) or fenbendazole (C) at $\frac{1}{10}$× standard, standard or 10× standard doses. Data are presented as the mean±SEM estradiol concentrations in three independent replicate cultures for each inhibitor. [a,b] Values with no common superscript are different (P<0.05);

Letrozole and anastrozole were the most effective in reducing estradiol secretion by granulosa cells in vitro. Concentration of estradiol following 20 and 2 ng/mL of letrozole, and 200 and 20 ng/mL of anastrozole did not differ from that of the negative control (no FSH stimulation). Febendazole, at the levels tested did not reduce estradiol secretion significantly by FSH-stimulated granulosa cells.

Diffusion Chamber Study Results

Figure 2:
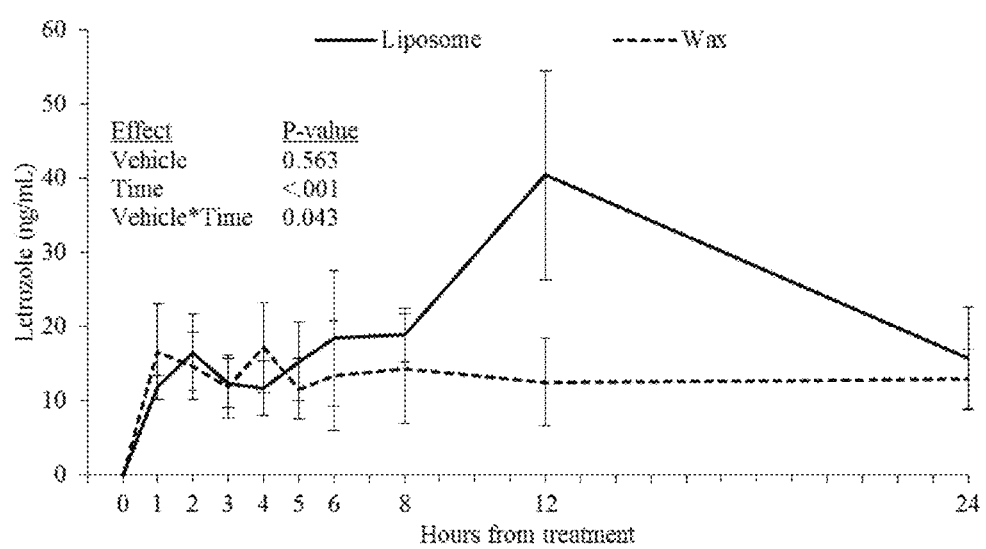
FIG. 2 is a graph depicting Letrozole concentrations in saline during diffusion chamber trial for 24 hours. Letrozole was prepared in a liposome- or a wax-based vehicle and its diffusion through bovine vaginal mucosa was tested in diffusion chambers using phosphate buffered saline as perfusion buffer. Data from three diffusion chambers per formulation are presented as mean±SEM.

Letrozole concentrations obtained with each formulation on the vaginal mucosa in diffusion chamber studies are shown in FIG. 2.

FIG. 2 depicts Letrozole concentrations in saline during diffusion chamber trial for 24 hours. Letrozole was prepared in a liposome- or a wax-based vehicle and its diffusion through bovine vaginal mucosa was tested in diffusion chambers using phosphate buffered saline as perfusion buffer. Data from three diffusion chambers per formulation are presented as mean±SEM.

Figure 3:
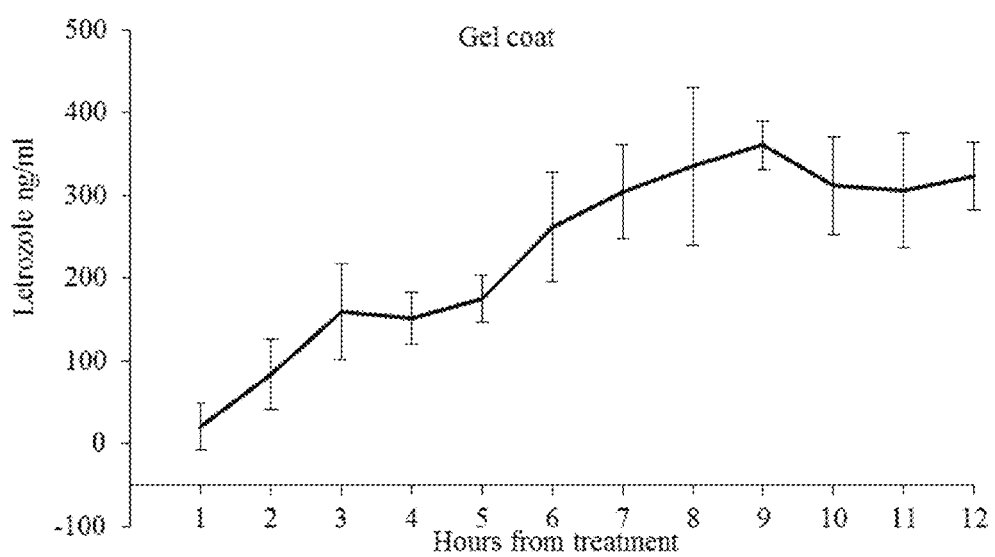
FIG. 3 is a graph depicting Letrozole concentrations in saline during diffusion chamber trial for 12 hours. Letrozole was prepared in a gel vehicle and its diffusion through bovine vaginal mucosa was tested in diffusion chambers using phosphate buffered saline as perfusion buffer. Data from two diffusion chambers per formulation are presented as mean±SD

Although not statistically different, the wax-based formulation released letrozole at a consistent rate as indicated by the minimum changes in letrozole concentration over time. On the contrary, the sudden increase followed by a decrease in letrozole concentration observed in the liposome-based vehicle indicates that by the 12 h point most letrozole had been released and absorbed through the vaginal mucosa, after which letrozole concentrations dropped due to dilution, FIG. 3 depicts Letrozole concentrations in saline during diffusion chamber trial for 12 hours. Letrozole was prepared in a gel vehicle and its diffusion through bovine vaginal mucosa was tested in diffusion chambers using phosphate buffered saline as perfusion buffer. Data from two diffusion chambers per formulation are presented as mean±SD.

In Vivo Testing of Letrozole Intravaginal Devices

All devices remained in place for 8 days. Although a mild vaginitis was observed at the time of device removal, general health of the heifers was not compromised and was considered to be optimal by an attending veterinarian (JY).

The formulations coated with gel delivered letrozole more rapidly than that without a gel coating. There were no differences among formulations in mean letrozole concentrations over the first 12 h or during the 12 day observational period. However, when multiple comparisons among groups were performed by hour during the first 12 h, devices containing gel coat had significantly higher concentration of letrozole in plasma by 3 h post-device insertion compared to the wax alone group (FIG. 4).

Figure 4:
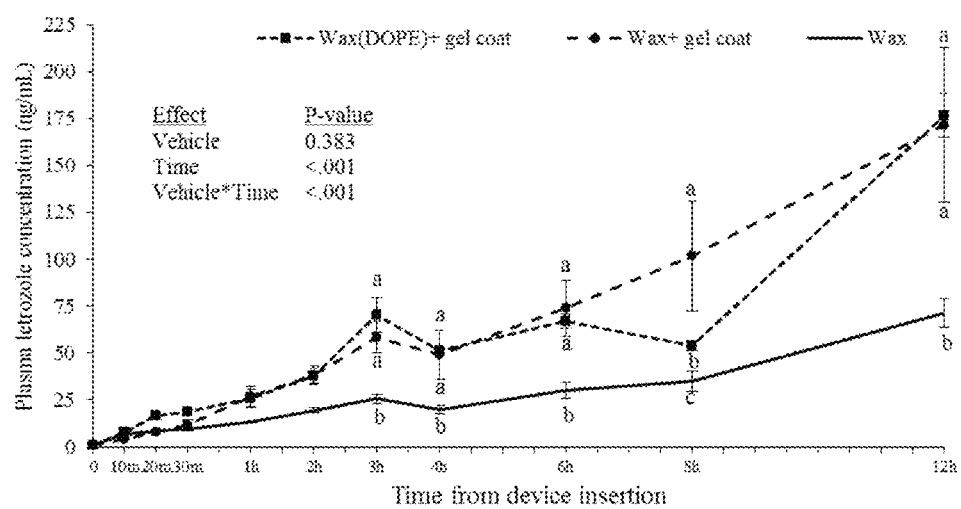
FIG. 4 is a graph depicting Letrozole concentrations in plasma (mean±SEM) during the first 12 h following treatment with a letrozole-containing intravaginal device in heifers. Letrozole devices were prepared in three formulations: Wax (DOPE)+gel coat (n=2), Wax+gel coat (n=4), Wax only (n=4), $^{a\ b\ c}$ On indicated days, values differed among groups (P≤50.05).

FIG. 4 depicts Letrozole concentrations in plasma (mean±SEM) during the first 12 h following treatment with a letrozole-containing intravaginal device in heifers. Letrozole devices were prepared in three formulations: Wax (DOPE)+gel coat (n=2), Wax+gel coat (n=4), Wax only (n=4). a b c On indicated days, values differed among groups (P≤50.05).

Figure 5:
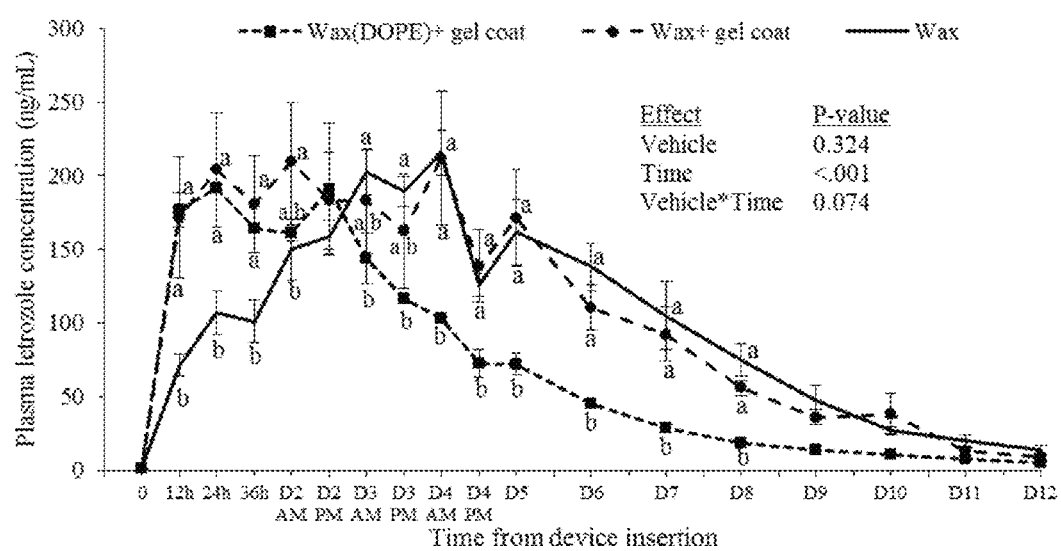
FIG. 5 is a graph depicting Plasma letrozole concentrations in heifers (mean±SEM) over 12 days following treatment with a letrozole-containing intravaginal device. Letrozole devices were prepared in three formulations: Wax (DOPE)+gel coat (n=2), Wax+gel coat (n=4), Wax only (n=4). $^{ab}$ On indicated days, values differed among groups (P≤0.05).

Letrozole concentration profiles over 12 days following device insertion are showed in FIG. 5.

FIG. 5 depicts plasma letrozole concentrations in heifers (mean SEM) over 12 days following treatment with a letrozole-containing intravaginal device. Letrozole devices were prepared in three formulations: Wax (DOPE)+gel coat (n=2), Wax+gel coat (n=4), Wax only (n=4) a b On indicated days, values differed among groups (P≤50.05).

Wax alone group reached concentration similar to the gel coating devices (wax (DOPE)+gel coat and wax+gel coat) by 60 h, although concentration achieved with the wax (DOPE)+gel coat devices were significantly lower than the other two formulations after 4 days from device insertion. Pharmacokinetic parameters for the three formulation tested are summarized on Table 4 and Table 5.

TABLE 4

$C_{max}$ and $t_{max}$ (mean ± SD) in cattle after treatment with different letrozole-containing intravaginal devices: Wax (DOPE) + gel coat (n = 2), Wax + gel coat (n = 4) and Wax (n = 4).

| Parameter | Wax (DOPE) + gel coat | Wax + gel coat | Wax |
|---|---|---|---|
| $C_{max}$ (ng/mL) | 214 ± 29.3 | 240 ± 91.4 | 225 ± 25.7 |
| $t_{max}$ (h) | 42 ± 25.5 | 72 ± 27.7 | 90 ± 12.0 |

TABLE 5

Blood plasma letrozole content (AUClast) in cattle after treatment with different letrozole-containing intravaginal devices: Wax (DOPE) + gel coat (n = 2), Wax + gel coat (n = 4) and Wax (n = 4).

| | Area under the curve ($AUC_{last}$) (hours × ng/mL) | | |
|---|---|---|---|
| | Wax (DOPE) + gel coat | Wax + gel coat | Wax |
| | 18424 | 36485 | 24783 |
| | 19453 | 20151 | 20693 |
| | — | 35397 | 31519 |
| | — | 18815 | 24816 |
| Mean | 18938 | 27712.0 | 25452.9 |
| SD | 727.5 | 9528.2 | 4483.5 |
| Bioavailability | 43% | 63% | 58% |
| Relative Bioavailability | 68% | 100% | 92% |

Discussion

The efficacy of three compounds (letrozole, anastrozole and fenbendazole) was examined for inhibiting estradiol production by bovine granulosa cell cultures in vitro. Letrozole and anastrozole were efficacious in reducing estradiol production to levels found in non-FSH-stimulated granulosa cells. Fenbendazole, however, did not reduce estradiol concentrations significantly. This observation is consistent with reports that letrozole and anastrozole are very specific inhibitors of the aromatase enzyme (Bhatnagar, Häusler et al., 1990; Dukes, Edwards et al., 1996), while the mechanism by which fenbendazole impairs estrogen synthesis in mammals remains unclear. However, it has been reported that albendazole, a benzimidazole anthelmintic drug closely related to fenbendazole, can inhibit the activity of cytochrome P450 enzymes (CYP enzymes) in vitro in rat and mouflon sheep (Baliharova, Velik et al.; Murray, Hudson et al., 1992), a family of enzymes of which aromatase is a member (Simpson, Mahendroo et al., 1994). It is possible that fenbendazole may have had a direct, although mild, effect on P450 aromatase activity in the bovine granulosa cells in vitro. In comparing relative potencies, letrozole was more potent that anastrozole; estradiol synthesis was reduced to that of non-FSH-stimulated cells at a lower dose for letrozole than anastrozole (20 ng/mL vs 200 ng/mL, respectively). This observation is in agreement with a previous report that letrozole was several orders of magnitude more potent than anastrozole in vitro using cell culture from tissues of different origins (Bhatnagar, Brodie et al., 2001).

The wax-based vehicle released letrozole at a steady rate. The profile (letrozole concentration over time) from the liposome-treated chambers indicated rapid liquefaction and absorption of the letrozole-containing vehicle through the vaginal mucosa. Letrozole concentrations peaked at 12 h and began to decrease by 24 h post-treatment.

Regarding prolonged treatment in farm animals, the intravaginal route is desirable for the administration of aromatase inhibitor because it is well-tolerated by the animals, it reduces handling and stress, it is user-friendly, there is a high retention rate (which varies with device design), it is easy applied, and it enables controlled withdrawal.

After selection of the wax-based vehicle for further development, three different formulations of intravaginal devices were tested. The addition of DOPE to the wax-based mixture was to determine whether it would enhance absorption through the vaginal mucosa by enhancing the fusion of the liposomes to the cellular membrane. However, the addition of DOPE to the formulation increased the cost of the devices and hastened the elimination of letrozole (2 days after device insertion vs. 4 days in the other groups). Compared to the wax-only device, the addition of the gel coat hastened the initial increase in plasma letrozole concentrations (maximum concentration at 12 h vs. 3 days).

Bioavailability was calculated using historical AUClast data obtained in earlier studies using an intravenous route of administration (Yapura et al. 2013a). We concluded that the Wax+gel coat device provided the highest bioavailability, followed closely by the Wax-only device. Although the total amount of letrozole delivered (AUClast) did not differ between the Wax+gel coat device and Wax-only device, the characteristics of the delivery during both the first 12 hours and 12 days did differ.

Partial validation of the LCMS/MS method to measure letrozole levels in bovine plasma was required. The results of validation indicated that samples below 2 ng/mL could not be quantified by the method employed in this study given that accuracy did not meet the required criteria for blank bovine plasma standards spiked with 0.2 and 0.4 ng/mL of letrozole. However, all the other parameters investigated during partial validation (precision, linearity, and selectivity) fell within acceptable ranges.

In summary, among the aromatase inhibitors tested, letrozole had greatest potency, as determined by inhibition of estradiol production in vitro. Furthermore, a wax-based vehicle allowed for a steady and continuous delivery of the active compound over the treatment period. Finally, the addition of a letrozole-containing gel coating improved initial absorption and hastened the increase on plasma concentrations of the active ingredient, while the letrozole-containing wax-based vehicle prolonged drug-delivery from the intravaginal device.

REFERENCES

Baliharova, V., Velik, J., Fimanova, K., Lamka, J., Szotakova, B., Savlik, M. & Skalova, L. Inhibitory effect of albendazole and its metabolites on cytochromes P450 activities in rat and mouflon in vitro. Pharmacol Rep. 2005 January-February; 57(1):97-106.

Beatson, G. T. (1983). On the treatment of inoperable cases of carcinoma of the mamma: Suggestions for a new method of treatment, with illustrative cases. CA Cancer J Clin, 33(2), 108-121.

Bergfelt, D. R., Smith, C. A., Adams, G. P. & Ginther, O. J. (1997). Surges of FSH during the follicular and early luteal phases of the estrous cycle in heifers. Theriogenology, 48(5), 757-768.

Bhatnagar, A. (2007). The discovery and mechanism of action of letrozole. Breast Cancer Res Treat, 105(0), 7-17.

Bhatnagar, A. S., Brodie, A. M. H., Long, B. J., Evans, D. B. & Miller, W. R. (2001). Intracellular aromatase and its relevance to the pharmacological efficacy of aromatase inhibitors. The Journal of Steroid Biochemistry and Molecular Biology, 76(1–5), 199-202.

Bhatnagar, A. S., Häusler, A., Schieweck, K., Lang, M. & Bowman, R. (1990). Highly selective inhibition of estrogen biosynthesis by CGS 20267, a new non-steroidal aromatase inhibitor. J Steroid Biochem Mol Biol, 37(6), 1021-1027.

Buzdar, A. U. (2003). Pharmacology and pharmacokinetics of the newer generation aromatase inhibitors. Clin Cancer Res, 9(1), 468S-472.

Buzdar, A. U., Robertson, J. F. R., Eiermann, W. & Nabholtz, J.-M. (2002). An overview of the pharmacology and pharmacokinetics of the newer generation aromatase inhibitors anastrozole, letrozole, and exemestane. Cancer, 95(9), 2006-2016.

Chidambara, J., Shivaprsad, V., Satyendranath, C. & Subbarao, M. (2011). Validation and Application of a High-Performance Liquid Chromatography-Tandem Mass Spectrometry Assay for Letrozole in Human Plasma. Asian Journal of Pharmaceutical and Clinical Research, 4(2), 107-112.

Cordoba-Diaz, M., Nova, M., Elorza, B., Cordoba-Diaz, D., Chantres, J. R. & Cordoba-Borrego, M. (2000). Validation protocol of an automated in-line flow-through diffusion equipment for in vitro permeation studies. Journal of Controlled Release, 69(3), 357-367.

Daxenberger, A., Ibarreta, D. & Meyer, H. H. D. (2001). Possible health impact of animal oestrogens in food. Hum Reprod Update, 7(3), 340-355.

de Ziegler, D. (2003). Associate editor's commentary: The dawning of the non-cancer uses of aromatase inhibitors in gynaecology. Hum Reprod, 18(8), 1598-1602.

Dukes, M., Edwards, P. N., Large, M., Smith, I. K. & Boyle, T. (1996). The Preclinical Pharmacology of Arimidex (Anastrozole; ZD1033); a Potent, Selective Aromatase Inhibitor. The Journal of Steroid Biochemistry and Molecular Biology, 58(4), 439-445.

Ebert, A. D., Bartley, J. & David, M. (2005). Aromatase inhibitors and cyclooxygenase-2 (COX-2) inhibitors in endometriosis: New questions—old answers? Eur J Obstet Gynecol Reprod Biol, 122(2), 144-150.

Foldvari, M., Badea, I., Kumar, P., Wettig, S., Batta, R., King, M. J., He, Z., Yeboah, E., Gaspar, K., Hull, P. & Shear, N. H. Biphasic vesicles for topical delivery of interferon alpha in human volunteers and treatment of patients with human papillomavirus infections. Current drug delivery, 8(3), 307-319.

Galbraith, H. (2002). Hormones in international meat production: biological, sociological and consumer issues. Nutr Res Rev, 15(02), 293-314.

Geisler, J., Haynes, B., Anker, G., Dowsett, M. & Lonning, P. E. (2002). Influence of letrozole and anastrozole on total body aromatization and plasma estrogen levels in postmenopausal breast cancer patients evaluated in a randomized, cross-over study. J Clin Oncol, 20(3), 751-757.

Hafez, I. M. & Cullis, P. R. (2001). Roles of lipid polymorphism in intracellular delivery. Advanced Drug Delivery Reviews, 47(2–3), 139-148.

Harper, R., Bennett, W. A., Cuadra, E. J., Vaughn, C. F. & Whitworth, N. S. (2008). Effects of GnRH in combination with PGF2[alpha] on the dynamics of follicular and luteal cells in post-pubertal Holstein heifers. Livest Prod Sci, 117(1), 88-92.

Johnston, N. A., Bieszczak, J. R., Verhulst, S., Disney, K. E., Montgomery, K. E. & Toth, L. A. (2006). Fenbendazole Treatment and Litter Size in Rats. Journal of the American Association for Laboratory Animal Science, 45(6), 35-39.

Kim, U.-H., Suh, G.-H., Nam, H.-W., Kang, H.-G. & Kim, I.-H. (2005). Follicular wave emergence, luteal function and synchrony of ovulation following GnRH or estradiol benzoate in a CIDR-treated, lactating Holstein cows. Theriogenology, 63(1), 260-268.

Kolok, A. S. & Sellin, M. K. (2008). The environmental impact of growth-promoting compounds employed by the United States beef cattle industry: History, current knowledge, and future directions. In The environmental impact of growth-promoting compounds employed by the United States beef cattle industry: History, current knowledge, and future directions pp. 1-30.

Kragie, L., Turner, S. D., Patten, C, J., Crespi, C. L. & Stresser, D. M, (2002). Assessing Pregnancy Risks of Azole Antifungals Using a High Throughput Aromatase Inhibition Assay. Endocrine Research, 28(3), 129-140.

Kudoh, M., Susaki, Y., Ideyama, Y., Nanya, T., Mori, M., Shikama, H. & Fujikura, T. (1996). Inhibitory effect of a novel non-steroidal aromatase inhibitor, YM511 on the proliferation of MCF-7 human breast cancer cell. The Journal of Steroid Biochemistry and Molecular Biology, 58(2), 189-194.

Lane, E. A., Austin, E. J. & Crowe, M. A. (2008). Oestrous synchronisation in cattle—Current options following the EU regulations restricting use of oestrogenic compounds in food-producing animals: A review. Anim Reprod Sci, 109(1-4), 1-16.

Makoid, M. C., Vuchetich, P. J, & Banakar, U. V. (1996). Basic Pharmacokinetics. Virtual University Press.

Mamali, P., Samartzi, F., Batzias, G. C., Theodosiadou, E., Vainas, E., Goulas, P., Belibasaki, S. & Saratsis, F. (2008). The effect of albendazole administration on the concentration of ovarian steroids in the follicular fluid and the maturation of oocytes in the ewe. In The effect of albendazole administration on the concentration of ovarian steroids in the follicular fluid and the maturation of oocytes in the ewe Ed Rodriguez-Martinez, H. p Reprod Domest Anim Vol 43:192. Reprod Domest Anim, Budapest, Hungary.

Martinez, M. F., Kastelic, J. P., Colazo, M. G. & Mapletoft, R. J. (2007). Effects of estradiol on gonadotrophin release, estrus and ovulation in CIDR-treated beef cattle. Domest Anim Endocrinol, 33(1), 77-90.

Murray, M., Hudson, A. M. & Yassa, V. (1992). Hepatic microsomal metabolism of the anthelmintic benzimidazole fenbendazole: enhanced inhibition of cytochrome P450 reactions by oxidized metabolites of the drug. Chemical Research in Toxicology, 5(1), 60-66.

Official Journal of the European Union L 262, 14 Oct. 2003. Directive 2003/74/EC of the European Parliament and of the Council on 22 Sep. 2003 amending Council Directive 96/22/EC concerning the prohibition on the use in stock-farming of certain substances having a hormonal or thyristatic action and of beta-agonist. pp. 17-21. Brussels, Belgium, 2003.

Rathbone, M. J. (2012). Delivering drugs to farmed animals using controlled release science and technology. International e-Journal of Science, Medicine & Education (IeJSME), 6(Suppl 1), S118-S128.

Requena, A., Herrero, J., Landeras, J., Navarro, E., Neyro, J. L., Salvador, C., Tur, R., Callejo, J., Checa, M. A., Farre, M., Espinos, J. J., Fabregues, F. & Grana-Barcia, M. (2008). Use of letrozole in assisted reproduction: A systematic review and meta-analysis. Hum Reprod Update, 14(6), 571-582.

Sanyal, P. K. (1994). Pharmacokinetic behaviour of fenbendazole in buffalo and cattle. Journal of Veterinary Pharmacology and Therapeutics, 17(1), 1-4.

Simpson, E. R., Mahendroo, M. S., Means, G. D., Kilgore, M. W., Hinshelwood, M. M., Graham-Lorence, S., Amarneh, B., Ito, Y., Fisher, C. R., Michael, M. D., Mendelson, C. R. & Bulun, S. E. (1994). Aromatase Cytochrome P450. The Enzyme Responsible for Estrogen Biosynthesis. Endocrine Reviews, 15(3), 342-355, US Food and Drug Administration, U.S. Department of Health and Human Services, Center for Drug Evaluation and Research (CDER) & Center for Veterinary Medicine (CVM) (2001). Guidance for Industry: Bioanalytical Method Validation. Available at http://www.fda.gov/downloads/Drugs/GuidanceComplianceRegulatoryInformation/Guidan ces/ucm070107.pdf. Accessed on Jun. 7, 2012.

Yapura J., Mapletoft R. J., Pierson R. A. J., Adams G. P. (2013a) Effect of vehicle and route of administration of letrozole on ovarian function in a bovine model. Reproduction Fertility and Development (submitted Mar. 22, 2013).

Yapura J., Mapletoft R. J., Pierson R. A. J., Adams G. P. (2013b) Aromatase inhibitor treatment with an intravaginal device and its effect on pre-ovulatory ovarian follicles in a bovine model. Reproductive Biology and Endocrinology (submission March, 2013).

Yapura, J., Mapletoft, R. J., Pierson, R., J., Naile, J., Giesy, J. P. & Adams, G. P. (2011a). A bovine model for examining the effects of an aromatase inhibitor on ovarian function in women. Fertility and Sterility, 96(2), 434-438.e433.

Yapura, J., J., Mapletoft, R. J., Pierson, R., Rogan, D. & Adams, G. P. (2011). Effect of a Prolonged Aromatase Inhibitor Treatment on Pre-Ovulatory Ovarian Follicles in Cattle. Reproduction, Fertility and Development, 24(1), 113-113.

Yapura, M. J., Mapletoft, R. J., J., Pierson, R., Naile, J., Giesy, J. P., Chang, H., Higley, E., Hecker, M. & Adams, G. P. (2011b). Effects of a non-steroidal aromatase inhibitor on ovarian function in cattle. Reproduction, Fertility and Development, 24(4), 631-640.

Yapura, M. J., Mapletoft, R. J., J., Pierson, R. A., Rogan, D. & Adams, G. P. (2011c). Effects of Vehicle and Route of Administration of Letrozole on Ovarian Function in Cattle. Reproduction, Fertility and Development, 23(1), 190-190.

Zamberlam, G., Portela, V., de Oliveira, J. F. C., Gonçalves, P. B. D. & Price, C. A. (2011). Regulation of inducible nitric oxide synthase expression in bovine ovarian granulosa cells. Molecular and Cellular Endocrinology, 335 (2), 189-194.

Example II

The study was designed to determine the physiologic effects of letrozole intravaginal device formulations by assessment of estradiol inhibition and changes in ovarian function. Heifers in which a CL was detected during the initial examination were treated intramuscularly with 500 pg of cloprostenol to synchronize ovulation. At the time of ovulation (Day 0), heifers were assigned randomly to three groups and given an intravaginal device containing wax+gel formulation (3 g of letrozole per device, n=4), wax formulation (3 g of letrozole per device, n=4), no formulation (blank device, Control, n=4). Intravaginal devices were inserted on Day 3 and kept in place for 8 days. Transrectal ultrasound examinations and blood sample collections were performed daily. The dominant follicle diameter profile was larger in heifers treated with the wax+gel coat device than in heifer in the other treatment groups (P<0.04), and the interwave interval was prolonged in heifers in both letrozole-treated groups compared to controls (P<0.001). Plasma estradiol concentrations were reduced significantly in the letrozole-treated groups. Although no differences in corpus luteum diameter were detected among treatment groups, plasma progesterone concentrations were lower in the wax letrozole-treated group than in other groups (P<0.02).

As shown herein, letrozole-impregnated intravaginal devices formulated with a wax base plus gel coat vehicle were suitable for a letrozole-based protocol for the synchronization of ovulation in cattle. It effectively reduced estradiol production resulting in prolonged dominant follicle growth and lifespan, without adversely affecting progesterone production.

Materials and Methods

Cattle

Hereford-cross beef heifers (n=12), 15 to 20 months of age and weighing between 342 and 592 kg (457 t 17.7 kg), were chosen from a herd of 50 heifers maintained in outdoor corrals at the University of Saskatchewan Goodale Research Farm (52° North and 106° West). Heifers were fed alfalfa/grass hay and grain to gain approximately 1.3 Kg per day and had water available ad libitum during the experimental period from August to September. Heifers were initially examined by transrectal ultrasonography (MyLab5, Canadian Veterinary Imaging, Georgetown, Ontario Canada) to detect the presence of a CL (i.e., confirm that they were post-pubertal) (Pierson and Ginther 1987). Animal procedures were performed in accordance with the Canadian Council on Animal Care and were approved by University of Saskatchewan Protocol Review Committee.

Treatments and Examinations

The progesterone-free spine and blank pods of a commercially available intravaginal device for cattle (Cue-Mate, Bioniche Animal Health, Belleville, ON, Canada) were used as a support structure for the administration of letrozole. Briefly, one device type (wax+gel coat) was prepared using a wax-based vehicle containing 2 g of letrozole per device coated with a gel-based formulation containing 1 g of letrozole (total of 3 g of letrozole per device) (as described in Example 1). The second device type (wax) was compounded entirely of the wax-based formulation containing 3 g of letrozole per device.

Heifers in which a CL was detected during the initial examination were treated intramuscularly with 500 pg of cloprostenol (PGF, Estrumate™, Schering-Plough Animal Health, Pointe-Claire, QC, Canada) to induce luteolysis and ovulation (Hafs, Louis et al. 1974). On Pay 3 (Day 0=ovulation), heifers were assigned randomly to one of three groups (n=4 per group) and given an intravaginal device containing the wax+gel coat formulation, wax formulation, or no letrozole (blank device, control). The intravaginal device was left in place for 8 days.

Observations from daily transrectal ultrasound examinations of the ovaries were recorded on a sketch sheet to monitor the dynamics of the CL and follicles z 4 mm in diameter (Knopf, 128 Kastelic et al, 1989). Ovulation was defined as the sudden disappearance of a follicle ≥8 mm between two consecutive examinations, and was confirmed by the subsequent development of a CL (Pierson and Ginther 1987). Follicular wave emergence was taken as the day of ovulation, or determined retrospectively as the day when the dominant follicle was first identified at a diameter of 4 or 5 mm (Adams, Kot et al. 1993; Ginther, Kot et al. 1997). If the dominant follicle was not identified until it reached 6 or 7 mm, the previous day was considered the day of the follicular wave emergence (Kastelic, Knopf et al. 1990). The dominant follicle of a wave was defined as the largest follicle of the wave (Peter, Levine et al. 2009). The day of onset of follicular or luteal regression was defined, in retrospect, as the first day of an apparent progressive decrease in diameter (Adams, Kot et al. 1993).

Blood Samples and Hormone Assays

Blood samples were collected by coccygeal venipuncture Into 10 mL heparinized vacuum tubes (Becton Dickinson Vacutainer Systems, Franklin Lakes, N.J., USA). Samples were collected daily from pre-treatment ovulation (Day 0) to Day 15. Blood samples were centrifuged at 1500×g for 20 min, and plasma was separated and stored in plastic tubes at −20° C.

Plasma concentrations of estradiol were determined using a commercial RIA kit (Double Antibody Estradiol; Diagnostic Products, Los Angeles, Calif., USA). The procedure was carried out at the Department of Animal Health and Biomedical Sciences, University of Wisconsin—Madison, as described (Bergfelt, Kulick et al. 2000; Kulick, Kot et al. 1999), with the following modifications: Standards (0.78-100 pg/mL) were prepared in steroid-free (charcoal-treated) bovine plasma. The standards (250 µL in duplicate) and plasma samples (500 µL in duplicate) were extracted with 3 mL of diethyl ether, frozen in a dry-ice/methanol bath, decanted into assay tubes, and dried overnight under a fume hood. The dried samples and standards were re-suspended with 100 µL of assay buffer (0.1% gelatin in PBS). The intra-assay and inter-assay coefficients of variation were 10.5% and 10.6% for high reference samples (mean 11.1 pg/mL), and 14.8% and 12.3% for low reference samples (mean 2.6 pg/mL), respectively. The sensitivity of the assay was 0.1 pg/mL.

Plasma progesterone concentrations were determined in duplicate using a commercial solid-phase kit (Coat-A-Count; Diagnostic Products Corporation, Los Angeles, Calif., USA). The range of the standard curve was 0.1 to 40.0 ng/mL. All samples were analyzed in a single assay; the intra-assay coefficients of variation were 4.0% for low reference samples (mean, 0.74 ng/mL) and 1.1% for high reference samples (mean, 8.57 ng/mL).

Statistical Analyses

Statistical analyses were done using the Statistical Analysis System software package (SAS Learning Edition 9.1, 2006; SAS Institute Inc., Cary, N.C., USA). Serial data (hormone and follicle profiles) were analyzed by analysis of variance for repeated measures using the PROC MIXED procedure to determine the effects of device formulation (wax+gel coat, wax, or control), time, and their interactions. When a main effect or interaction was detected, individual comparisons among groups and days were performed using least significant differences (LSD). Single-point measurements (inter-wave interval and dominant follicle diameter at treatment) were compared among groups by analysis of variance. Significance was defined as P≤0.05.

Results

Figure 6:
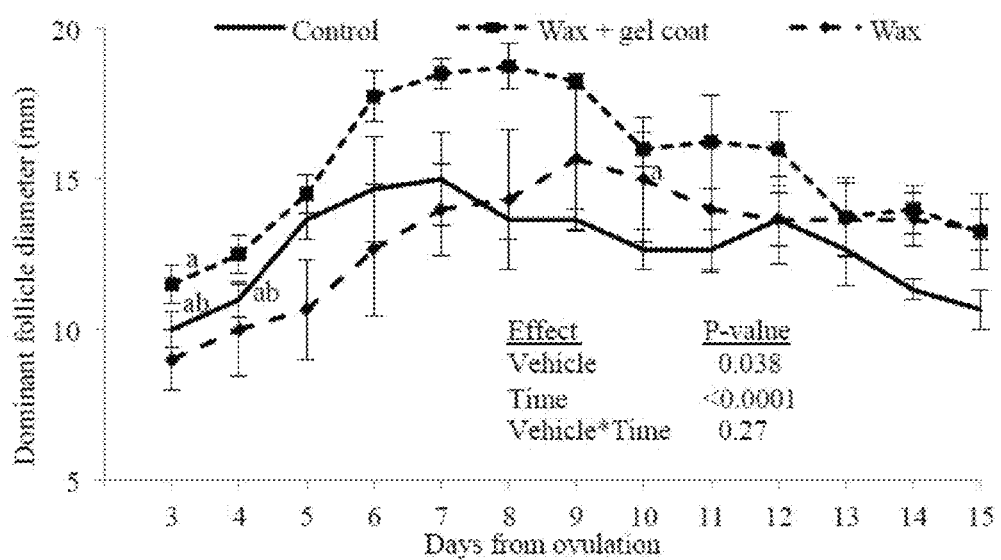
FIG. 6 is a graphs depicting dominant follicle diameter profiles (meantSEM) in heifers treated with a blank intravaginal device (control, n=4), or a letrozole-containing device with wax+gel coat (n=4) or wax only (n=4). Devices were inserted on Day 3 and left in place for 8 days. abc Within days, values with no common superscript are different (P≤50.05).

The intravaginal devices were inserted on Day 3 (Day 0=ovulation) and the mean diameter of the dominant follicle at the time of placement did not differ among groups (Table 6). The day-to-day diameter profile of the dominant follicle during treatment was greatest (P<0.05) in the wax+gel coat group, intermediate (P<0.05) in the wax group, and smallest (P<0.05) in the control group (FIG. 6). Similarly, the inter-wave interval was longest in the wax+gel coat group, intermediate in the wax group, and shortest in the control group (P<0.001, Table).

TABLE 6

Effects of intravaginal devices containing letrozole in wax or wax + gel coat formulations, or no letrozole (blank device, Control) on ovarian function in heifers (mean ± SEM)

|  | Control | Wax + gel coat | Wax |
|---|---|---|---|
| Number of heifers | 4 | 4 | 4 |
| Dominant follicle diameter (mm) at device insertion (Day 3) | 9.7 ± 0.5 | 11.2 ± 0.5 | 9.2 ± 0.1 |
| Inter-wave interval (days) | 10.2 ± 0.4$^a$ | 12.2 ± 0.4$^b$ | 14.3 ± 0.4$^c$ |

$^{abc}$Values with no common superscript are different (P < 0.05)

Figure 7:
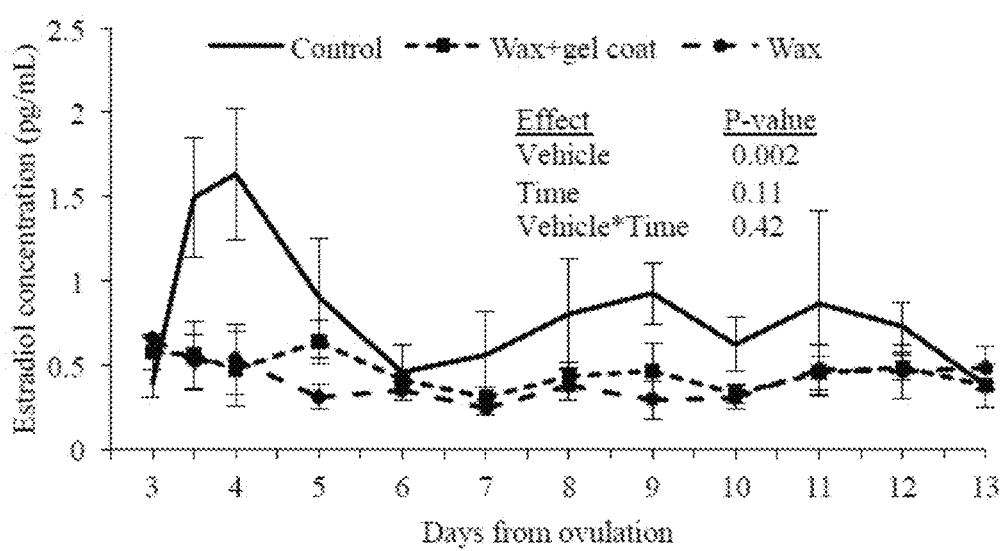
FIG. 7 is a graph depicting plasma estradiol concentrations (mean±SEM) in heifers treated with a blank intravaginal device (control, n=4), or a letrozole-containing device with wax+gel coat (n=4) or wax only (n=4). Devices were inserted on Day 3 and left in place for 8 days.
Figure 8:
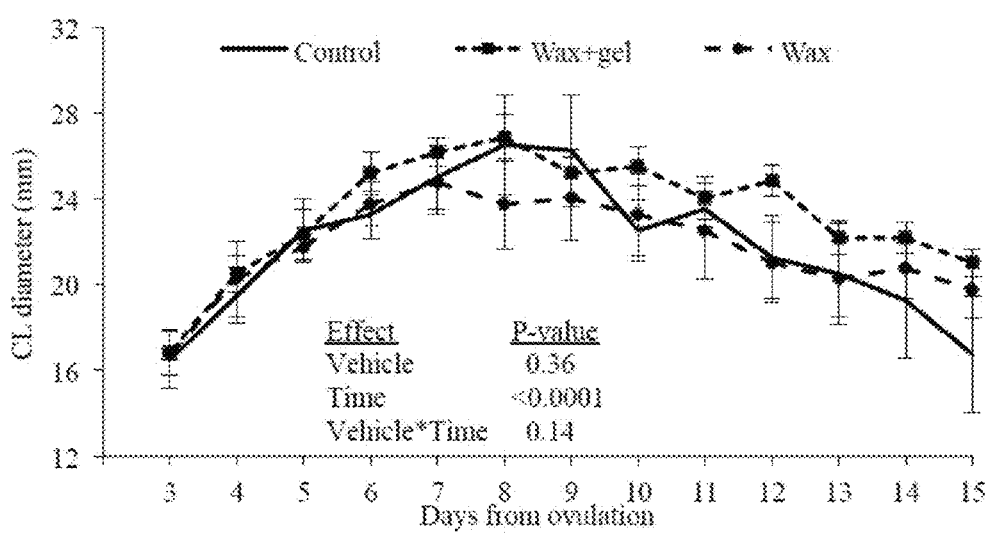
FIG. 8 is a graph depicting corpus luteum diameter profiles (mean±SEM) in heifers treated with a blank intravaginal device (control, n=4), or a letrozole-containing device with wax+gel coat (n=4) or wax only (n=4). Devices were inserted on Day 3 and left in place for 8 days.
Figure 9:
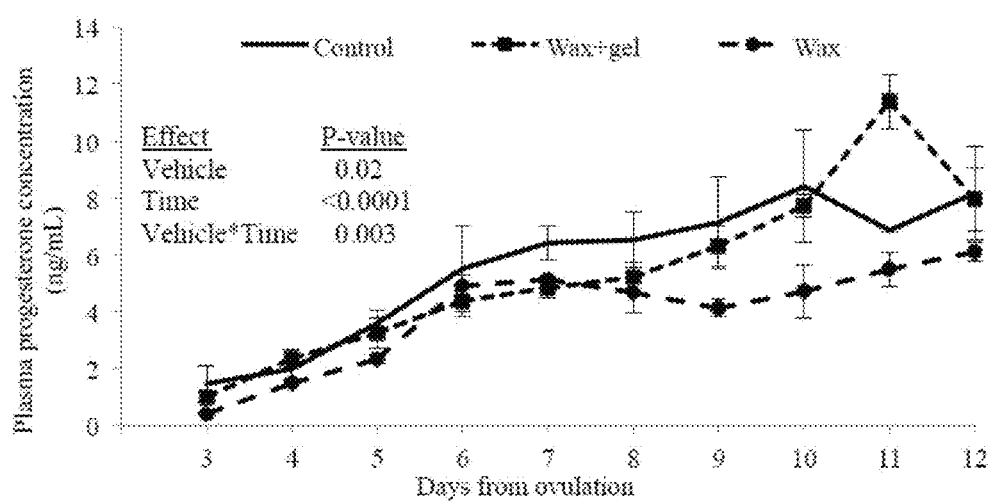
FIG. 9 is a graph depicting plasma progesterone concentrations (mean±SEM) in heifers treated with a blank intravaginal device (control, n=4), or a letrozole-containing device with wax+gel coat (n=4) or wax only (n=4). Devices were inserted on Day 3 and left in place for 8 days.

Plasma estradiol concentrations in the letrozole-treated groups (wax+gel coat and wax) were lower than in the control group from the first post-treatment sample (P=0.002, FIG. 7). No difference was detected in estradiol concentrations between the wax+gel Coat and wax groups. Corpus luteum diameter profiles were not different among groups (P=0.36, FIG. 8). However, progesterone concentrations were lower in the wax group than in the other groups from Day 9 to Day 12 (P<0.05, FIG. 9).

Discussion

Two letrozole-containing formulations were tested in the present study. It was shown that differences in the release and absorption characteristics of the intravaginal formulations induced differential effects on ovarian function in cattle. The only difference in formulation between the two letrozole-containing devices was the presence of a gel coating in one; the total amount of letrozole (3 g) in each device type did not differ. The letrozole-containing gel coating has a lower melting point than the wax-based vehicle, allowing for a rapid liquefaction and absorption of the formulation once the device is inserted into the vagina. The wax plus gel coating formulation resulted in an early rise in plasma letrozole concentrations that reached a steady concentration in plasma by 24 h after device insertion. In contrast, vaginal devices with the wax-only formulation resulted in a slower increase in plasma letrozole concentration that did not reach that of the wax plus gel coat formulation until 60 h after treatment.

A more rapid and sustained growth of the dominant follicle in the group given letrozole in a wax+gel coat device in the present study is consistent with a more rapid and sustained increase in circulating concentration of LH. Prolonged growth of the dominant follicle in the letrozole-treated groups is also consistent with the longer interwave interval seen in these heifers compared to controls; i.e., the period of dominance is reflected in the duration of suppression of emergence of the next follicular wave (Adams et al., 1992).

While not wishing to be bound by theory, it is thought the lesser efficacy of the wax only group in affecting ovarian function suggests that the amount of letrozole required to reduce estradiol concentrations is not necessarily the same as that required to affect ovarian function, or that the method and frequency of estradiol measurements was not sufficient to detect more subtle changes between groups.

Letrozole treatment did not affect CL diameter profiles when compared with the control heifers in the present study, regardless of the formulation used. Compared to controls, plasma progesterone concentration was higher on Day 11 (last day of treatment) in heifers with the wax+gel-based letrozole device but lower on Days 9 to 11 in heifers with the wax-based device. The latter observation was unexpected.

In summary, the vehicle used to deliver letrozole with an intravaginal device (wax+gel coat vs wax alone) differentially affected ovarian function in cattle. Letrozole-impregnated intravaginal devices formulated with a wax base plus a gel coat vehicle were more suitable than wax alone for the application of a letrozole-based protocol for the synchronization of ovulation in cattle. The effects of the device are associated with rapid a elevation in circulating concentrations of letrozole, rapid reduction in estradiol production and resulting increases in dominant follicle growth profile and interwave interval, without adversely affecting progesterone production.

REFERENCES

Adams G P, Matteri R L, Kastelic J P, Ko J C H, Ginther J (1992) Association between surges of follicle stimulating hormone and the emergence of follicular waves in heifers. J Reprod Fert 94:177-188.

Adams P, Kot K, Smith C, Ginther 0 (1993) Selection of a dominant follicle and suppression of follicular growth in heifers. Anim Reprod Sci 30, 259-271.

Al-Fadhli R, Sylvestre C, Buckett W, Tan S L, Tulandi T (2006) A randomized trial of superovulation with two different doses of letrozole. Fertil Steril 85, 161-164.

Bergfelt D R, Kulick L J, Kot K, Ginther O J (2000) Follicular and hormonal response to experimental suppression of FSH during follicle deviation in cattle. Theriogenology 54, 1191-1206.

Bhatnagar A (2007) The discovery and mechanism of action of letrozole. Breast Cancer Res Treat 105, 7-17.

Casper R F (2003) Letrozole: ovulation or superovulation? Fertil Steril 80, 1335-1337.

Cohen M H, Johnson J R, Li N, Chen G, Pazdur R (2002) Approval summary: Letrozole in the treatment of postmenopausal women with advanced breast cancer. Clin Cancer Res 8, 665-669.

Daxenberger A, Ibarreta I D, Meyer H H D (2001) Possible health impact of animal oestrogens in food. Hum Reprod Update 7, 340-355.

Galbraith H (2002) Hormones in international meat production: biological, sociological and consumer issues. Nutr Res Rev 15, 293-314.

Ginther O J, Kot K, Kulick L J, Wiltbank M C (1997) Emergence and deviation of follicles during the development of follicular waves in cattle. Theriogenology 48, 75-87.

Hafs H D, Louis T M, Noden P A, Oxender W D (1974) Control of the estrous cycle with prostaglandin F2{alpha} in cattle and horses. J Anim Sci 38, 10-21.

Harper R, Bennett W A, Cuadra E J, Vaughn C F, Whitworth N S (2008) Effects of GnRH in combination with PGF2 [alpha] on the dynamics of follicular and luteal cells in post-pubertal Holstein heifers. Livest Prod Sci 117, 88-92.

Kastelic J P, Knopf L, Ginther O J (1990) Effect of day of prostaglandin F2[alpha] treatment on selection and development of the ovulatory follicle in heifers. Anim Reprod Sci 23, 169-180.

Kim U-H, Suh G-H, Nam H-W, Kang H-G, Kim I-H (2005) Follicular wave emergence, luteal function and synchrony of ovulation following GnRH or estradiol benzoate in a CIDR-treated, lactating Holstein cows. Theriogenology 63, 260-268.293

Knopf L, KasteliC J P, Schallenberger E, Ginther O J (1989) Ovarian follicular dynamics in heifers: Test of two-wave hypothesis by ultrasonically monitoring individual follicles. Domest Anim Endocrinol 6, 111-119.

Kolok A S, Sellin M K (2008) The environmental impact of growth-promoting compounds employed by the United States beef cattle industry: History, current knowledge, and future directions. In 'Rev Environ Contam Toxicol' pp. 1-30)

Kulick L J, Kot K, Wiltbank M C, Ginther O J (1999) Follicular and hormonal dynamics during the first follicular wave in heifers. Theriogenology 52, 913-921.

Lane E A, Austin E J, Crowe M A (2008) Oestrous synchronisation in cattle—Current options following the EU regulations restricting use of oestrogenic compounds in food-producing animals: A review. Anim Reprod Sci 109, 1-16.

Martinez M F, Kastelic J P, Colazo M G, Mapletoft R J (2007) Effects of estradiol on gonadotrophin release, estrus and ovulation in CIDR-treated beef cattle. Domest Anim Endocrinol 33, 77-90.

Mitwally M F, Casper R F (2001) Use of aromatase inhibitor for induction of ovulation in patients with an inadequate response to clomiphene citrate. Fertil Steril 75, 305-309.

Mitwally M F, Casper R F (2002) Aromatase inhibition for ovarian stimulation: future avenues for infertility management. Curr Opin Obstet Gynecol 14, 255-263.

Mitwally M F, Said T, Galal A, Chan S, Cohen M, Casper R F, Magarelli P C (2008) Letrozole step-up protocol: A successful superovulation protocol. Fertil Steril 89, S23-S24.

Official Journal of the European Union L 262, 14 Oct. 2003. Directive 2003/74/EC of the European Parliament and of the Council on 22 September 2003 amending Council Directive 96/22/EC concerning the prohibition on the use in stockfarming of certain substances having a hormonal or thyristatic action and of beta-agonist. pp. 17-21. Brussels, Belgium, 2003.

Peter A T, Levine H, Drost M, Bergfelt D R (2009) Compilation of classical and contemporary terminology used to describe morphological aspects of ovarian dynamics in cattle. Theriogenology 71, 1343-1357.

Pierson R A, Ginther O J (1987) Reliability of diagnostic ultrasonography for identification and measurement of follicles and detecting the corpus luteum in heifers. Theriogenology 28, 929-936.

Rathbone M J (2012) Delivering drugs to farmed animals using controlled release science and technology. International e-Journal of Science, Medicine & Education (IeJSME) 6, S118-S128.

Requena A, Herrero J, et al. (2008) Use of letrozole in assisted reproduction: A systematic review and meta-analysis. Hum Reprod Update 14, 571-582.

Yapura J, Mapletoft R J, Pierson R, Singh J, Adams G P (2013a) Effect of vehicle and route of administration of letrozole on ovarian function in a bovine model. Reprod Fert Develop (doi.org/10.1071/RD13100).

Yapura J, Mapletoft R J, Pierson R, Singh J, Naile J, Giesy J P, Adams G P (2011) A bovine model for examining the effects of an aromatase inhibitor on ovarian function in women. Fertil Steril 96, 434-438.

Yapura J, Mapletoft R J, Pierson R A, Singh J, Adams G P (2013b) Aromatase inhibitor treatment with an intravaginal device and its effect on pre-ovulatory ovarian follicles in a bovine model, Reprod Biol Endocrin 11:97. (DOT: 10.1186/10.1186/1477-7827-11-97).

Yapura M J, Mapletoft R J, Singh J, Pierson R A, Naile J, Giesy J P, Chang H, Higley E, Hecker, M, Adams G P (2012) Effects of a non-steroidal aromatase inhibitor on ovarian function in cattle. Reprod Fen Develop 24, 631-640

Example III

A study was designed to determine the effect of stage of the estrous cycle on the proportion and the synchrony of ovulation among heifers treated with an aromatase inhibitor-based ovulation-synchronization protocol. Forty-nine heifers at random stages of the estrous cycle were treated intramuscularly with 500 µg of cloprostenol (PGF) followed by 100 µg of GnRH 24 h later to induce luteolysis and ovulation. Heifers were examined daily by transrectal ultrasonography to determine the interval to ovulation, which served as control data for comparison with the synchronizing effect of subsequent aromatase inhibitor treatment in the same animals. At the time of ovulation (Day 0), heifers were assigned randomly to five groups and given an intravaginal device containing 3 g of letrozole for 4 days starting on Days 0, 4, 8, 12, or 16 (n=8-10/group). At the time of device removal, heifers were given PGF followed by GnRH 24 h later. The ovaries were examined daily by ultrasonography from two days before device insertion to 9 days after post-treatment ovulation. Compared to letrozole-free control data, the proportion of heifers that ovulated after letrozole treatment was greater (34/49 vs 42/48, respectively; P<0.05) and the degree of synchrony of ovulation after letrozole treatment was greater (residuals; 28 P<0.01). The diameter of the pre-ovulatory follicle after letrozole treatment was greater in the Day 4 group compared to Day 0 and 16 groups, and intermediate in Day 8 and 12 groups (P<0.001). No difference in ovulation rate was detected among letrozole-treated groups. Although plasma estradiol concentrations did not differ among the letrozole-treated groups, estradiol concentrations in heifers in the Day 0 and 4 groups were lower than their respective controls (P<0.05), while those in the Day 8 and 12 groups did not differ from their respective controls (estradiol concentrations already low in control samples). Corpus luteum diameter profiles and plasma progesterone concentrations were not different among treatment groups. In summary, the addition of a letrozole-impregnated intravaginal device for 4 days, combined with PGF treatment at the time of device removal and GnRH 24 later resulted in an increase in ovulation rate and greater ovulation synchrony compared to non-letrozole treated controls. Results suggest that treatment may be initiated effectively at random stages of the estrous cycle.

Materials and Methods

Cattle

Hereford-cross beef heifers (n=49), 15 to 20 months of age and weighing between 379 and 667 kg (mean of 505±8.6 kg), were chosen from a group of 51 heifers maintained in outdoor pens at the University of Saskatchewan Goodale Research Farm (52° North and 106° West). Heifers were fed alfalfa/grass hay and grain to gain approximately 1.3 Kg per day, and had water available ad libitum during the experimental period from December to February. Heifers were initially examined by transrectal ultrasonography (MyLab5 VET, Canadian Veterinary Imaging, Georgetown, Ontario Canada) to confirm that they were post-pubertal by detection of the presence of a CL [20]. Animal procedures were performed in accordance with the guidelines of the Canadian Council on Animal Care and were approved by University of Saskatchewan Protocol Review Committee.

Treatments and Examinations

Figure 10:
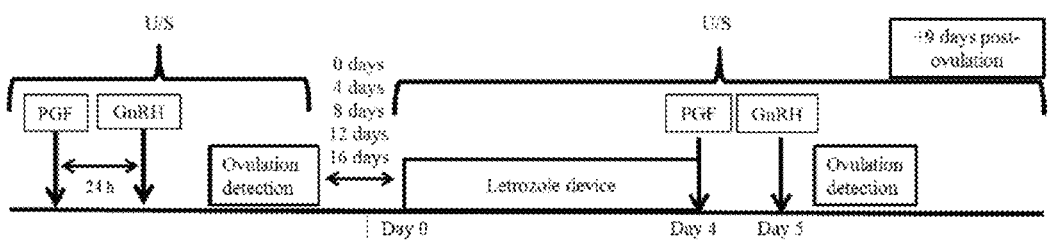
FIG. 10 Schematic representation of treatment schedule. Heifers (n=49) were treated intramuscularly with PGF followed by GnRH 24 h later to induce ovulation. Ovulation (Day 0) was detected by daily ultrasonography. Heifers were given an intravaginal device containing 3 g of letrozole for 4 days starting on Days 0, 4, 8, 12, or 16. At the time of device removal, heifers were given PGF followed by GnRH 24 h later. Ovaries were examined daily by ultrasonography from two days before device insertion to 9 days after the post-treatment ovulation.

Heifers in which a CL was detected during the initial examination (n=49) were treated intramuscularly with 500 pg of cloprostenol (PGF, Estrumate, Schering-Plough Animal Health, Pointe-Claire, QC, Canada) followed by 100 µg of GnRH (Fertiline, Vetoquinol, Lavaltrie, QC, Canada) 24 h later to induce luteolysis and ovulation [21]. Heifers were examined daily by transrectal ultrasonography to determined the interval to ovulation, which served as control data for comparison with the synchronizing effect of subsequent aromatase inhibitor treatment in the same animals. One heifer was excluded for further use due to aggressive behaviour and handling difficulty. At the time of ovulation (Day 0), heifers were assigned randomly to five groups (n=8-10/group) and given an intravaginal device with a wax-based plus gel coat formulation containing 3 g of letrozole (as described in Example 1) for 4 days starting on Day 0, 4, 8, 12, or 16. At the time of device removal, heifers were given 500 µg PGF followed by 100 µg of GnRH 24 h later (FIG. 10).

Ultrasound examinations were performed daily from two days before device insertion to 9 days after post-treatment ovulation. Observations from ultrasound examinations were recorded on a sketch sheet in which each ovary and its structures (CL and follicles a 4 mm in diameter) were represented by size and location [22]. Ovulation was defined as the disappearance of a follicle mm between successive examinations after GnRH treatment, and was confirmed by the subsequent detection of a CL [20]. The time of follicular wave emergence was defined as the day of ovulation, or retrospectively as the day when the dominant follicle was first identified at a diameter of 4 to 5 mm [23, 24]. If the dominant follicle was not identified until it reached 6 or 7 mm, the previous day was considered day of wave emergence [25]. The dominant follicle of a wave was defined as the largest antral follicle of the wave [26]. The day of onset of follicular and luteal regression was defined as the first day of an apparent progressive decrease in follicular and luteal diameters, respectively [23].

Collection of Blood Samples and Hormone Assays

Blood samples were collected by coccygeal venipuncture into 10 mL heparinized vacuum tubes (Becton Dickinson Vacutainer Systems, Franklin Lakes, N.J., USA). Samples were collected at the time of device removal for estradiol measurement, and at 3, 6 and 9 days following the post-treatment ovulation to determine progesterone concentrations: Additionally, blood samples were collected on Days 4, 8, 12, and 16 from heifers included in Group 16 (Day 0=ovulation) to serve as control data for comparison of estradiol concentrations at the time of device removal in other treatment groups (Groups 0, 4, 8, and 12). As such, Group 16 did not have a control sample for comparison of estradiol concentrations at the time of device removal. Blood samples were centrifuged at 1500×g for 20 min and plasma was separated and stored in plastic tubes at −20° C. until assayed.

Plasma concentrations of estradiol were determined using a commercial radioimmunoassay kit (Double Antibody Estradiol; Diagnostic Products, Los Angeles, Calif., USA). The procedure was carried out in the Department of Animal Health and Biomedical Sciences, University of Wisconsin-Madison, as described [27, 28], with the following modifications: Standards (0.78-100 pg/mL) were prepared in steroid-free (charcoal-treated) bovine plasma. The standards (250 µL in duplicate) and plasma samples (500 µL in duplicate) were extracted with 3 mL of diethyl ether, frozen in a dry-ice/methanol bath, decanted into assay tubes, and dried overnight under a fume hood. The dried samples and standards were re-suspended with 100 µL of assay buffer (0.1% gelatin in PBS). The intra- and inter-assay coefficients of variation were 10.5 and 10.6%, respectively for high reference samples (mean 11.1 pg/mL), and 14.8 and 12.3%, respectively for low reference samples (mean 2.6 pg/mL). The sensitivity of the assay was 0.1 pg/mL.

Plasma progesterone concentrations were determined in duplicate using a commercial solid-phase kit (Coat-A-Count; Diagnostic Products Corporation, Los Angeles, Calif., USA). The range of the standard curve was 0.1 to 40.0 ng/mL. Samples were analyzed in a single assay. The intra-assay coefficient of variation was 4.0% for low reference samples (mean, 0.74 ng/mL) and 1.1% for high reference samples (mean, 8.57 ng/mL).

Statistical Analyses

Statistical analyses were done using the Statistical Analysis System software package (SAS Learning Edition 9.1, 2006; SAS Institute Inc., Cary, N.C., USA). Time-series hormone data and follicular diameter profiles were analyzed by analysis of variance for repeated measures using the PROC MIXED procedure to determine the effects of day of treatment (0, 4, 8, 12, and 16), time, and their interactions. Individual time-point comparisons among groups were compared using the least significant difference (LSD) test. Single-point measurements (dominant follicle diameter at device insertion, pre-ovulatory follicle diameter, CL diameter 9 days after the post-treatment ovulation and interval from GnRH treatment to ovulation) were analyzed by one-way analysis of variance. The proportion of heifers that ovulated were compared by Chi-Square test. The degree of synchrony among groups was compared by analysis of variance of the residuals of the interval from GnRH to ovulation. Significance was defined as P≤0.05.

Results

Ovarian Function

The mean diameter of the dominant follicle at the time of device placement was larger in heifers in Groups 4 and 12 compared to Groups 0 and 16, and intermediate in the Group 8 (Table 7). Similarly, the maximum diameter of the ovulatory follicle after letrozole treatment was greater in Group 4 compared to Groups 0 and 16, and intermediate in Groups 8 and 12 (Table 7). The day-to-day dominant follicle diameter profiles during treatment were larger in Group 4 compared to Groups 0 and 16, and intermediate in Groups 8 and 12 (P<0.001).

TABLE 7

Effects of a letrozole-containing intravaginal device in combination with PGF and GnRH on ovarian function in heifers (mean ± SEM).

| Letrozole treatment initiated on: | Dominant follicle diameter (mm) | | | CL diameter (mm) at 9 days post-ovulation |
|---|---|---|---|---|
| | At day of device placement | | At day before ovulation | |
| Day 0 (n = 10) | 5.7 ± 0.35$^a$ | | 12.8 ± 0.58$^a$ | 20.9 ± 1.09$^a$ |
| Day 4 (n = 9) | 11.9 ± 0.59$^b$ | | 16.4 ± 0.78$^b$ | 25.2 ± 1.65$^{ab}$ |
| Day 8 (n = 8) | 7.2 ± 1.76$^{abc}$ | | 14.5 ± 0.83$^{ab}$ | 20.8 ± 1.88$^{ab}$ |
| Day 12 (n = 11) | 10.1 ± 0.74$^{bc}$ | | 14.2 ± 0.48$^{ab}$ | 21.7 ± 0.99$^{ab}$ |
| Day 16 (n = 10) | 6.0 ± 1.56$^{ac}$ | | 11.7 ± 0.59$^a$ | 26.8 ± 2.69$^b$ |

$^{abc}$Within columns, values with no common superscript are different (p < 0.05)

The percentage of heifers that ovulated after GnRH treatment was higher when a letrozole-releasing intravaginal device was added to the PGF plus GnRH (control) protocol (P=0.05, Table 28). No effect of group on synchrony of ovulation was detected; therefore, data were combined into a single letrozole group. The interval from GnRH treatment to ovulation was longer in the control group compared to the combined letrozole-treated groups (P=0.008, Table 8). The degree of ovulation synchrony was greater in the combined letrozole-treated groups than in the control group (P=0.01. Tables 8 and 9). The distribution of the ovulations in the letrozole-treated and control groups is summarized in Table 9.

TABLE 8

Effect of addition of letrozole to a PGF-GnRH-protocol on ovulation in heifers.

| | Control | Letrozole | P-value |
|---|---|---|---|
| Proportion that ovulated | 34/49 (69.4%) | 42/48 (87.1%) | 0.05 |
| Days from GnRH treatment to ovulation | 2.4 ± 0.18 | 1.9 ± 0.08 | 0.01 |
| Degree of synchrony* | 0.68 ± 0.13 | 0.24 ± 0.07 | 0.01 |

*Analysis of the residuals of the interval from GnRH to ovulation

TABLE 9

Distribution of ovulation in heifers treatment with a letrozole-releasing intravaginal device for 4 days beginning on different days of the estrous cycle (Day 0 = pre-treatment ovulation), followed by a luteolytic dose of prostaglandin and an ovulation-inducing dose of GnRH.

| Letrozole treatment initiated on: | Ovulation in relation to GnRH | | |
|---|---|---|---|
| | Before* | Synchronized* | Ovulation failure* |
| Day 0 | 0 | 10 | 0 |
| Day 4 | 3 | 7 | 0 |
| Day 8 | 0 | 7 | 1 |
| Day 12 | 0 | 10 | 1 |
| Day 16 | 3 | 5 | 1 |
| Letrozole groups combined | 6 (12%)$^a$ | 39 (81%)$^a$ | 3 (6%)$^a$ |
| Control (pre-letrozole data) | 7 (14%)$^a$ | 28 (57%)$^b$ | 14 (28%)$^b$ |

Plasma Estradiol Concentrations

Figure 11:
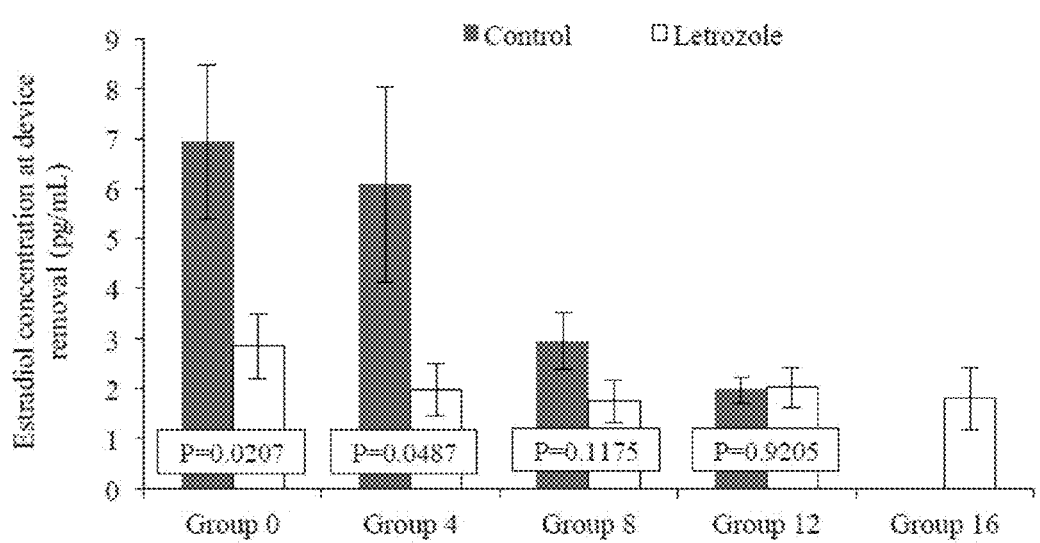
FIG. 11 Plasma estradiol concentration (mean±SEM) at letrozole device removal in heifers treated with a 4-day regimen of letrozole intravaginally compared to untreated controls. Devices were placed on Days 0 (Group 0, n=10), 4 (Group 4, n=10), 8 (Group 8, n=8), 12 (Group 12, n=11) or 16 (Group 16, n=9; Day 0=ovulation). Control samples were obtained from heifers in the Group 16 at Days 4, 8, 12 and 16, prior to treatment with letrozole on Day 16. Hence, Group 16 lacked of a control group at device removal.

Plasma estradiol concentrations at the time of device removal in Groups 0, 4, 8, and 12 were compared to samples collected from heifers in Group 16 at equivalent time points before letrozole treatment was initiated in that group. Group 16 lacked a comparable control group due to the experimental design. Estradiol concentrations at device removal were lower in Groups 0 and 4, compared to their respective controls (P=0.02 and P=0.05, respectively; FIG. 11) and estradiol concentrations tended to be lower following letrozole treatment in Group 8 (P=0.1, FIG. 11). Estradiol concentrations were low in Group 12 and not different from Day 12 controls (P=0.9, FIG. 11).

Corpus Luteum Diameter and Function

Figure 12:
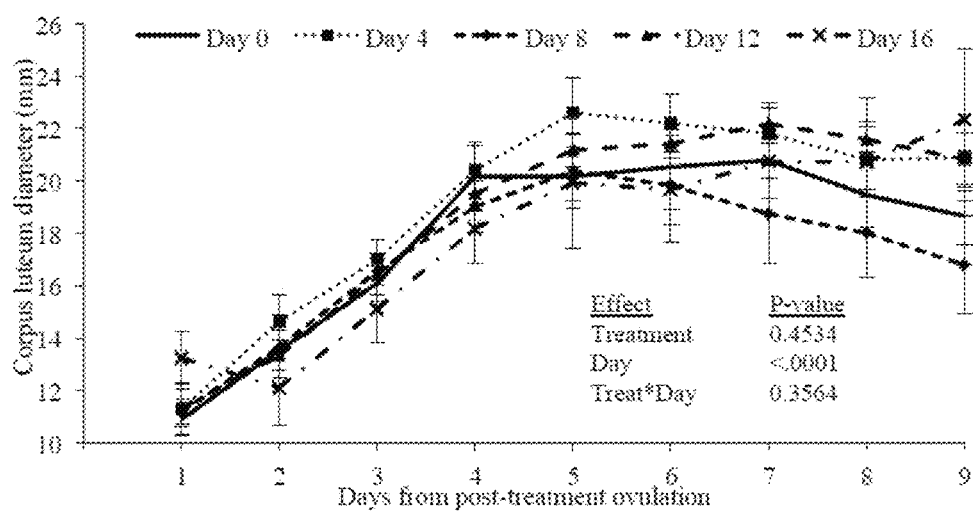
FIG. 12 Corpus luteum diameter profiles (mean±SEM) in heifers after treatment with letrozole-releasing intravaginal device for 4 days followed by PGF at device removal and GnRH 24 h later. Devices were placed on Days 0 (Group 0, n=10), 4 (Group 4, n=10), 8 (Group 8, n=8), 12 (Group 12, n=11) or 16 (Group 16, n=9; Day 0=ovulation)
Figure 13:
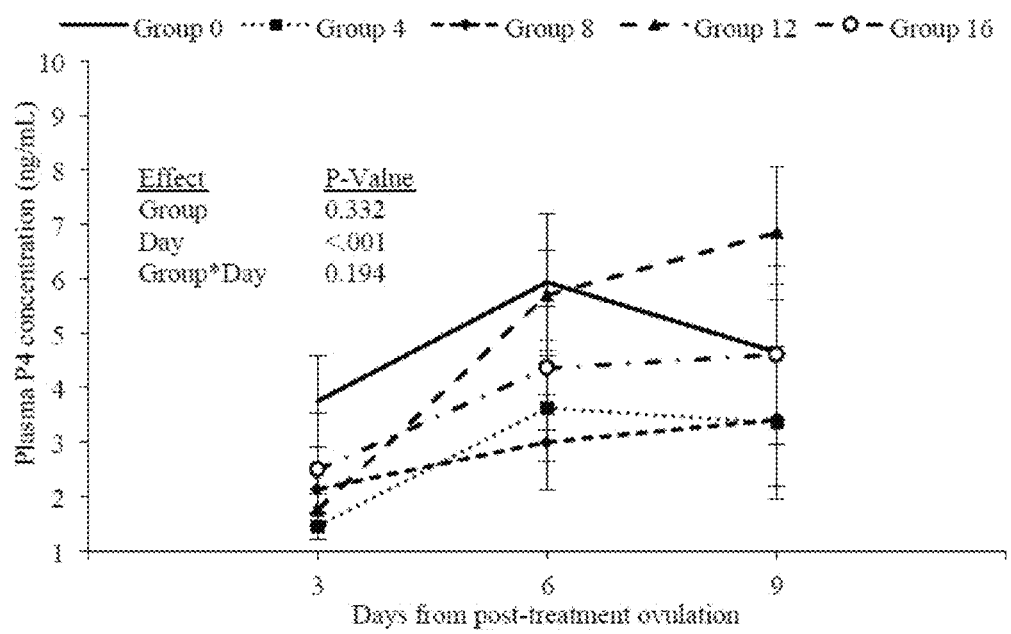
FIG. 13 is a graph depicting plasma progesterone (P4) profiles (mean±SEM) in heifers after treatment with letrozole-releasing intravaginal device for 4 days followed by PGF at device removal and GnRH 24 h later. Devices were placed on Days 0 (Group 0, n=10), 4 (Group 4, n=9), 8 (Group 8, n=8), 12 (Group 12, n=11) or 16 (Group 16, n=10; Day 0=ovulation).

Corpus luteum diameter profiles were not different among treatment groups (P=0.45, FIG. 12). Similarly, progesterone concentrations were not different among treatment groups during the 9 days following ovulation (P=0.33, FIG. 13).

Two subsets of animals were identified based on lifespan of the CL resulting from the post-treatment ovulations. One group included heifers with CL of normal lifespan which were 209 actively growing or static 9 days after the post-treatment ovulation (7/10 in Group 0, 4/10 in Group 4, 4/8 in Group 8, 10/11 in Group 12, and 5/9 in Group 16). The remaining heifers had CL of short lifespan which were either regressing or had already regressed by 9 days after the post-treatment ovulation [29]. Corpus luteum diameter profiles were not different among treatment groups within the two sub-populations (P=0.62 and P=0.41, for normal and short lifespan CL, respectively). Similarly, progesterone concentrations were not different among treatment groups within each sub-population during the observational period (P=0.88 and P=0.40, for normal and short lifespan CL, respectively).

Discussion

The data presented herein demonstrate that extended letrozole treatment using intravaginal devices, combined with a single PGF and GnRH treatment, increases the percentage of heifers that ovulated and the synchrony of ovulation, regardless the stage of the estrous cycle at initiation of the protocol.

The percentage of heifers that ovulated was increased by the addition of a 4-day regimen of letrozole to a PGF plus GnRH protocol as compared to PGF plus GnRH alone (87.1% vs 69.4%, respectively). This increase in ovulatory response and synchrony of ovulation after the addition of letrozole may involve more follicles responding to the GnRH treatment and a decrease in early ovulations (ovulations that occurred prior to GnRH treatment). While not wishing to be bound by theory, in addition to promoting follicular growth, letrozole treatment likely prolonged the lifespan of the static dominant follicles that otherwise would have become atretic by the time of GnRH treatment [16-18]. The improved ovulatory response and synchrony of ovulation after GnRH indicated that letrozole could be applied for the development of a FTAI protocol.

The impact of duration of dominance of the pre-ovulatory follicle on timing of ovulation and fertility has been reported [30, 31]. Prolonged dominance of the ovulatory follicle has been associated with reduced pregnancy rates. The decrease in fertility was more profound after 9 days of dominance (35 to 70% reduction in pregnancy rates) compared to after 2 days of dominance [30]. Duration of dominance is related to increased LH levels [32] and early activation of oocytes (resumption of meiosis) has been associated with decreased fertility [30, 33-35]. During the present study, designed a minimal duration of follicle dominance in the pre-ovulatory follicles by adjusting the length of letrozole treatment to 4 days. The duration of dominance of the pre-ovulatory follicles among groups was estimated based on the average day of emergence of the follicle that became the ovulatory follicle—follicles typically reach dominant status by 3 days post-wave emergence (2.8 days) [36]. It would follow that the duration of dominance in Groups 0 and 4 were 1 and 5 days, respectively. Group 8 contained heifers that would have had follicles from the first follicular wave (n=4) and heifers with follicles originating from the second follicular wave (n=4). Hence, heifers in this group would have had follicles in which dominance would have been 1 days or 9 days at the time of ovulation. Group 12 should have had follicles that originated from only the second wave, and would have been dominant for about 1 days before ovulation. Group 16 would have had follicles originating from either the second or third wave of follicular growth and the duration of dominance in this group would have been 1 and 9 days (4 and 6 heifers, respectively). As evidenced by these numbers, heifers between Days 7 and 9 (Day 8±1) and between Days 15 and 17 (Day 16±1; Day 0=ovulation) would be at risk of developing an ovulatory follicle that had been dominant for approximately 9 days and would likely have an aged and/or prematurely activated oocyte. However, we must consider the possibility that increased LH secretion (caused by letrozole treatment [17, 19]) may also cause premature activation of oocytes and a reduction in fertility, even if duration of dominance of the pre-ovulatory follicle was within normal range (1 to 5 days, [35]).

Estradiol concentrations were reduced in heifers in Groups 0 and 4, tended to be reduced in Group 8, while Group 12 did not differ from their respective controls. Considering that estradiol concentration at device removal did not differ among letrozole-treated groups and averaged 2.1±0.24 pg/mL, the differences noted between letrozole-treated heifers relative to their controls were attributed to changes in estradiol concentration in the control samples. Estradiol concentration in the control heifers Days 4, 8, 12 and 16 were consistent with those obtained previously: basal estradiol concentrations have been reported to be around 2 pg/mL, with a small rise between Days 4 and 7 post-LH peak and no significant changes in estradiol concentration thereafter until the next pre-ovulatory estradiol rise [37]. While not wishing to be bound by theory, it is possible, however, that the presence of a newly recruited wave of follicular development (third wave) was responsible for the low estradiol concentration observed in the control heifers on Day 16. In other words, the high estradiol concentration expected with the presence of a growing (estrogen-active) follicle from the second wave (potentially an ovulatory wave) may have been tampered by the coexistence of atretic (estrogen-inactive) follicles from the second follicular wave with newly recruited follicles which have not yet reach their maximal estrogen production potential.

The effect of letrozole treatment on CL lifespan in this study was unexpected. Thirty out of 48 (62.5%) heifers treated had CL considered to be of normal diameter at last observation (9 days post-letrozole treatment ovulation), while 18 (37.5%) heifers underwent luteolysis prior to the last observation at 9 days after ovulation. Progesterone production was not affected by group and its profile corresponded to CL lifespan (i.e., normal vs short lifespan). The reason for these differences on CL lifespan within groups remains unclear. There appeared to be no relationship between duration of follicular dominance and lifespan of the resulting CL. Short-lived CL have been described following hCG-induced ovulation of the dominant follicle of the first follicular wave in cattle, suggesting that pre-ovulatory changes intrinsic to the treatment may be responsible for the abnormal CL function [45].

While not wishing to be bound by theory, another possible explanation for the observed short lifespan CL is related with the occurrence of early luteolysis. Short luteal phases in 33% of cows [46] and 47% of heifers have been reported

[47] when GnRH treatment was given 24 h after PGF. The short luteal phases were related to early release of PGF2α from the endometrium [48]. Reduced estradiol concentration during the proestrus has also been linked to short luteal lifespan. It has been hypothesized that high estradiol concentrations during proestrus are needed in order to induce an adequate number of progesterone receptors, thus allowing progesterone to regulate the uterine secretion of PGF [29, 49]. Therefore, low estradiol concentration induced by letrozole treatment may impair the inhibitory effect that progesterone has on PGF secretion by allowing the increase in number of estrogen and oxytocin receptors in the endometrium and early release of PGF2α[50].

In summary, the addition of a letrozole-impregnated intravaginal device for 4 days, combined with PGF treatment at device removal and GnRH 24 h post-device removal increased the percentage of ovulations and synchrony of ovulation in cattle, regardless the stage of the estrous cycle at initiation of treatment. Reduced luteal lifespan after letrozole treatment was unexpected and requires further investigation in order to elucidate the mechanism responsible for this observation.

We conclude that the addition of letrozole to a GnRH plus PGF protocol is useful to increase the number of animals ovulating and the synchrony of ovulation.

REFERENCES

1. Thibier, M. and H. G. Wagner, World statistics for artificial insemination in cattle. Livest Prod Sci, 2002, 74: p. 203-212.
2. Thibier, M. The worldwide activity in farm animals embryo transfer. Data Retrieval Committee Statistics of Embryo Transfer-Year 2007 2008 [cited: Available from: http://www.iets.org/pdf/December2008.pdf.
3. Mapletoft, R. J. and K. McDermott. Summary of Embryo Transfer Activity in Canada for 2009. 2009 [cited; Available from: http://www.ceta.ca/pdfs/2009-ET-Activity-in-Canada.pdf
4. Bo, G. A., et al., Exogenous control of follicular wave emergence in cattle. Theriogenology,1995. 43(1): p. 31-40.
5. Bo, G. A., et al., Ovarian follicular wave emergence after treatment with progestogen and estradiol in cattle. Anim Reprod Sci, 1995. 39(3): p. 193-204.
6. Bridges, P. J., et al., Follicular growth, estrus and pregnancy after fixed-time insemination in beef cows treated with intravaginal progesterone inserts and estradiol benzoate. Theriogenology, 1999. 52(4): p. 573-583.
7. Martinez, M. F., et al., Induction of follicular wave emergence for estrus synchronization and artificial insemination in heifers. Theriogenology, 2000. 54(5): p. 757-769,
8. Colazo, M. G., et al., Fertility following fixed-time AI in CIDR-treated beef heifers given GnRH or estradiol cypionate and fed diets supplemented with flax seed or sunflower seed. Theriogenology, 2004, 61(6): p. 1115-1124.
9. Lane, E. A., E. J. Austin, and M. A. Crowe, Oestrous Synchronisation in cattle—Current options following the EU regulations restricting use of oestrogenic compounds in food-producing animals: A review. Anim Reprod Sci, 2008. 109(1-4): p. 1-16.
10. Official Journal of the European Union, L 262, 14 Oct. 2003. Directive 2003/74/EC of the European Parliament and of the Council on 22 September 2003 amending Council Directive 96/22/EC concerning the prohibition on the use in stockfarming of certain substances having a hormonal or thyristatic action and of beta-agonist. pp. 17-21. Brussels, Belgium, 2003.
11. Cohen, M. H., at al., Approval summary: Letrozole in the treatment of postmenopausal women with advanced breast cancer. Clin Cancer Res, 2002. 8(3): p. 665-669.
12. Requena, A., et al., Use of letrozole in assisted reproduction: A systematic review and meta-analysis. Hum Reprod Update, 2008. 14(6): p. 571-582.
13. Mitwally, M. F. and R. F. Casper, Aromatase inhibition for ovarian stimulation: future avenues for infertility management. Curr Opin Obstet Gynecol, 2002. 14(3): p. 255-263.
14. Mitwally, M. F, and R. F. Casper, Use of aromatase inhibitor for induction of ovulation in patients with an inadequate response to clomiphene citrate. Fertil Steril, 2001. 75: p. 305-309.
15. Rathbone, M. J., Delivering drugs to farmed animals using controlled release science and technology, IeJSME, 2012. 6(Suppl 1): p. S118-S128.
16. Yapura, J., et al., Aromatase inhibitor treatment with an intravaginal device and its effect on pre-ovulatory ovarian follicles in a bovine model. 2013, Reproductive Biology and Endocrinology 11:97. (DOI: 10.1186/10.1186/1477-7827-11-97).
17. Yapura, J., et al., A bovine model for examining the effects of an aromatase inhibitor on ovarian function in women. Fertil Steril, 2011. 96(2): p. 434-438.
18. Yapura, J., et al., Effect of vehicle and route of administration of letrozole on ovarian function in a bovine model. Reprod Fert Develop, 2013. (doi.org/10.1071/RD13100).
19. Yapura, M. J., et al., Effects of a non-steroidal aromatase inhibitor on ovarian function in cattle. Reprod Fert Develop, 2011. 24(4): p. 631-640.
20. Pierson, R. A. and O. J. Ginther, Reliability of diagnostic ultrasonography for identification and measurement of follicles and detecting the corpus luteum in heifers. Theriogenology, 1987. 28(6): p. 929-936,
21. Hafs, H. D., et al., Control of the estrous cycle with prostaglandin F2{alpha} in cattle and horses. J Anim Sci, 1974. 38(Supplement_1): p. 10-21.
22. Knopf, L., et al., Ovarian follicular dynamics in heifers: Test of two-wave hypothesis by ultrasonically monitoring individual follicles. Domest Anim Endocrinol, 1989. 6(2): p. 111-119.
23. Adams, P., et al., Selection of a dominant follicle and suppression of follicular growth in heifers. Anim Reprod Sci, 1993. 30(4): p. 259-271.
24. Ginther, O. J., et al., Emergence and deviation of follicles during the development of follicular waves in cattle. Theriogenology, 1997. 48(1): p. 75-87.
25. Kastelic, J. P., L. Knopf, and O. J. Ginther, Effect of day of prostaglandin F2[alpha] treatment on selection and development of the ovulatory follicle in heifers. Anim Reprod Sci, 1990. 23(3): p, 169-180.
26. Peter, A. T. et al., Compilation of classical and contemporary terminology used to describe morphological aspects of ovarian dynamics in cattle. Theriogenology, 2009. 71(9): p. 1343-1357.
27. Bergfelt, D. R., et al., Follicular and hormonal response to experimental suppression of FSH during follicle deviation in cattle. Theriogenology, 2000. 54(8): p. 1191-1206.
28. Kulick, L. J., et al., Follicular and hormonal dynamics during the first follicular wave in heifers. Theriogenology, 1999. 52(5): p. 913-921.
29. Garverick, H. A., W. G. Zollers, and M. F. Smith, Mechanisms associated with corpus luteum lifespan in animals having normal or subnormal luteal function. Anim Reprod Sci, 1992. 28(1): p. 111-124.

30. Austin, E. J., et al., Effect of duration of dominance of the ovulatory follicle on onset of estrus and fertility in heifers. J Anim Sci, 1999. 77(8): p. 2219-26.

31. Vasconcelos, J. L. M., et al., Synchronization rate, size of the ovulatory follicle, and pregnancy rate after synchronization of ovulation beginning on different days of the estrous cycle in lactating dairy cows. Theriogenology, 1999. 52(6): p. 1067-1078.

32. Taft, R., N. Ahmad, and E. K. Inskeep, Exogenous pulses of luteinizing hormone cause persistence of the largest bovine ovarian follicle. Journal of Animal Science, 1996. 74(12): p, 2985-91.

33. Revah, I. and W. R. Butler. Prolonged dominance of follicles and reduced viability of bovine oocytes. J Reprod Fertil, 1996. 106(1): p. 39-47.

34. Taft, R., N. Ahmad, and E. K. Inskeep, Exogenous pulses of luteinizing hormone cause persistence of the largest bovine ovarian follicle. J Anim Sci, 1996. 74(12): p. 2985-91, 35. Mihm, M., et al., Effect of dominant follicle persistence on follicular fluid oestradiol and inhibin and on oocyte maturation in heifers. J Reprod Fert, 1999. 116(2): p. 293-304.

36. Ginther, O. J., et al., Selection of the dominant follicle in cattle. Biol Reprod, 1996. 55(6): p. 1187-1194.

37. Kaneko, H., et al., Changes in Plasma Concentrations of Immunoreactive Inhibin, Estradiol and FSH Associated with Follicular Waves during the Estrous Cycle of the Cow. J Reprod Dev, 1995. 41(4): p. 311-320.

38. Zelinski-Wooten, M. B., et al., Administration of an aromatase inhibitor during the late follicular phase of gonadotropin-treated cycles in rhesus monkeys: effects on follicle development, oocyte maturation, and subsequent luteal function. J Clin Endocrinol Metab, 1993. 76(4): p. 988-95.

39. Beker, A. R. C, L., B. Colenbrander, and M. M. Bevers, Effect of 17 beta-estradiol on the in vitro maturation of bovine oocytes. Theriogenology, 2002, 58(9): p. 1663-1673.

40. Beker-van Woudenberg, A. R., et al., Estradiol and Its Membrane-Impermeable Conjugate (Estradiol-Bovine Serum Albumin) During in Vitro Maturation of Bovine Oocytes: Effects on Nuclear and Cytoplasmic Maturation, Cytoskeleton, and Embryo Quality. Biol Reprod, 2004, 70(5): p. 1465-1474.

41. Fukushima, M. and Y. Fukui, Effects of gonadotropins and steroids on the subsequent fertilizability of extrafollicular bovine oocytes cultured in vitro. Anim Reprod Sci, 1965 9(4): p. 323-332.

42. Endo, M., et al., Estradiol supports in vitro development of bovine early antral follicles. Reproduction, 2013. 145(1): p. 85-96.

43. Fatum, M., et al., Is estradiol mandatory for an adequate follicular and embryo development? A mouse model using aromatase inhibitor (anastrozole). J Assist Reprod Gen, 2006. 23(11-12): p. 407-412.

44. Roark, D. B. and H. A. Herman, Physiological and histological phenomena of the bovine estrual cycle with special reference to vaginal cervical secretions. Research Bulletin. Missouri Agricultural Experiment Station, 1950 (455).

45. Sianangama, P. C. and R. Rajamahendran, Characteristics of corpus luteum formed from the first wave dominant follicle following hCG in cattle. Theriogenology, 1996. 45(5): p. 977-990.

46. Taponen, J., et al., Short estrous cycles and estrous signs after premature ovulations induced with cloprostenol and gonadotropin-releasing hormone in cyclic dairy cows. Theriogenology, 2002. 58(7): p. 1291-1302.

47. Rantala, M. H., T. Katila, and J. Taponen, Effect of time interval between prostaglandin F 2 alpha and GnRH treatments on occurrence of short estrous cycles in cyclic dairy heifers and cows. Theriogenology, 2009. 71(6): p. 930-938.

48. Taponen, J., et al., Premature prostaglandin F2ë± secretion causes luteal regression in GnRH-induced short estrous cycles in cyclic dairy heifers. Theriogenology, 2003. 60(2): p. 463 379-393. 49. Ottobre, J. S., et al., Aspects of regulation of uterine secretion of prostaglandins during the oestrous cycle and early pregnancy. Anim Reprod Sci, 1984. 7(1â€"3): p. 75-100.

50. Mann, G. E. and G. E. Lamming, The role of suboptimal preovulatory oestradiol secretion in the aetiology of premature luteolysis during the short oestrous cycle in the cow. Anim Reprod Sci, 2000. 64(3): p. 171-180.

51. Pursley, J. R., M. O., Mee, and M. C. Wiltbank, Synchronization of ovulation in dairy cows using PGF2 [alpha] and GnRH. Theriogenology, 1995. 44(7): p. 915-923.

52. Macmillan, K. L. and W. W. Thatcher, Effects of an agonist of gonadotropin-releasing hormone on ovarian follicles in cattle, Biol Reprod, 1991. 45(6): p. 883-889.

Protcols

Use of Letrozole to Control Ovarian Dynamics in Cattle

In some examples, a lipid-based formulation as described herein, a waxed-based formulation as described herein, a lipid-based formulation with a gel coat, and/or a waxed-based formulation with a gel coat as described herein, comprising an aromatase inhibitor (such as letrozole), has the capability to lengthen the lifespan and period of dominance of the extant dominant follicle in the ovaries of cattle. A luteotrophic effect of letrozole in cattle as also been shown. Letrozole may be used to control ovarian dynamics in cattle in respect of (i) herd synchronization, (ii) improved fertility and (iii) twinning.

Herd Synchronization

In one example, a lipid-based formulation as described herein, a waxed-based formulation as described herein, a lipid-based formulation with a gel coat, and/or a waxed-based formulation with a gel coat as described herein, comprising an aromatase inhibitor (such as letrozole), may be applied on random days of the estrous cycle to Induce the formation of a persistent dominant follicle and delay wave emergence by preventing spontaneous ovulations (i.e., inhibiting the pre-ovulatory rise in estradiol and potentially delaying luteolysis). On Day 5 (Day 0=day of treatment), a luteolytic dose of PGF is given to induce regression of the corpus luteum (CL), followed on Day 7 by an ovulatory dose of GnRH or pLH to synchronize ovulation. Insemination (e.g., artificial insemination) at detected estrus or following treatment with GnRH or pLH on Day 6 or 7 to synchronize ovulation (fixed-time artificial insemination [FTAI] on Day 7-7.5).

In another example, a prostaglandin such as Lutalyse is administered (e.g., about 5 mL Lutalyse® administered intramuscularly) followed (i.e., 48 h) by administration of a lipid-based formulation as described herein, a waxed-based formulation as described herein, a lipid-based formulation with a gel coat, and/or a waxed-based formulation with a gel coat as described herein, comprising an aromatase inhibitor (such as letrozole), to synchronize individual cows of a herd with respect to the time of occurrence of estrus, ovulation, or both.

For the purposes of ovarian superovulation and embryo transfer, superstimulatory treatments may be initiated 36 to 46 hours after letrozole and GnRH/pLH treatment.

In another example of superovulation, a lipid-based formulation as described herein, a waxed-based formulation as described herein, a lipid-based formulation with a gel coat, and/or a waxed-based formulation with a gel coat as described herein, comprising an aromatase inhibitor (such as letrozole), is administered at the beginning of follicular wave emergence in a cow, concurrent with a conventional superstimulatory treatment protocol that is also initiated at wave emergence.

Synchronization of ovulation in a mare is notoriously difficult, owing primarily to a prolonged and variable follicular phase. Various combinations of reproductive steroids (progestogens and estrogens), prostaglandin-F2a (PGF, native and analogues), human chorionic gonadotropin (hCG) and gonadotropin-releasing hormone (GnRH, native and analogues) have been used to control follicular development and the time of ovulation for basic and applied purposes during the spring transition, estrous cycle and postpartum period in mares [review in 63].

From an applied perspective, the most common objectives are to coordinate the expected time of ovulation with insemination and align ovulations in recipient mares with donor mares in an embryo transfer program. Regimens of progestogens (injectable, oral and intravaginal) and PGF used alone or in combination have limited control on follicular development and, therefore, are primarily used to inhibit or delay ovulation. The hormonal regimen used most often to control both follicular development and ovulation is a combination of progesterone plus estradiol (P&E). The regimen involves intramuscular administration of P&E for 10 d beginning at unknown or random stages of the estrous cycle, PGF on the last day of steroid treatment and hCG or GnRH when the largest follicle reaches >35 mm.

According to seminal studies done in the 1980's, this steroidal regimen without hCG treatment resulted in ovulation synchrony among mares ranging from 54% to 68% within a 2-d period and from 72% to 94% within a 4-d period. With hCG treatment, ovulation was synchronous among 70% to 73% of mares within a 2-d period after hCG treatment. In the latter study, the time to ovulation ranged from 8 to 17 d after the last steroid treatment or 18 to 27 d after the first steroid treatment. With an average interval of 22 d from the first steroid treatment to ovulation, a large portion (about 45%) of the interval involves daily handling of animals and steroid hormones.

Although effective, daily steroidal treatment is time consuming and labor intensive. In addition, repeated intramuscular or subcutaneous treatments increase the risk of injection-site inflammation and, as a consequence, some mares will become intolerant to immediate and future injections.

In the present application, treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), may be applied on random days of the estrous cycle to induce the formation of a persistent dominant follicle and delay wave emergence by preventing spontaneous ovulations (i.e., inhibiting the pre-ovulatory rise in estradiol and potentially delaying luteolysis). On Day 5 (Day 0=day of treatment), a luteolytic dose of PGF is given to induce regression of the corpus luteum (CL), followed on Day 7 by an ovulatory dose of GnRH or pLH to synchronize ovulation. Insemination (e.g., artificial insemination) at detected estrus or following treatment with GnRH or pLH on Day 6 or 7 to synchronize ovulation (fixed-time artificial insemination [FTAI] on Day 7-7.5).

Improved Fertility

Treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), given in early metestrus (about Day 1 post-ovulation) or mid-diestrus (about Day 9 post-ovulation) results in a luteotrophic effect, documented by larger CL diameter and greater plasma progesterone profiles in treated animals. Treatment during the early luteal phase increases CL viability and progesterone production, which is important for ensuring rapid growth of a healthy embryo and successful establishment of pregnancy. In high-producing dairy cows, for example, low levels of progesterone account for low pregnancy rates and high embryonic loss rates. Letrozole, (1-2 mg/Kg, IV, SID for 4 days or a slow-release device containing letrozole), is given one day after artificial insemination to promote development of the CL, resulting in a larger CL diameter and higher circulating concentrations of progesterone.

Similarly, treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), may be given so that its effect encompasses the period of maternal recognition of pregnancy (i.e., the time of luteal response to pregnancy). In cattle, letrozole treatment is initiated on or before 15 days after artificial insemination (maternal recognition of pregnancy is between Days 15 and 17 post-ovulation in cattle). Treatment at this time will promote the establishment of pregnancy through two mechanisms. Firstly, letrozole exerts a luteotrophic effect to enhance CL functionality and survival. Secondly, letrozole will compromise the luteolytic mechanism by decreasing circulating estradiol concentration which mediates the luteolytic process by stimulating the expression of oxytocin receptors in the endometrium, which are necessary for prostaglandin production and release. Again, this is a common problem in high producing dairy cattle; low levels of progesterone result in insufficient trophoblast expansion to block prostaglandin production and release from the uterus.

For embryo transfer recipients, treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), is initiated prior to ovulatory follicular wave emergence to induce co-dominance, and double ovulation. A lipid-based formulation as described herein, a waxed-based formulation as described herein, a lipid-based formulation with a gel coat, and/or a waxed-based formulation with a gel coat as described herein, comprising an aromatase inhibitor (such as letrozole), is given from Day 1 (Day 0=wave emergence) until Day 7. PGF is administered on day 5 followed by GnRH/LH treatment 36 h later. As a result, recipient animals will have more than one corpus luteum and higher progesterone levels to ensure a successful attachment and development of the transferred embryo. An alternative protocol for embryo transfer recipients is letrozole treatment, in a slow-release preparation, initiated one day after ovulation for 5 days to promote development of the new CL, resulting in a larger CL diameter and higher circulating concentrations of progesterone.

Twinning

Treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), given before dominant follicle selection, induces the development of co-dominance; i.e., 2 dominant follicles. The data suggest that letrozole may be used to produce double ovulations and twin pregnancies with much higher efficiency than other previously explored treatments (e.g., eCG or FSH). The advantage of letrozole treatment is that it appears to induce the development of only two dominant follicles, which overcome the adverse effects of gonadotropin treatments where multiple (3 to 10) ovulations and conceptions commonly occur. In this regard, a letrozole-impregnated slow-releasing device may be applied on the day of or the day after follicle wave emergence of either an anovulatory or ovulatory follicular wave. On Day 5 after wave emergence, the letrozole device is removed and a luteolytic dose of PGF given. Artificial insemination at detected estrus or following treatment with GnRH or pLH on Day 6 or 7 to synchronize ovulation (FTAI) would be expected to result in twin pregnancies.

Inducing multiple ovulation in mares is difficult and expensive. Treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), may be used in mares, with or without other superstimulatory hormones (e.g., FSH or equine pituitary extract), to induce multiple ovulation in mares for the purposes of embryo production and embryo transfer.

Induction of Ovulation in Women and Non-Human Primates

Treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), during the expected time of ovulation can be used to trigger the physiologic cascade of events leading to ovulation. Women treated with Letrozole at 18 mm follicle diameter ovulate 24 hours earlier than controls. This indicates Letrozole may be used to induce ovulation in place of either hCG or GnRH should it be advantageous to avoid the use of glycoprotein preparations.

Inhibition of Ovulation in Cattle and Other Ungulates

Treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), during the expected time of ovulation (during the late follicular phase of the estrous cycle) can be used to prevent the increase on estradiol concentration and therefore the LH surge that triggers ovulation. Treatment with letrozole during the pre-ovulatory wave in cattle delays ovulation for 24 hr.

Ovarian Superstimulation

The addition a lipid-based formulation as described herein, a waxed-based formulation as described herein, a lipid-based formulation with a gel coat, and/or a waxed-based formulation with a gel coat as described herein, comprising an aromatase inhibitor (such as letrozole), in superovulation protocols can reduce the mass/volume/dose of gonadotropins required to achieve a good ovarian response to the exogenous gonadotrophins or other ovarian stimulation protocols that may be used to increase the number and or quality of oocytes to be ovulated or removed via ovarian follicular aspiration. In addition, reducing the amount/volume/mass of gonadotropins required to generate an adequate ovarian response is expected to reduce the risk of ovarian hyperstimulation syndrome in women and other mammals where OHSS may be problematic.

The addition of letrozole in superovulation protocols can reduce the total dose of gonadotropins required to achieve the desired ovarian response to the exogenous gonadotrophins or other ovarian stimulation protocols that may be used to increase the number of ovulations or the number of oocytes collected via ovarian follicular aspiration. In addition, reducing the amount/volume/mass of gonadotropins required to generate an adequate ovarian response is expected to reduce the risk of ovarian hyperstimulation syndrome in women and other mammals where OHSS may be problematic.

Increase Fertility after Ovarian Superstimulation Treatment

Treatment with a lipid-based formulation as described herein, a waxed-based formulation as described herein, a lipid-based formulation with a gel coat, and/or a waxed-based formulation with a gel coat as described herein, comprising an aromatase inhibitor (such as letrozole), during superovulation protocols can help to reduce the increased concentration of estradiol that is normally observed in superstimulated individuals, therefore favoring sperm transport and uterine maturation for future implantation as well as oocyte competence.

Letrozole treatment during superovulation protocols can help to reduce the increased concentration of estradiol associated with ovarian superstimulation, thereby enhancing sperm transport and uterine maturation for future implantation as well as oocyte competence.

In the preceding description, for purposes of explanation, numerous details are set forth in order to provide a thorough understanding of the embodiments. However, it will be apparent to one skilled in the art that these specific details are not required. All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference, The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

The above-described embodiments are intended to be examples only. Alterations, modifications and variations can be effected to the particular embodiments by those of skill in the art without departing from the scope, which is defined solely by the claims appended hereto.

The invention claimed is:

1. A delivery vehicle for the delivery of an aromatase inhibitor to a mammal, said vehicle comprising: a wax delivery system comprising phosphatidylcholine (PC), dioleoyl phosphatidylethanolamine (DOPE), cholesterol, synthetic hydrogenated oil, and an aromatase inhibitor; and a gel coat comprising the aromatase inhibitor, gelatin, a polymer; and water, wherein said gel coat covers said wax delivery system, wherein said vehicle is suitable for delivering said aromatase inhibitor to the plasma of said mammal.

2. The vehicle of claim 1, wherein said wax delivery system comprises (w/w) about 10% letrozole; about 10% phosphatidylcholine (PC); about 2% DOPE; about 5% cholesterol; and synthetic hydrogenated oil q.s. to 100%.

3. The vehicle of claim 1, wherein the aromatase inhibitor is letrozole.

4. The vehicle of claim 1, wherein said polymer comprises poloxamer 188 and/or poloxamer 407.

5. The vehicle of claim 1, wherein said gel coat comprises (w/w): 10% letrozole, 20% gelatin, 65% polymer, and water q.s. to 100%.

6. An intravaginal aromatase inhibitor delivery system comprising the delivery vehicle of claim 1 and an intravaginal delivery device.

7. A method of providing an aromatase inhibitor to the plasma of a subject, comprising: vaginal administration of a vehicle according to claim 1.

8. The method of claim 7, wherein said subject is a mammal.

9. A method of synchronizing ovulation in a mammal, comprising: administering a delivery vehicle according to claim 1 to said mammal so as to induce the formation of a persistent follicle and delay wave emergence by preventing spontaneous ovulation in said mammal; administering a luteolytic dose of a prostaglandin so as to induce regression of the corpus *luteum* of said mammal; and administering an ovulatory dose of GnRH or pLH to said mammal.

10. A method of synchronizing ovulation in a mammal, comprising: administering an effective amount of a prostaglandin; and administering a delivery vehicle according to claim 1 to said mammal.

* * * * *